US012799210B2

(12) United States Patent
Zhou et al.

(10) Patent No.: US 12,799,210 B2
(45) Date of Patent: Nov. 17, 2026

(54) SIGNAL PEPTIDE FOR REDUCING END HETEROGENEITY OF HETEROLOGOUS POLYPEPTIDE

(71) Applicants: JIANGSU HENGRUI PHARMACEUTICALS CO., LTD., Lianyungang (CN); SHANGHAI HENGRUI PHARMACEUTICAL CO., LTD., Shanghai (CN)

(72) Inventors: Songtao Zhou, Shanghai (CN); Xun Liu, Shanghai (CN)

(73) Assignees: JIANGSU HENGRUI PHARMACEUTICALS CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 765 days.

(21) Appl. No.: 18/023,301

(22) PCT Filed: Aug. 27, 2021

(86) PCT No.: PCT/CN2021/114911
§ 371 (c)(1),
(2) Date: Feb. 24, 2023

(87) PCT Pub. No.: WO2022/042673
PCT Pub. Date: Mar. 3, 2022

(65) Prior Publication Data

US 2023/0312725 A1 Oct. 5, 2023

(30) Foreign Application Priority Data

Aug. 28, 2020 (CN) ......................... 202010882873.5
Aug. 20, 2021 (CN) ......................... 202110958128.9

(51) Int. Cl.
*C07K 16/28* (2006.01)
*A61K 39/00* (2006.01)

(52) U.S. Cl.
CPC ............ *C07K 16/283* (2013.01); *A61K 39/00* (2013.01); *C07K 16/28* (2013.01); *C07K 2317/14* (2013.01); *C07K 2317/24* (2013.01); *C07K 2317/565* (2013.01); *C07K 2317/567* (2013.01); *C07K 2317/732* (2013.01); *C07K 2317/92* (2013.01); *C07K 2319/02* (2013.01)

(58) Field of Classification Search
None
See application file for complete search history.

(56) References Cited

U.S. PATENT DOCUMENTS

| | | | | |
|---|---|---|---|---|
| 6,403,769 | B1 | 6/2002 | Larochelle et al. | |
| 2004/0115775 | A1 | 6/2004 | Chitlaru et al. | |
| 2011/0091480 | A1 * | 4/2011 | Brown ............... | C07K 16/1271 435/69.6 |
| 2015/0225482 | A1 | 8/2015 | Song | |

FOREIGN PATENT DOCUMENTS

| | | | |
|---|---|---|---|
| CN | 101460520 | A | 6/2009 |
| WO | 2005070962 | A1 | 8/2005 |
| WO | 2016166122 | A1 | 10/2016 |

OTHER PUBLICATIONS

Ying Chen et al., Effects of various signal peptides on expression of GLP-1-Fc fusion protein, Chinese Journal of Biologicals, Dec. 2018, vol. 31, No. 12, pp. 1326-1332, China Academic Journal Electronic Publishing House, DOI:10.13200/j.cnki.cjb.002410 (7 pages).

* cited by examiner

*Primary Examiner* — Brian Gangle
(74) *Attorney, Agent, or Firm* — Morgan, Lewis & Bockius LLP

(57) ABSTRACT

The present invention relates to a signal peptide for reducing the end heterogeneity of a heterologous polypeptide. Specifically, the present invention relates to a signal peptide for protein expression. The present invention further relates to a recombinant polypeptide, a preparation method therefor, and a composition containing a recombinant polypeptide.

6 Claims, 10 Drawing Sheets

Specification includes a Sequence Listing.

SIGNAL PEPTIDE FOR REDUCING END HETEROGENEITY OF HETEROLOGOUS POLYPEPTIDE

CROSS-REFERENCE TO RELATED APPLICATIONS

The present application is a national stage application of International Patent Application No. PCT/CN2021/114911, filed Aug. 27, 2021, which claims the benefit of and priority to Chinese Patent Application Nos. 202010882873.5, filed Aug. 28, 2020, and 202110958128.9 filed Aug. 20, 2021, all of which are incorporated herein by reference in their entirety.

SEQUENCE LISTING

The instant application contains a Sequence Listing which has been submitted electronically in ASCII format and is hereby incorporated by reference in its entirety. Said ASCII copy, Feb. 23, 2023, is named "721100CPUS_126268-5055-US_Sequence_Listing.txt" and is approximately 189 kilobytes in size.

TECHNICAL FIELD

The present disclosure relates to the field of molecular biology and protein engineering, and in particular to a method for reducing terminal heterogeneity of a heterologous polypeptide.

BACKGROUND

The statements herein merely provide background information related to the present disclosure and may not necessarily constitute the prior art.

Signal peptides are short peptide chains that direct the transfer of newly synthesized proteins to the secretory pathway. The signal peptide is located at the N-terminus of the secreted protein. It generally consists of 15-30 amino acids. It usually comprises three regions: a positively charged N-terminus, which is referred to as the basic amino terminal; an intermediate hydrophobic sequence, which is mainly composed of neutral amino acids and capable of forming an a helix structure and is the main functional region of the signal peptide; and a longer, negatively charged C-terminus, which contains small amino acids, is the signal sequence cleavage site and is also known as the processing region. When synthesized, the signal peptide sequence is recognized by a signal recognition particle (SRP), and the protein synthesis is suspended or slowed. The signal recognition particle carries the ribosome onto the endoplasmic reticulum, and the protein synthesis is resumed. Under the guidance of the signal peptide, the newly synthesized protein enters the lumen of the endoplasmic reticulum, and the signal peptide sequence is cleaved under the action of a signal peptidase.

Generally, efficient cleavage of the signal peptide ensures that both the light and heavy chain polypeptides of the antibody can be accurately cleaved, which is very important for mammalian cell-mediated antibody expression. However, during cleavage of the signal peptide, the cleavage site may be changed, resulting in extension or truncation of the light and heavy amino acid chains of the recombinant antibody. For a truncated or extended antibody, its structural changes will result in changes in affinity, thereby affecting antibody activity; therefore, the extension or truncation of the amino acid chain needs to be avoided during antibody production. In addition, a part of the products was truncated or extended, so that the product quality varies from batch to batch in the production process, additional quality control is required, and such a problem is difficult to solve technically. Therefore, it is currently a common consensus in the industry to produce light and heavy chain antibodies with N-terminal homogeneity.

SUMMARY

The present disclosure relates to a signal peptide and use thereof, wherein the signal peptide is used to reduce terminal heterogeneity of a heterologous polypeptide.

The present disclosure provides a method for reducing the N-terminal heterogeneity of a heavy chain of an antibody and/or a light chain of an antibody, which comprises culturing a host cell, wherein the host cell comprises:

(1) a first polynucleotide encoding the heavy chain of the antibody and a first signal peptide operably linked to the N-terminus of the heavy chain; wherein the first signal peptide comprises an amino acid sequence of SEQ ID NO: 55 or SEQ ID NO: 56; and/or (2) a second polynucleotide encoding the light chain of the antibody and a second signal peptide operably linked to the N-terminus of the light chain; wherein the second signal peptide comprises an amino acid sequence of SEQ ID NO: 55 or SEQ ID NO: 56; and expressing the heavy chain of the antibody and/or the light chain of the antibody;

wherein, the SEQ ID NO: 55 is set forth in MEWSWVFLFFLSLTGX$_1$HX$_2$, wherein X$_1$ is V, A, S, T, G, C, L or I, and X$_2$ is A, G, S, C, T or Q;

the SEQ ID NO: 56 is set forth in MSVPTQVLGLLLLWLTDX$_3$RX$_4$, wherein X$_3$ is V, A, S, T, G, C, L or I, X$_4$ is A, G, S, C, T or Q, and X$_4$ is not C when X$_3$ is selected from A.

In some embodiments, provided is the method for reducing N-terminal heterogeneity of a heavy chain of an antibody and/or a light chain of an antibody described above, wherein the heavy chain of the antibody obtained through expression has a terminal extension ratio of less than 3%, 2.5%, 2%, 1.5% or 1%, and/or the light chain of the antibody obtained through expression has a terminal extension ratio of less than 3%, 2.5%, 2%, 1.5% or 1%; in some embodiments, the heavy chain of the antibody obtained through expression has a terminal extension ratio of less than 1%, and/or the light chain of the antibody obtained through expression has a terminal extension ratio of less than 1%. In some embodiments, the terminal extension ratio is measured based on a peptide mapping assay. In some embodiments, the heavy chain of the antibody obtained through expression is substantially free of residual terminal residues, and/or the light chain of the antibody obtained through expression is substantially free of residual terminal residues; in some embodiments, the heavy chain of the antibody obtained through expression has a terminal extension ratio of 0%, and/or the light chain of the antibody obtained through expression has a terminal extension ratio of 0%.

In some embodiments, provided is the method for reducing N-terminal heterogeneity of a heavy chain of an antibody and/or a light chain of an antibody described above, wherein the first signal peptide or the second signal peptide each independently comprises a peptide selected from the group consisting of:

```
SEQ ID NO: 57:
MEWSWVFLFFLSLTGVHA;

SEQ ID NO: 58:
MEWSWVFLFFLSLTGVHG;

SEQ ID NO: 59:
MEWSWVFLFFLSLTGVHS;
```

-continued

SEQ ID NO: 60:
MEWSWVFLFFLSLTGVHC;

SEQ ID NO: 61:
MEWSWVFLFFLSLTGVHT;

SEQ ID NO: 62:
MEWSWVFLFFLSLTGVHQ;

SEQ ID NO: 63:
MEWSWVFLFFLSLTGAHA;

SEQ ID NO: 64:
MEWSWVFLFFLSLTGAHG;

SEQ ID NO: 65:
MEWSWVFLFFLSLTGAHS;

SEQ ID NO: 66:
MEWSWVFLFFLSLTGAHC;

SEQ ID NO: 67:
MEWSWVFLFFLSLTGAHT;

SEQ ID NO: 68:
MEWSWVFLFFLSLTGAHQ;

SEQ ID NO: 69:
MEWSWVFLFFLSLTGSHA;

SEQ ID NO: 70:
MEWSWVFLFFLSLTGSHG;

SEQ ID NO: 71:
MEWSWVFLFFLSLTGSHS;

SEQ ID NO: 72:
MEWSWVFLFFLSLTGSHC;

SEQ ID NO: 73:
MEWSWVFLFFLSLTGSHT;

SEQ ID NO: 74:
MEWSWVFLFFLSLTGSHQ;

SEQ ID NO: 75:
MEWSWVFLFFLSLTGTHA;

SEQ ID NO: 76:
MEWSWVFLFFLSLTGTHG;

SEQ ID NO: 77:
MEWSWVFLFFLSLTGTHS;

SEQ ID NO: 78:
MEWSWVFLFFLSLTGTHC;

SEQ ID NO: 79:
MEWSWVFLFFLSLTGTHT;

SEQ ID NO: 80:
MEWSWVFLFFLSLTGTHQ;

SEQ ID NO: 81:
MEWSWVFLFFLSLTGGHA;

SEQ ID NO: 82:
MEWSWVFLFFLSLTGGHG;

SEQ ID NO: 83:
MEWSWVFLFFLSLTGGHS;

SEQ ID NO: 84:
MEWSWVFLFFLSLTGGHC;

SEQ ID NO: 85:
MEWSWVFLFFLSLTGGHT;

SEQ ID NO: 86:
MEWSWVFLFFLSLTGGHQ;

-continued

SEQ ID NO: 87:
MEWSWVFLFFLSLTGCHA;

SEQ ID NO: 88:
MEWSWVFLFFLSLTGCHG;

SEQ ID NO: 89:
MEWSWVFLFFLSLTGCHS;

SEQ ID NO: 90:
MEWSWVFLFFLSLTGCHC;

SEQ ID NO: 91:
MEWSWVFLFFLSLTGCHT;

SEQ ID NO: 92:
MEWSWVFLFFLSLTGCHQ;

SEQ ID NO: 93:
MEWSWVFLFFLSLTGLHA;

SEQ ID NO: 94:
MEWSWVFLFFLSLTGLHG;

SEQ ID NO: 95:
MEWSWVFLFFLSLTGLHS;

SEQ ID NO: 96:
MEWSWVFLFFLSLTGLHC;

SEQ ID NO: 97:
MEWSWVFLFFLSLTGLHT;

SEQ ID NO: 98:
MEWSWVFLFFLSLTGLHQ;

SEQ ID NO: 99:
MEWSWVFLFFLSLTGIHA;

SEQ ID NO: 100:
MEWSWVFLFFLSLTGIHG;

SEQ ID NO: 101:
MEWSWVFLFFLSLTGIHS;

SEQ ID NO: 102:
MEWSWVFLFFLSLTGIHC;

SEQ ID NO: 103:
MEWSWVFLFFLSLTGIHT;

SEQ ID NO: 104:
MEWSWVFLFFLSLTGIHQ;

SEQ ID NO: 105:
MSVPTQVLGLLLLWLTDVRA;

SEQ ID NO: 106:
MSVPTQVLGLLLLWLTDVRG;

SEQ ID NO: 107:
MSVPTQVLGLLLLWLTDVRS;

SEQ ID NO: 108:
MSVPTQVLGLLLLWLTDVRC;

SEQ ID NO: 109:
MSVPTQVLGLLLLWLTDVRT;

SEQ ID NO: 110:
MSVPTQVLGLLLLWLTDVRQ;

SEQ ID NO: 111:
MSVPTQVLGLLLLWLTDARA;

SEQ ID NO: 112:
MSVPTQVLGLLLLWLTDARG;

SEQ ID NO: 113:
MSVPTQVLGLLLLWLTDARS;

-continued

SEQ ID NO: 114:
MSVPTQVLGLLLLWLTDART;

SEQ ID NO: 115:
MSVPTQVLGLLLLWLTDARQ;

SEQ ID NO: 116:
MSVPTQVLGLLLLWLTDSRA;

SEQ ID NO: 117:
MSVPTQVLGLLLLWLTDSRG;

SEQ ID NO: 118:
MSVPTQVLGLLLLWLTDSRS;

SEQ ID NO: 119:
MSVPTQVLGLLLLWLTDSRC;

SEQ ID NO: 120:
MSVPTQVLGLLLLWLTDSRT;

SEQ ID NO: 121:
MSVPTQVLGLLLLWLTDSRQ;

SEQ ID NO: 122:
MSVPTQVLGLLLLWLTDTRA;

SEQ ID NO: 123:
MSVPTQVLGLLLLWLTDTRG;

SEQ ID NO: 124:
MSVPTQVLGLLLLWLTDTRS;

SEQ ID NO: 125:
MSVPTQVLGLLLLWLTDTRC;

SEQ ID NO: 126:
MSVPTQVLGLLLLWLTDTRT;

SEQ ID NO: 127:
MSVPTQVLGLLLLWLTDTRQ;

SEQ ID NO: 128:
MSVPTQVLGLLLLWLTDGRA;

SEQ ID NO: 129:
MSVPTQVLGLLLLWLTDGRG;

SEQ ID NO: 130:
MSVPTQVLGLLLLWLTDGRS;

SEQ ID NO: 131:
MSVPTQVLGLLLLWLTDGRC;

SEQ ID NO: 132:
MSVPTQVLGLLLLWLTDGRT;

SEQ ID NO: 133:
MSVPTQVLGLLLLWLTDGRQ;

SEQ ID NO: 134:
MSVPTQVLGLLLLWLTDCRA;

SEQ ID NO: 135:
MSVPTQVLGLLLLWLTDCRG;

SEQ ID NO: 136:
MSVPTQVLGLLLLWLTDCRS;

SEQ ID NO: 137:
MSVPTQVLGLLLLWLTDCRC;

SEQ ID NO: 138:
MSVPTQVLGLLLLWLTDCRT;

SEQ ID NO: 139:
MSVPTQVLGLLLLWLTDCRQ;

SEQ ID NO: 140:
MSVPTQVLGLLLLWLTDLRA;

-continued

SEQ ID NO: 141:
MSVPTQVLGLLLLWLTDLRG;

SEQ ID NO: 142:
MSVPTQVLGLLLLWLTDLRS;

SEQ ID NO: 143:
MSVPTQVLGLLLLWLTDLRC;

SEQ ID NO: 144:
MSVPTQVLGLLLLWLTDLRT;

SEQ ID NO: 145:
MSVPTQVLGLLLLWLTDLRQ;

SEQ ID NO: 146:
MSVPTQVLGLLLLWLTDIRA;

SEQ ID NO: 147:
MSVPTQVLGLLLLWLTDIRG;

SEQ ID NO: 148:
MSVPTQVLGLLLLWLTDIRS;

SEQ ID NO: 149:
MSVPTQVLGLLLLWLTDIRC;

SEQ ID NO: 150:
MSVPTQVLGLLLLWLTDIRT;
and

SEQ ID NO: 151:
MSVPTQVLGLLLLWLTDIRQ.

In some embodiments, provided is the method for reducing N-terminal heterogeneity of a heavy chain of an antibody and/or a light chain of an antibody described above, wherein the first signal peptide or the second signal peptide each independently comprises an amino acid sequence of SEQ ID NO: 57, SEQ ID NO: 58, SEQ ID NO: 59, SEQ ID NO: 93, SEQ ID NO: 94, SEQ ID NO: 95, SEQ ID NO: 99, SEQ ID NO: 100, SEQ ID NO: 101, SEQ ID NO: 105, SEQ ID NO: 106, SEQ ID NO: 107, SEQ ID NO: 140, SEQ ID NO: 141, SEQ ID NO: 142, SEQ ID NO: 146, SEQ ID NO: 147 or SEQ ID NO: 148.

In some embodiments, provided is the method for reducing N-terminal heterogeneity of a heavy chain of an antibody and/or a light chain of an antibody described above, wherein the first signal peptide comprises the amino acid sequence of SEQ ID NO: 57 or SEQ ID NO: 105, and/or the second signal peptide comprises the amino acid sequence of SEQ ID NO: 57 or SEQ ID NO: 105.

In some embodiments, provided is the method for reducing N-terminal heterogeneity of a heavy chain of an antibody and/or a light chain of an antibody described above, wherein the first signal peptide comprises the amino acid sequence of SEQ ID NO: 57, and/or the second signal peptide comprises the amino acid sequence of SEQ ID NO: 57.

In some embodiments, provided is the method for reducing N-terminal heterogeneity of a heavy chain of an antibody and/or a light chain of an antibody described above, wherein the first signal peptide comprises the amino acid sequence of SEQ ID NO: 57, and/or the second signal peptide comprises the amino acid sequence of SEQ ID NO: 105.

In some embodiments, provided is the method for reducing N-terminal heterogeneity of a heavy chain of an antibody and/or a light chain of an antibody described above, wherein the first signal peptide comprises the amino acid sequence of SEQ ID NO: 105, and/or the second signal peptide comprises the amino acid sequence of SEQ ID NO: 57.

In some embodiments, provided is the method for reducing N-terminal heterogeneity of a heavy chain of an antibody and/or a light chain of an antibody described above, wherein the first signal peptide comprises the amino acid sequence of SEQ ID NO: 105, and/or the second signal peptide comprises the amino acid sequence of SEQ ID NO: 105.

In some embodiments, provided is the method for reducing N-terminal heterogeneity of a heavy chain of an antibody and/or a light chain of an antibody described above, wherein the first polynucleotide or the second polynucleotide each independently encodes a polypeptide comprising an amino acid sequence selected from the group consisting of SEQ ID NO: 157, SEQ ID NO: 158, SEQ ID NO: 159, SEQ ID NO: 160, SEQ ID NO: 163, SEQ ID NO: 164, SEQ ID NO: 165, SEQ ID NO: 166, SEQ ID NO: 171 and SEQ ID NO: 172.

In some embodiments, provided is the method for reducing N-terminal heterogeneity of a heavy chain of an antibody and/or a light chain of an antibody described above, wherein the host cell is a eukaryotic host cell; in some embodiments, the eukaryotic host cell is a CHO cell or a yeast.

In some embodiments, provided is the method for reducing N-terminal heterogeneity of a heavy chain of an antibody and/or a light chain of an antibody described above, wherein the antibody is a murine antibody, a chimeric antibody, a humanized antibody, a human antibody, an affinity-matured antibody or a multispecific antibody.

In some embodiments, provided is the method for reducing N-terminal heterogeneity of a heavy chain of an antibody and/or a light chain of an antibody described above, wherein the antibody is selected from the group consisting of an anti-TLR7 antibody, an anti-HER2 (ErbB2) antibody, an anti-Claudin18.2 antibody, an anti-EGFR antibody, an anti-B7H3 antibody, an anti-c-Met antibody, an anti-HER3 (ErbB3) antibody, an anti-HER4 (ErbB4) antibody, an anti-CD3 antibody, an anti-CD20 antibody, an anti-CD22 antibody, an anti-CD30 antibody, an anti-CD33 antibody, an anti-CD38 antibody, an anti-CD44 antibody, an anti-CD47 antibody, an anti-CD56 antibody, an anti-CD70 antibody, an anti-CD73 antibody, an anti-CD105 antibody, an anti-CEA antibody, an anti-A33 antibody, an anti-Cripto antibody, an anti-SOST antibody, an anti-EphA2 antibody, an anti-G250 antibody, an anti-MUC1 antibody, an anti-Lewis Y antibody, an anti-VEGFR antibody, an anti-GPNMB antibody, an anti-thrombin antibody, an anti-Aβ antibody, an anti-Integrin antibody, an anti-ANGPTL3 antibody, an anti-PSMA antibody, an anti-PD-1 antibody, an anti-PD-L1 antibody, an anti-LAG3 antibody, an anti-IL-5 antibody, an anti-IL-15 antibody, an anti-IL-4R antibody, an anti-IL-6R antibody, an anti-TIGHT antibody, an anti-Tenascin-C antibody, an anti-SLC44A4 antibody, an anti-PCSK9 antibody, an anti-EpCAM antibody, an anti-CTGF antibody, an anti-TSLP antibody, an anti-CEA antibody, an anti-Mesothelin antibody and an anti-FcRn antibody.

In some embodiments, provided is the method for reducing N-terminal heterogeneity of a heavy chain of an antibody and/or a light chain of an antibody described above, wherein the antibody is selected from the group consisting of trastuzumab, pertuzumab, nimotuzumab, enoblituzumab, emibetuzumab, inotuzumab, pinatuzumab, brentuximab, gemtuzumab, bivatuzumab, lorvotuzumab, cBR96, glematumamab, an anti-Claudin18.2 antibody and an anti-FcRn antibody, wherein a heavy chain and a light chain of the anti-Claudin18.2 antibody comprise amino acid sequences of SEQ ID NO: 49 and SEQ ID NO: 47, respectively; a heavy chain and a light chain of the anti-FcRn antibody comprise amino acid sequences of SEQ ID NO: 167 and SEQ ID NO: 168, respectively.

In some embodiments, provided is the method for reducing N-terminal heterogeneity of a heavy chain of an antibody and/or a light chain of an antibody described above, which comprises cloning a light chain plasmid into a heavy chain plasmid to construct a full-length antibody plasmid. In some embodiments, in the method, the plasmid is introduced into the host cell by electroporation.

The present disclosure further provides a signal peptide comprising or consisting of an amino acid sequence of SEQ ID NO: 55 or SEQ ID NO: 56. In some embodiments, the polypeptide is a signal peptide having an amino acid sequence set forth in any one of SEQ ID NO: 55 to SEQ ID NO: 151.

Provided is a polypeptide, which comprises a signal peptide comprising an amino acid sequence of SEQ ID NO: 55 or SEQ ID NO: 56.

In some embodiments, provide is the polypeptide described above, wherein the polypeptide further comprises a heterologous polypeptide operably linked to the signal peptide; in some embodiments, the heterologous polypeptide is a heavy chain of an antibody or a light chain of an antibody; in some embodiments, the signal peptide is operably linked to the N-terminus of the heavy chain of the antibody or the light chain of the antibody.

In some embodiments, provided is the polypeptide described above, wherein the signal peptide comprises an amino acid sequence selected from the group consisting of SEQ ID NO: 57 to SEQ ID NO: 151.

In some embodiments, provided is the polypeptide described above, wherein the signal peptide comprises an amino acid sequence of SEQ ID NO: 57, SEQ ID NO: 58, SEQ ID NO: 59, SEQ ID NO: 93, SEQ ID NO: 94, SEQ ID NO: 95, SEQ ID NO: 99, SEQ ID NO: 100, SEQ ID NO: 101, SEQ ID NO: 105, SEQ ID NO: 106, SEQ ID NO: 107, SEQ ID NO: 140, SEQ ID NO: 141, SEQ ID NO: 142, SEQ ID NO: 146, SEQ ID NO: 147 or SEQ ID NO: 148.

In some embodiments, provided is the polypeptide described above, wherein the signal peptide comprises an amino acid sequence selected from the group consisting of SEQ ID NO: 57 and SEQ ID NO: 105.

In some embodiments, provided is the polypeptide described above, wherein the polypeptide comprises an amino acid sequence selected from the group consisting of SEQ ID NO: 157, SEQ ID NO: 158, SEQ ID NO: 159, SEQ ID NO: 160, SEQ ID NO: 163, SEQ ID NO: 164, SEQ ID NO: 165, SEQ ID NO: 166, SEQ ID NO: 169, SEQ ID NO: 170, SEQ ID NO: 171 and SEQ ID NO: 172.

The present disclosure further provides a nucleic acid molecule, which encodes the polypeptide according to any one of the preceding embodiments.

The present disclosure further provides a host cell, which comprises the nucleic acid molecule described above.

In some embodiments, provided is the host cell described above, wherein the host cell is a eukaryotic host cell; in some embodiments, the eukaryotic host cell is a CHO cell or a yeast.

The present disclosure further provides a composition, which comprises a heterologous polypeptide having a terminal extension ratio of less than 3%, 2.5%, 2%, 1.5%, or 1%; in some embodiments, the heterologous polypeptide obtained through expression has a terminal extension ratio of less than 1%; in some embodiments, the heterologous polypeptide obtained through expression has a terminal extension ratio of less than 1%, and the terminal extension ratio is measured based on a peptide mapping assay; in some embodiments, the heterologous polypeptide obtained through expression is substantially free of residual terminal residues; in some embodiments, the heterologous polypeptide obtained through expression has a terminal extension ratio of 0%.

In some embodiments, provided is the composition described above, wherein the heterologous polypeptide is a heavy chain of an antibody and/or a light chain of an antibody; in some embodiments, the antibody is selected from the group consisting of trastuzumab, pertuzumab, an anti-Claudin18.2 antibody and an anti-FcRn antibody, wherein a heavy chain and a light chain of the anti-Claudin18.2 antibody comprise amino acid sequences of SEQ ID NO: 49 and SEQ ID NO: 47, respectively.

In some embodiments, the antibody is selected from an anti-FcRn antibody, wherein a heavy chain and a light chain of the anti-FcRn antibody comprise amino acid sequences of SEQ ID NO: 167 and SEQ ID NO: 168, respectively.

In some embodiments, provided is the method for reducing N-terminal heterogeneity of a heavy chain of an antibody and/or a light chain of an antibody described above, wherein the heavy chain of the antibody and/or the light chain of an antibody obtained through expression have a terminal extension ratio of less than 3%, 2.5%, 2%, 1.5%, or 1%; in some embodiments, the heavy chain of the antibody and/or the light chain of the antibody obtained through expression have a terminal extension ratio of less than 1%; in some embodiments, the heavy chain of the antibody and/or the light chain of the antibody obtained through expression have a terminal extension ratio of less than 1%, and the terminal extension ratio is measured based on a peptide mapping assay; in some embodiments, the heavy chain of the antibody and/or the light chain of the antibody obtained through expression are substantially free of residual terminal residues; in some embodiments, the heavy chain of the antibody and/or the light chain of the antibody obtained through expression have a terminal extension ratio of 0%.

In some embodiments, provided is the composition described above, which is prepared by the method according to any one of the preceding embodiments.

The signal peptide provided by the present disclosure has the effect of stably reducing terminal heterogeneity of a heterologous polypeptide, and is suitable for expressing heterologous polypeptides in large scale.

BRIEF DESCRIPTION OF THE DRAWINGS

FIG. 3A shows the detection of ADCC effect of antibodies in wild-type NUGC4 cells (with low Claudin18.2 expression); FIG. 3B shows the detection of ADCC effect of antibodies in NUGC4 cells with moderate Claudin18.2 expression; FIG. 3C shows the detection of ADCC effect of antibodies in NUGC4 cells with high Claudin18.2 expression.

FIG. 4A shows the mass spectrum of the molecular weight after deglycosylation and reduction of the light chain of pertuzumab-1 antibody; FIG. 4B shows the mass spectrum of the molecular weight after deglycosylation and reduction of the light chain of pertuzumab-3 antibody; FIG. 4C shows the mass spectrum of the molecular weight after deglycosylation and reduction of the heavy chain of pertuzumab-1 antibody; FIG. 4D shows the mass spectrum of the molecular weight after deglycosylation and reduction of the heavy chain of pertuzumab-3 antibody.

FIG. 5A shows the mass spectrum of the molecular weight after deglycosylation and reduction of the light chain of pertuzumab-2 antibody; FIG. 5B shows the mass spectrum of the molecular weight after deglycosylation and reduction of the light chain of pertuzumab-4 antibody; FIG. 5C shows the mass spectrum of the molecular weight after deglycosylation and reduction of the heavy chain of pertuzumab-2 antibody; FIG. 5D shows the mass spectrum of the molecular weight after deglycosylation and reduction of the heavy chain of pertuzumab-4 antibody.

FIG. 6A shows the mass spectrum of the molecular weight after deglycosylation and reduction of the light chain of h1902-5-1 antibody; FIG. 6B shows the mass spectrum of the molecular weight after deglycosylation and reduction of the light chain of h1902-5-2 antibody; FIG. 6C shows the mass spectrum of the molecular weight after deglycosylation and reduction of the heavy chain of h1902-5-1 antibody; FIG. 6D shows the mass spectrum of the molecular weight after deglycosylation and reduction of the heavy chain of h1902-5-2 antibody.

FIG. 7A shows the mass spectrum of the molecular weight after deglycosylation and reduction of the light chain of FcRn-1 antibody; FIG. 7B shows the mass spectrum of the molecular weight after deglycosylation and reduction of the light chain of FcRn-2 antibody; FIG. 7C shows the mass spectrum of the molecular weight after deglycosylation and reduction of the heavy chain of FcRn-1 antibody; FIG. 7D shows the mass spectrum of the molecular weight after deglycosylation and reduction of the heavy chain of FcRn-2 antibody.

DETAILED DESCRIPTION

Detailed Description of the Invention

Terms

Figure 1:
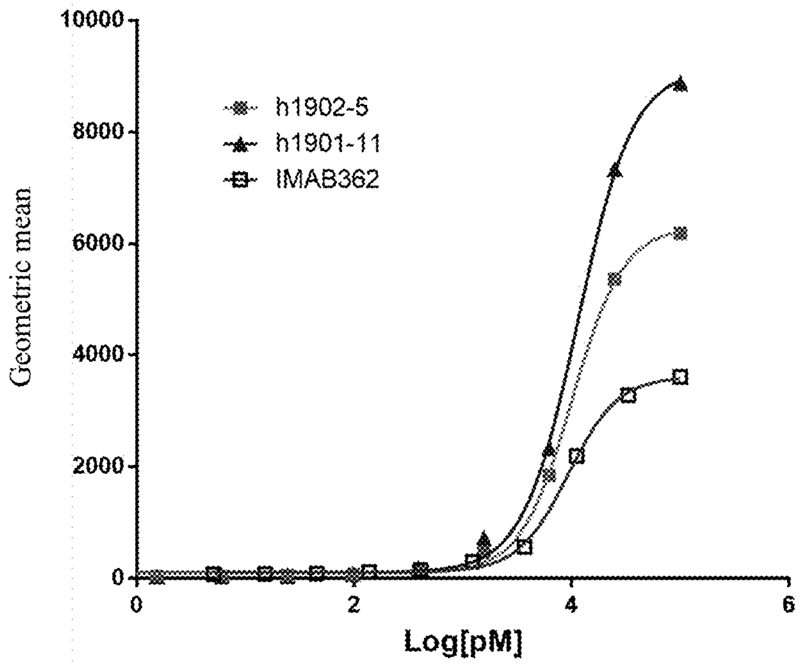
FIG. 1: the results of FACS detection of the binding of humanized antibodies to human Claudin18.2 at cell level.

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs.

The three-letter and single-letter codes for amino acids used herein are as described in *J. biol. chem,* 243, p3558 (1968).

The term "antibody" described herein is used in the broadest sense herein and includes different antibody structures including, but not limited to, a monoclonal antibody, a polyclonal antibody, a murine antibody, a chimeric antibody, a humanized antibody, a multispecific antibody (e.g., a bispecific antibody) and antibody fragments, so long as they exhibit the desired antigen-binding activity and specificity.

The term "antibody fragment" refers to a molecule different from an intact antibody, and it comprises a portion of an intact antibody that specifically binds to an antigen to which the intact antibody specifically binds. Examples of antibody fragments include, but are not limited to, Fv, Fab, Fab', Fab'-SH, $F(ab')_2$, diabodies, linear antibodies, single-chain antibody molecules (e.g., scFv or scFab), single-domain antibodies (dAbs), and multispecific antibodies formed from antibody fragments.

The term "chimeric antibody" described herein refers to an antibody obtained by fusing a variable region of a murine antibody and a constant region of a human antibody, which can reduce an immune response induced by the murine antibody.

The term "humanized antibody" described herein, also known as a CDR-grafted antibody, refers to an antibody produced by grafting murine CDR sequences into a human antibody variable region framework, i.e., a different type of human germline antibody framework sequence. Such an antibody can overcome the heterogeneous reaction induced by the chimeric antibody because of carrying a large amount of mouse protein component. To avoid the decrease in activity caused by the decrease in immunogenicity, the framework region sequence in human antibody variable region can be subjected to minimum reverse mutation or back mutation to maintain or enhance activity. The humanized antibody of the present disclosure also includes humanized antibodies that were further subjected to CDR affinity maturation mutation by yeast display.

The terms "human antibody" (HuMAb), "human-derived antibody", "fully human antibody" and "completely human antibody" herein are used interchangeably and have amino acid sequences corresponding to those of antibodies produced by humans or human cells, or derived from non-human sources using repertoires of human antibodies or other human antibody coding sequences. The definition of such a human antibody specifically excludes humanized antibodies comprising non-human antigen-binding residues.

The term "antibody fragment" described herein refers to a molecule different from an intact antibody, and it comprises a portion of an intact antibody that specifically binds to an antigen to which the intact antibody specifically binds. Examples of antibody fragments include, but are not limited to, Fv, Fab, Fab', Fab'-SH, $F(ab')_2$, diabodies, linear antibodies, single-chain antibody molecules (e.g., scFv or scFab), single-domain antibodies (dAbs), and multispecific antibodies formed from antibody fragments. The term "antibody" of the present disclosure includes "intact antibodies" and "antibody fragments" thereof. Accordingly, the heavy chain of an antibody or the light chain of an antibody described herein includes a complete heavy chain or a complete light chain, and also includes a heavy chain fragment or a light chain fragment of an antibody fragment.

The term "framework" or "FR" refers to variable domain residues other than complementarity determining region (CDR) residues. The FR of a variable domain generally consists of four FR domains: FR1, FR2, FR3 and FR4. Thus, CDR and FR sequences typically occur in a VH (or VL) in the following order:

FR1-HCDR1(LCDR1)-FR2-HCDR2(LCDR2)-FR3-HCDR3(LCDR3)-FR4.

The term "complementarity determining region", "CDR" or "hypervariable region" refers to one of the 6 hypervariable regions within variable domains of an antibody, which primarily contribute to antigen binding. Generally, there are three CDRs (HCDR1, HCDR2 and HCDR3) in each heavy chain variable region and three CDRs (LCDR1, LCDR2 and LCDR3) in each light chain variable region. The amino acid sequence boundaries of the CDRs can be determined using any one of a variety of well-known schemes, including "Kabat" numbering scheme (see Kabat et al. (1991), "Sequences of Proteins of Immunological Interest", 5th edition, Public Health Service, National Institutes of Health, Bethesda, MD), "Chothia" numbering scheme (see Al-Lazikani et al. (1997) *JMB* 273:927-948) and ImMunoGenTics (IMGT) numbering scheme (see Lefranc M. P., *Immunologist,* 7, 132-136 (1999); Lefranc, M. P. et al., *Dev. Comp. Immunol.,* 27, 55-77 (2003)), and the like. For example, for the classical format, according to the Kabat scheme, the CDR amino acid residues in the heavy chain variable domain (VH) are numbered 31-35 (HCDR1), 50-65 (HCDR2) and 95-102 (HCDR3); the CDR amino acid residues in the light chain variable domain (VL) are numbered 24-34 (LCDR1), 50-56 (LCDR2) and 89-97 (LCDR3). According to the Chothia scheme, the CDR amino acids in VH are numbered 26-32 (HCDR1), 52-56 (HCDR2) and 95-102 (HCDR3); and amino acid residues in VL are numbered 26-32 (LCDR1), 50-52 (LCDR2) and 91-96 (LCDR3). According to the CDR definitions of both the Kabat scheme and the Chothia scheme, the CDR is composed of amino acid residues 26-35 (HCDR1), 50-65 (HCDR2) and 95-102 (HCDR3) in the human VH and amino acid residues 24-34 (LCDR1), 50-56 (LCDR2) and 89-97 (LCDR3) in the human VL. According to the IMGT scheme, the CDR amino acid residues in VH are roughly numbered 26-35 (CDR1), 51-57 (CDR2) and 93-102 (CDR3), and the CDR amino acid residues in VL are roughly numbered 27-32 (CDR1), 50-52 (CDR2) and 89-97 (CDR3). According to the IMGT scheme, the CDRs of the antibody can be determined using the program IMGT/DomainGap Align. Unless otherwise stated, the "Kabat" numbering scheme is applied to the sequences of the variable regions and CDRs of the antibody involved in examples of the present disclosure.

The terms "specific binding", "selective binding", "selectively bind to" and "specifically bind to" refer to the binding of an antibody to an epitope on a predetermined antigen. Generally, the antibody binds with an affinity (KD) of less than about $10^{-8}$ M, e.g., less than about $10^{-9}$ M, $10^{-10}$ M, $10^{-11}$ M, $10^{-12}$ M, or less.

The term "KD" refers to the dissociation equilibrium constant for specific antibody-antigen interaction. Typically, an antibody of the present disclosure binds to an antigen with a dissociation equilibrium constant (KD) of less than about $10^{-7}$ M, e.g., less than about $10^{-8}$ M or $10^{-9}$ M. For example, the affinity (KD value) of an antibody to an antigen on the cell surface in the present disclosure is determined by FACS method.

The term "polynucleotide" or "nucleic acid molecule" used interchangeably in the present disclosure refers to a polymer of nucleotides of any length, and includes DNA and RNA. The nucleotides may be deoxyribonucleotides, ribonucleotides, modified nucleotides or bases, and/or analogs thereof, or any substrates that can be incorporated into a polymer by a DNA or RNA polymerase or by a synthetic reaction. Polynucleotides may include modified nucleotides, such as methylated nucleotides and analogs thereof. If present, modifications to the structure of the nucleotide can be made before or after the assembly of the polymer. The sequence of a nucleotide can be interrupted by non-nucleotide components.

The term "operably linked" described herein refers to the juxtaposition of two or more components, wherein the components are in a relationship that allows them to function in their intended manner. For example, a promoter is operably linked to a coding sequence if it acts in cis to control or regulate the transcription of the linked sequence. Generally, but not necessarily, "operably linked" DNA sequences are contiguous and, where necessary to link two protein coding regions or where a secretory leader sequence is involved, contiguous and in reading frame. However, while an operably linked promoter is typically located upstream of a coding sequence, it is not necessarily contiguous therewith. An operably linked enhancer may be located upstream of, within or downstream of a coding sequence and at a considerable distance from the promoter. Linking is accomplished by recombinant methods known in the art, e.g., using PCR method, by annealing, or by linking at convenient restriction sites. If convenient restriction sites do not exist, synthetic oligonucleotide adaptors or linkers are used according to conventional practice. In the present disclosure, one way of linking a signal peptide to a heterologous polypeptide is direct linking.

The term "host cell" described herein refers to a cell that has been genetically altered or is capable of being genetically altered by the introduction of an exogenous polynucleotide (such as a recombinant plasmid or vector). It will be understood that such terms are intended to refer not only to the particular individual cell, but also to the progeny of such a cell. Because certain modifications may occur in successive generations due to either mutation or environmental influence, such progeny may not, in fact, be identical to the parent cell, but are still included within the scope of the term "host cell" used herein. The host cell may be a microorganism (e.g., a eukaryotic microorganism) or an animal cell. Suitable microorganisms include *Saccharomyces cerevisiae* and *Pichia pastoris*, and suitable animal host cell lines include CHO (Chinese hamster ovary cell line), 293 cells and NS0 cells.

The term "polypeptide" described herein broadly refers to a peptide and a protein derived from any cellular source and having more than about 10 amino acids. "Heterologous" polypeptides are those that are foreign to the host cell utilized, such as human proteins produced by the host cell. Heterologous polypeptides may be prokaryotic or eukaryotic, such as mammalian or human. A heterologous polypeptide may be a recombinantly produced polypeptide or a recombinant polypeptide.

Exemplary heterologous polypeptides include transmembrane molecules (e.g., receptors, such as receptor tyrosine kinases) or ligands such as growth factors. Exemplary heterologous polypeptides include molecules such as: renin; growth hormones, including human growth hormone and bovine growth hormone; growth hormone releasing factor; parathyroid hormone; thyroid stimulating hormone; lipoproteins; α1-antitrypsin; insulin A-chain; insulin B-chain; proinsulin; follicle stimulating hormone; calcitonin; luteinizing hormone; glucagon; clotting factors, such as factor VIIIC, factor IX, tissue factor (TF) and von Willebrands factor; anti-clotting factors, such as protein C; atrial natriuretic peptide; lung surfactant; plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); serum albumin, such as human serum albumin; Muellerian-inhibiting substance; relaxin A-chain; relaxin B-chain; prorelaxin; mouse gonadotropin-associated peptide; microbial protein, such as β-lactamase; DNase; IgE; cytotoxic T-lymphocyte associated antigen (CTLA), such as CTLA-4; inhibin; activin; vascular endothelial growth factor (VEGF); receptors for hormones or growth factors; protein A or D; rheumatoid factors; neurotrophic factors, such as bone-derived neurotrophic factor (BDNF), neurotrophin-3, -4, -5 or -6 (NT-3, NT-4, NT-5 or NT-6), or nerve growth factors, such as NGFβ; platelet-derived growth factor (PDGF); fibroblast growth factor, such as aFGF and bFGF; epidermal growth factor (EGF); transforming growth factor (TGF), such as TGF-α and TGF-β, including TGF-β1, TGF-β2, TGF-β3, TGF-β4 or TGF-β5; insulin-like growth factor-I and -II (IGF-I and IGF-II); des(1-3)-IGF-I (brain IGF-I), insulin-like growth factor binding proteins; CD proteins, such as CD3, CD4, CD8, CD19, CD20 and CD40; erythropoietin; osteoinductive factors; immunotoxins; bone morphogenetic protein (BMP); interferons, such as interferon-α, -β, and -γ; colony stimulating factor (CSF), such as M-CSF, GM-CSF and G-CSF; interleukin (IL), such as IL-1 to IL-10; superoxide dismutase; T-cell receptors; surface membrane proteins; decay accelerating factor; viral antigen, such as a portion of the AIDS envelope; transport proteins; homing receptors; addressin; regulatory proteins; integrins, such as CD11a, CD11b, CD11c, CD18, ICAM, VLA-4 and VCAM; tumor associated antigens, such as HER2, HER3 or HER4 receptor; and fragments of any of the above polypeptides.

A heterologous polypeptide may also be an antibody, and illustratively, targets of the antibody include, but are not limited to A33, BMPI, BMP2, BMP3B (GDFIO), BMP4, BMP6, BMP8, CSFI (M-CSF), CSF2 (GM-CSF), CSF3 (G-CSF), EPO, FGFI (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNAI, IFNA2, IFNA4, IFNA5, IFNA6, IFNA7, IFNBI, IFNG, IFNWI, FELI, FELI (EPSELON), FELI (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNF-α), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSFIO (TRAIL), TNFSF1I (TRANCE), TNFSF12 (AP03L), TNFSF13 (April), TNFSF13B, TNFSF14 (HVEM-L), TNFSF15 (VEGI), TNFSF18, HGF (VEGFD), VEGF, VEGFB, VEGFC, ILIR1, IL1R2, IL1RL1, IL1RL2, IL2RA, IL2RB, IL2RG, IL3RA, IL4R, IL5RA, IL6R, IL7R, IL8RA, IL8RB, IL9R, ILIORA, ILIORB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIFI, HGF, LEP (leptin), PTN, THPO, CCLI (I-309), CCL2 (MCP-1/MCAF), CCL3 (MIP-la), CCL4 (MIP-lb), CCL5 (RANTES), CCL7 (MCP-3), CCL8 (mcp-2), CCLH (eotaxin), CCL13 (MCP-4), CCL15 (MIP-ld), CCL16 (HCC-4), CCL17 (TARC), CCL18 (PARC), CCL19 (MDP-3b), CCL20 (MIP-3a), CCL21 (SLC/exodus-2), CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CXCLI (GROI), CXCL2 (GR02), CXCL3 (GR03), CXCL5 (ENA-78), CXCL6 (GCP-2), CXCL9 (MIG), CXCL10 (IP 10), CXCL11 (I-TAC), CXCL12 (SDFI), CXCL13, CXCL14, CXCL16, PF4 (CXCL4), PPBP (CXCL7), CX3CL1 (SCYDI), SCYEI, XCLI (lymphotactin), XCL2 (SCM-1b), BLRI (MDR15), CCBP2 (D6/JAB61), CCR1 (CKRI/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TERI/CKR-LI), CCR9 (GPR-9-6), CCRLI (VSHKI), CCRL2 (L-CCR), XCRI (GPR5/CCXCRI), CMKLRI, CMKORI (RDCI), CX3CR1 (V28), CXCR4, GPR2 (CCRIO), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCPIO, CKLFSF2, CKLFSF3, CKLFSF4, CKLFSF5, CKLFSF6, CKLFSF7, CKLFSF8, BDNF, C5R1, CSF3, GRCCIO (CIO), EPO, FY (DARC), GDF5, HDFIA, DL8, PRL, RGS3, RGS13, SDF2, SLIT2, TLR2, TLR4, TREMI, TREM2, VHL, ABCFI, ACVRI, ACVRIB, ACVR2, ACVR2B, ACVRLI, ADORA2A, Aggrecan, AGR2, AICDA, AIFI, AIGI, AKAPI, AKAP2, AMH, AMHR2, ANGPTI, ANGPT2, ANGPTL3, ANGPTL4, ANPEP, APC, APOCI, AR, AZGPI (zinc-a-glycoprotein), Aβ, B7.1, B7.2, B7H3, BAD, BAFF (BLys), BAGI, BAH, BCL2, BCL6, BDNF, BLNK, BLRI (MDR15), BMPI, BMP2, BMP3B (GDFIO), BMP4, BMP6, BMP8, BMPRIA, BMPRIB, BMPR2, BPAGI (plectin), BRCAI, C19orflO (IL27w), C3, C4A, C5, C5R1, CANTI, CASP1, CASP4, CAVI, CCBP2 (D6/JAB61), CCLI (1-309), CCLII (eotaxin), CCL13 (MCP-4), CCL15 (MIP-ld), CCL16 (HCC-4), CCL17 (TARC), CCL18 (PARC), CCL19 (MIP-3b), CCL2 (MCP-1), MCAF, CCL20 (MIP-3a), CCL21 (MTP-2), SLC, exodus-2, CCL22 (MDC/STC-I), CCL23 (MPIF-1), CCL24 (MPIF-2/eotaxin-2), CCL25 (TECK), CCL26 (eotaxin-3), CCL27 (CTACK/ILC), CCL28, CCL3 (MTP-la), CCL4 (MDP-1b), CCL5 (RANTES), CCL7 (MCP-3), CCL8 (mcp-2), CCNAI, CCNA2, CCNDI, CCNEI, CCNE2, CCRI (CKRI/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TERI/CKR-LI), CCR9 (GPR-9-6), CCRLI (VSHKI), CCRL2 (L-CCR), CD164, CD19, CD105, CDIC, CD20, CD200, CD22, CD24, CD28, CD3, CD33, CD37, CD38, CD3E, CD3G, CD3Z, CD4, CD40, CD40L, CD44, CD47, CD45RB, CD52, CD56, CD69, CD70, CD72, CD73, CD74, CD79A, CD79B, CD8, CD80, CD81, CD83, CD86, CDHI (E-cadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDK-NIA (p21Wapl/Cipl), CDKNIB (p27Kipl), CDKNIC, CDKN2A (P16INK4a), CDKN2B, CDKN2C, CDKN3, CEA, CEBPB, CERI, CHGA, CHGB, chitinase, CHST10, CKLFSF2, CKLFSF3, CKLFSF4, CKLFSF5, CKLFSF6, CKLFSF7, CKLFSF8, CLDN3, CLDN7, Claudin18.2, CLN3, CLU (clusterin), c-Met, CMKLRI, CMKORI (RDCI), CNRI, COL18A1, COLIAI, COL4A3, COL6A1, CR2, Cripto, CRP, CSFI (M-CSF), CSF2 (GM-CSF), CSF3 (GCSF), CTGF, CTLA4, CTNNBI (b-catenin), CTSB (cathepsin B), CX3CL1 (SCYDI), CX3CR1 (V28), CXCLI (GROI), CXCL10 (IP-10), CXCLII (1-TAC/IP-9), CXCL12 (SDFI), CXCL13, CXCL14, CXCL16, CXCL2, (GR02), CXCL3 (GR03), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCI, CYSLTRI, DAB2IP, DES, DKFZp451J0118, DNCLI, DPP4, E2F1, ECGFI, EDGI, EFNAI, EFNA3, EFNB2, EGF, EGFR, ELAC2, ENG, EN01, EN02, EN03, EpCAM, EPHB4, EPO, ERBB2 (Her-2), ERBB3 (Her-3), ERBB4 (Her-4), EREG, ERK8, ESRI, ESR2, F3 (TF), FADD, FasL, FASN, FCERIA, FCER2, FCGR3A, FGF, FGFI (aFGF), FGF10, FGF11, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FELI (EPSILON), FILI (ZETA), FLJ12584, FLJ25530, FLRTI (fibronectin), FLTI, FOS, FOSLI (FRA-I), FY (DARC), G250, GABRP (GABAa), GAGEBI, GAGECI, GALNAC4S-6ST, GAT A3, GDF5, GFI 1, GGT1, GM-CSF, GNASI, GNRHI, GPR2 (CCRIO), GPR31, GPR44, GPR81 (FKSG80), GRCCIO (CIO), GRP, GPNMB, GSN (villin), GSTPI, HAVCR2, HDAC4, HDAC5, HDAC7A, HDAC9, HGF, HIFIA, HDPI, histamine and histamine receptors, HLA-A, HLA-DRA, HM74, HMOXI, HUMCYT2A, ICEBERG, ICOSL, ID2, IFN-α, IFNAI, IFNA2, IFNA4, IFNA5, IFNA6, IFNA7, IFNB1, IFNγ, DFNWI, IGBPI, IGFI, IGFIR, IGF2, IGFBP2, IGFBP3, IGFBP6, IL-I, IL10, MORA, IL10RB, IL11, IL11RA, IL-12, IL12A, IL12B, IL12RB1, IL12RB2, IL13, IL13RA1, IL13RA2, IL14, IL15, IL15RA, IL16, IL17, IL17B, IL17C, IL17R, IL18, IL18BP, IL18R1, IL18RAP, IL19, IL1A, IL1B, ILIF10, IL1F5, IL1F6, IL1F7, IL1F8, IL1F9, IL1HYI, IL1R1, IL1R2, IL1RAP, IL1RAPL1, IL1RAPL2, IL1RL1, IL1RL2, ILIRN, IL2, IL20, IL20RA, IL21R, IL22, IL22R, IL22RA2, IL23, IL24, IL25, IL26, IL27, IL28A, IL28B, IL29, IL2RA, IL2RB, IL2RG, IL3, IL30, IL3RA, IL4, IL4R, IL5, IL5RA, IL6, IL6R, IL6ST (glycoprotein 130), EL7, EL7R, EL8, EphA2, IL8RA, DL8RB, IL8RB, DL9, DL9R, DLK, INHA, INHBA, INSL3, INSL4, IRAKI, Integrin, ERAK2, ITGAI, ITGA2, ITGA3, ITGA6 (a6 integrin), ITGAV, ITGB3, ITGB4 (b4 integrin), JAGI, JAKI, JAK3, JUN, K6HF, KAN, KDR, KITLG, KLF5 (GC Box BP), KLF6, KLKIO, KLK12, KLK13, KLK14, KLK15, KLK3, KLK4, KLK5, KLK6, KLK9, KRT1, KRT19 (keratin19), KRT2A, KHTHB6 (hair-specific type H keratin), LAG3, LAMAS, LEP (leptin), Lewis Y, Lingo-p75, Lingo-Troy, LPS, LTA (TNF-b), LTB, LTB4R (GPR16), LTB4R2, LTBR, MACMARCKS, MAG or Omgp, MAP2K7 (c-Jun), MDK, Mesothelin, MIBI, MUCl, midkine, MIEF, MIP-2, MKI67, (Ki-67), MMP2, MMP9, MS4A1, MSMB, MT3 (metallothionectin-111), MTSSI, MUCI (mucin), MYC, MYD88, NCK2, neurocan, NFKBI, NFKB2, NGFB (NGF), NGFR, NgR-Lingo, NgR-Nogo66 (Nogo), NgR-p75, NgR-Troy, NMEI (NM23A), NOX5, NPPB, NROBI, NR0B2, NRIDI, NR1D2, NR1H2, NR1H3, NR1H4, NR112, NR113, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRPI, NRP2, NT5E, NTN4, ODZI, OPRDI, P2RX7, PAP, PARTI, PATE, PAWR, PCA3, PCNA, PCSK9, PD-1, PD-L1, PDGFA, PDGFB, PECAMI, PF4(CXCL4), PGF, PGR, phosphacan, PIAS2, PIK3CG, PLAU (uPA), PLG, PLXDCI, PPBP (CXCL7), PPID, PRI, PRKCQ, PRKDI, PRL, PROC, PROK2, PSAP, PSCA, PSMA, PTAFR, PTEN, PTGS2 (COX-2), PTN, RAC2 (p21Rac2), RARB, RGSI, RGS13, RGS3, RNFIIO (ZNF144), ROB02, S100A2, SCGB1D2 (lipophilinB), SCGB2A1 (mammaglobin 2), SCGB2A2 (mamnnaglobin 1), SCYEI (endothelial monocyte-activating cytokine), SDF2, SERPINAI, SERPINA3, SERP1NB5 (maspin), SERPINEI (PAI-I), SERPDMF1, SHBG, SLA2, SLC2A2, SLC33A1, SLC43A1, SLC44A4, SLIT2, SOST, SPPI, SPRRIB (Sprl), ST6GAL1, STABI, STAT6, STEAP, STEAP2, TB4R2, TBX21, TCPIO, TDGFI, TEK, TGFA, TGFBI, TGFBIII, TGFB2, TGFB3, TGFBI, TGFBRI, TGFBR2, TGFBR3, THIL, THBSI (thrombospondin-1), THBS2, THBS4, THPO, TIE (Tie-1), TIGHT, Tenascin-C, TMP3, tissue factor, TLRIO, TLR2, TLR3, TLR4, TLR5, TLR6, TLR7, TLR8, TLR9, TNF, TNF-a, TNFAEP2 (B94), TNFAIP3, TNFRSFIIA, TNFRSFIA, TNFRSFIB, TNFRSF21, TNFRSF5, TNFRSF6 (Fas), TNFRSF7, TNFRSF8, TNFRSF9, TNFSFIO (TRAIL), TNFSFI 1 (TRANCE), TNFSF12 (AP03L), TNFSF13 (April), TNFSF13B, TNFSF14 (HVEM-L), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase Ea), TP53, TPMI, TPM2, TRADD, TRAFI, TRAF2, TRAF3, TRAF4, TRAF5, TRAF6, TREMI, TREM2, TRPC6, TSLP, TWEAK, VEGF, VEGFB, VEGFC, VEGFR, versican, VHL C5, VLA-4, XCLI (lymphotactin), XCL2 (SCM-1b), XCRI (GPR5/CCXCRI), YYI, ZFPM2 and thrombin.

Illustratively, the antibody is selected from the group consisting of trastuzumab, pertuzumab, nimotuzumab, enoblituzumab, emibetuzumab, inotuzumab, pinatuzumab, brentuximab, gemtuzumab, bivatuzumab, lorvotuzumab, cBR96, glematumamab and an anti-Claudin18.2 antibody, wherein the heavy chain of the anti-Claudin18.2 antibody is set forth in SEQ ID NO: 49, and the light chain is set forth in SEQ ID NO: 47.

"Conservative modification" or "conservative replacement or substitution" refers to replacement of amino acids in a protein with other amino acids having similar characteristics (e.g., charge, side-chain size, hydrophobicity/hydrophilicity, or backbone conformation and rigidity), so that changes can be frequently made without changing the biological activity of the protein. Those skilled in the art know that, generally speaking, a single amino acid replacement in a non-essential region of a polypeptide does not substantially change the biological activity (see, e.g., Watson et al. (1987) *Molecular Biology of the Gene*, The Benjamin/Cummings Pub. Co., p224, (4th edition)). In addition, the replacement of amino acids with similar structure or function is unlikely to disrupt the biological activity. Exemplary conservative substitutions are set forth below.

TABLE 1

Amino acid conservative substitutions

| Original residue | Conservative substitution |
|---|---|
| Ala (A) | Gly; Ser |
| Arg (R) | Lys; His |
| Asn (N) | Gln; His; Asp |
| Asp (D) | Glu; Asn |
| Cys (C) | Ser; Ala; Val |
| Gln (Q) | Asn; Glu |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |

TABLE 1-continued

| Amino acid conservative substitutions | |
|---|---|
| Original residue | Conservative substitution |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The term "terminal extension ratio" described herein refers to the ratio of expression products having a terminal extension sequence among an expression product population. Expression products having a terminal extension sequence are variants of the expression product of interest; they comprise the sequence of interest and other amino acid residues attached thereto as well. Illustratively, in an antibody light chain expression product, the terminal extension ratio of the expression product is 1% if 1% of the light chain sequence variants have other amino acid residues attached at the N-terminus. When the expression product population contains an expression product having a terminal extension sequence, it means that the expression product population has terminal heterogeneity. Illustratively, the terminal extension sequences in the present disclosure are derived from the residue of signal peptide amino acids.

The composition of the present disclosure comprises a desired expression product of interest and an expression product having a terminal extension sequence. The presence of amino-terminal extension in the composition can be detected by a variety of analytical techniques, including but not limited to, N-terminal sequence analysis, assays for charge heterogeneity (e.g., cation exchange chromatography or capillary zone electrophoresis), mass spectrometry, peptide mapping assay, and the like. The amount of the antibody variant in the composition generally ranges from an amount that constitutes the lower detection limit of any assay (e.g., cation exchange analysis) used to detect the variant to an amount less than the amount of the main species antibody. About 3% or less (e.g., about 3%, 2.5%, 2%, 1.5%, 1%, 0.5% or 0%) of the antibody light chains or antibody heavy chains in the composition comprise an amino-terminal extension. Such percentages can be determined by mass spectrometry or peptide mapping assay. When the proportion of the heterologous polypeptides containing the terminal extension exceeds 1% of the total amount of the sample, the heterologous polypeptides can be effectively identified based on peptide mapping assay, and simultaneously, the corresponding peak in the mass spectrogram for molecular weight after reduction is quantitatively identified.

The details of one or more embodiments of the present disclosure are set forth in the specification above. Although any methods and materials similar or identical to those described herein can be used in the practice or testing of the present disclosure, the methods and materials are described below. Other features, objects and advantages of the present disclosure will be apparent from the specification and the claims. In the specification and claims, singular forms include plural referents unless otherwise indicated clearly in the context. Unless otherwise defined, all technical and scientific terms used herein have the meanings generally understood by those of ordinary skill in the art to which the present disclosure belongs. All the patents and publications cited in the specification are incorporated by reference. The following examples are set forth to more fully illustrate the optional embodiments of the present disclosure. These examples should not be construed in any way as limiting the scope of the present disclosure, which is defined by the claims.

EXAMPLES

The present disclosure is further described with reference to the following examples, which, however, do not limit the scope of the present disclosure. The experimental methods in the examples of the present disclosure in which specific conditions are not specified are generally performed under conventional conditions such as Antibodies: A Laboratory Manual and Molecular Cloning: A Laboratory Manual by Cold Spring Harbor Laboratory, or under conditions recommended by the manufacturers of the starting materials or commercial products. Reagents without specific origins indicated are commercially available conventional reagents.

Example 1: Preparation of Anti-Claudin18.2 Antibody

Example 1-1: Construction of Cell Strain Highly Expressing Claudin18.2 pCDH-hClaudin18.2 lentiviral expression vector plasmids, pVSV-G and pCMV-dR8.91 lentiviral system packaging vectors were transfected into viral packaging cells 293T using Lipofectamine 3000 transfection reagent. The medium supernatant containing viruses was collected, filtered and centrifuged at ultra-high speed. The human gastric signet ring cell carcinoma cell strain NUGC4 was infected with the concentrated virus, screened using puromycin for two to three weeks and then subjected to FACS single-cell sorting.

Claudin18.2 expression levels were determined according to tumor IHC scores. Cells with a Claudin18.2 expression level similar to that of a tumor with a tumor IHC score of 3 points were considered cells with high expression, and cells with a Claudin18.2 expression level similar to that of a tumor with a tumor IHC score of 2 points were considered cells with moderate expression. According to the Claudin18.2 expression levels on the surface of NUGC4 cells infected by lentivirus determined by FACS, NUGC4/hClaudin18.2 monoclonal cell strains with high Claudin18.2 expression were selected. At the same time, the Claudin18.2 expression level on the surface of wild-type NUGC4 cells were also determined by FACS, and NUGC4 clonal cell strains with moderate Claudin18.2 expression were selected. The wild-type NUGC4 cells were cells with low Claudin18.2 expression.

The selected monoclonal cell strains were expanded and preserved by freezing for subsequent experiments.

```
]Sequence of Claudin18.2, Genbank NP_001002026:
                                        (SEQ ID NO: 1)
MAVTACQGLGFVVSLIGIAGIIAATCMDQWSTQDLYNNPVTAVFNYQGLW

RSCVRESSGFTECRGYFTLLGLPAMLQAVRALMIVGIVLGAIGLLVSIFA

LKCIRIGSMEDSAKANMTLTSGIMFIVSGLCAIAGVSVFANMLVTNFWMS

TANMYTGMGGMVQTVQTRYTFGAALFVGWVAGGLTLIGGVMMCIACRGLA

PEETNYKAVSYHASGHSVAYKPGGFKASTGFGSNTKNKKIYDGGARTEDE

VQSYPSKHDYV.

DNA sequence of Claudin18.2:
                                        (SEQ ID NO: 2)
  1 AGAATTGCGC TGTCCACTTG TCGTGTGGCT CTGTGTCGAC

    ACTGTGCGCC ACCATGGCCG

 61 TGACTGCCTG TCAGGGCTTG GGGTTCGTGG TTTCACTGAT

    TGGGATTGCG GGCATCATTG
```

-continued

```
121 CTGCCACCTG CATGGACCAG TGGAGCACCC AAGACTTGTA
    CAACAACCCC GTAACAGCTG
181 TTTTCAACTA CCAGGGGCTG TGGCGCTCCT GTGTCCGAGA
    GAGCTCTGGC TTCACCGAGT
241 GCCGGGGCTA CTTCACCCTG CTGGGGCTGC CAGCCATGCT
    GCAGGCAGTG CGAGCCCTGA
301 TGATCGTAGG CATCGTCCTG GGTGCCATTG GCCTCCTGGT
    ATCCATCTTT GCCCTGAAAT
361 GCATCCGCAT TGGCAGCATG GAGGACTCTG CCAAAGCCAA
    CATGACACTG ACCTCCGGGA
421 TCATGTTCAT TGTCTCAGGT CTTTGTGCAA TTGCTGGAGT
    GTCTGTGTTT GCCAACATGC
481 TGGTGACTAA CTTCTGGATG TCCACAGCTA ACATGTACAC
    CGGCATGGGT GGGATGGTGC
541 AGACTGTTCA GACCAGGTAC ACATTTGGTG CGGCTCTGTT
    CGTGGGCTGG GTCGCTGGAG
601 GCCTCACACT AATTGGGGGT GTGATGATGT GCATCGCCTG
    CCGGGGCCTG GCACCAGAAG
661 AAACCAACTA CAAAGCCGTT TCTTATCATG CCTCAGGCCA
    CAGTGTTGCC TACAAGCCTG
721 GAGGCTTCAA GGCCAGCACT GGCTTTGGGT CCAACACCAA
    AAACAAGAAG ATATACGATG
781 GAGGTGCCCG CACAGAGGAC GAGGTACAAT CTTATCCTTC
    CAAGCACGAC TATGTGTAAT
841 GCTCTAAGAC CTCTCAGCAC GGGCGGAAGA AACTCCCGGA
    GAGCTCACCC AAAAAACAAG
901 GAGATCCCAT CTAGATTTCT TCTTGCTTTT GACTCACAGC
    TGGAAGTTAG AAAAGCCTCG
961 ATTTCATCTT TGGAGAGGCC AAATGGTCTT AGCCTCAGTC
    TCTGTCTCTA AATATTCCAC
1021 CATAAAACAG CTGAGTTATT TATGAATTAG AGGCTATAGC
     TCACATTTTC AATCCTCTAT
1081 TTCTTTTTTT AAATATAACT TTCTACTCTG ATGAGAGAAT
     GTGGTTTTAA TCTCTCTCTC
1141 ACATTTTGAT GATTTAGACA GACTCCCCCT CTTCCTCCTA
     GTCAATAAAC CCATTGATGA
1201 TCTATTTCCC AGCTTATCCC CAAGAAAACT TTTGAAAGGA
     AAGAGTAGAC CCAAAGATGT
1261 TATTTTCTGC TGTTTGAATT TTGTCTCCCC ACCCCCAACT
     TGGCTAGTAA TAAACACTTA
```

-continued

```
1321 CTGAAGAAGA AGCAATAAGA GAAAGATATT TGTAATCTCT
     CCAGCCCATG ATCTCGGTTT
1381 TCTTACACTG TGATCTTAAA AGTTACCAAA CCAAAGTCAT
     TTTCAGTTTG AGGCAACCAA
1441 ACCTTTCTAC TGCTGTTGAC ATCTTCTTAT TACAGCAACA
     CCATTCTAGG AGTTTCCTGA
1501 GCTCTCCACT GGAGTCCTCT TTCTGTCGCG GGTCAGAAAT
     TGTCCCTAGA
1561 AATTATTTTT TTTAATTTAA GTCCTAAATA TAGTTAAAAT
     AAATAATGTT TTAGTAAAAT
1621 GATACACTAT CTCTGTGAAA TAGCCTCACC CCTACATGTG
     GATAGAAGGA AATGAAAAAA
1681 TAATTGCTTT GACATTGTCT ATATGGTACT TTGTAAAGTC
     ATGCTTAAGT ACAAATTCCA
1741 TGAAAAGCTC ACTGATCCTA ATTCTTTCCC TTTGAGGTCT
     CTATGGCTCT GATTGTACAT
1801 GATAGTAAGT GTAAGCCATG TAAAAAGTAA ATAATGTCTG
     GGCACAGTGG CTCACGCCTG
1861 TAATCCTAGC ACTTTGGGAG GCTGAGGAGG AAGGATCACT
     TGAGCCCAGA AGTTCGAGAC
1921 TAGCCTGGGC AACATGGAGA AGCCCTGTCT CTACAAAATA
     CAGAGAGAAA AAATCAGCCA
1981 GTCATGGTGG CCTACACCTG TAGTCCCAGC ATTCCGGGAG
     GCTGAGGTGG GAGGATCACT
2041 TGAGCCCAGG GAGGTTGGGG CTGCAGTGAG CCATGATCAC
     ACCACTGCAC TCCAGCCAGG
2101 TGACATAGCG AGATCCTGTC TAAAAAAATA AAAAATAAAT
     AATGGAACAC AGCAAGTCCT
2161 AGGAAGTAGG TTAAAACTAA TTCTTTAAAA AAAAAAAAAA
     GTTGAGCCTG AATTAAATGT
2221 AATGTTTCCA AGTGACAGGT ATCCACATTT GCATGGTTAC
     AAGCCACTGC CAGTTAGCAG
2281 TAGCACTTTC CTGGCACTGT GGTCGGTTTT GTTTTGTTTT
     GCTTTGTTTA GAGACGGGGT
2341 CTCACTTTCC AGGCTGGCCT CAAACTCCTG CACTCAAGCA
     ATTCTTCTAC CCTGGCCTCC
2401 CAAGTAGCTG GAATTACAGG TGTGCGCCAT CACAACTAGC
     TGGTGGTCAG TTTTGTTACT
2461 CTGAGAGCTG TTCACTTCTC TGAATTCACC TAGAGTGGTT
     GGACCATCAG ATGTTTGGGC
```

-continued

```
2521 AAAACTGAAA GCTCTTTGCA ACCACACACC TTCCCTGAGC
     TTACATCACT GCCCTTTTGA
2581 GCAGAAAGTC TAAATTCCTT CCAAGACAGT AGAATTCCAT
     CCCAGTACCA AAGCCAGATA
2641 GGCCCCCTAG GAAACTGAGG TAAGAGCAGT CTCTAAAAAC
     TACCCACAGC AGCATTGGTG
2701 CAGGGGAACT TGGCCATTAG GTTATTATTT GAGAGGAAAG
     TCCTCACATC AATAGTACAT
2761 ATGAAAGTGA CCTCCAAGGG GATTGGTGAA TACTCATAAG
     GATCTTCAGG CTGAACAGAC
2821 TATGTCTGGG GAAAGAACGG ATTATGCCCC ATTAAATAAC
     AAGTTGTGTT CAAGAGTCAG
2881 AGCAGTGAGC TCAGAGGCCC TTCTCACTGA GACAGCAACA
     TTTAAACCAA ACCAGAGGAA
2941 GTATTTGTGG AACTCACTGC CTCAGTTTGG GTAAAGGATG
     AGCAGACAAG TCAACTAAAG
3001 AAAAAAGAAA AGCAAGGAGG AGGGTTGAGC AATCTAGAGC
     ATGGAGTTTG TTAAGTGCTC
3061 TCTGGATTTG AGTTGAAGAG CATCCATTTG AGTTGAAGGC
     CACAGGGCAC AATGAGCTCT
3121 CCCTTCTACC ACCAGAAAGT CCCTGGTCAG GTCTCAGGTA
     GTGCGGTGTG GCTCAGCTGG
3181 GTTTTTAATT AGCGCATTCT CTATCCAACA TTTAATTGTT
     TGAAAGCCTC CATATAGTTA
3241 GATTGTGCTT TGTAATTTTG TTGTTGTTGC TCTATCTTAT
     TGTATATGCA TTGAGTATTA
3301 ACCTGAATGT TTTGTTACTT AAATATTAAA AACACTGTTA
     TCCTACAGTT
```

Example 1-2: Production of Anti-Human Claudin18.2 Monoclonal Antibody

1. Immunization

The anti-human Claudin18.2 monoclonal antibody was produced by immunizing mice.

Laboratory SJL white mice, female, 6-8 weeks of age (Beijing Vital River Laboratory Animal Technology Co., Ltd., animal production license number: SCXK(Beijing) 2012-0001). Feeding environment: SPF grade. The purchased mice are fed in a laboratory environment for 1 week, in a 12/12 hour light/dark cycle, at a temperature of 20-25° C., with humidity at 40-60%. The acclimatized mice were immunized according to the following scheme. The antigens for immunization were huClaudin18.2-HEK293 cells (a HEK-293 cell strain stably transfected with human Claudin18.2 plasmid).

Immunization scheme: Prior to the first cell immunization, each mouse was intraperitoneally (IP) injected with 0.1 mL of TiterMax® Gold Adjuvant (Sigma Cat No. T2684), and, a half hour later, with 0.1 mL of normal saline-diluted cellular fluid at a concentration of $1\times10^8$/mL. The cells were uniformly pipetted, and then inoculation was performed at days 0, 14, 28, 42 and 56. Blood was collected at days 21, 35, 49 and 63, and the antibody titer in mouse serum was determined by ELISA. After 4-5 immunizations, mice in which the antibody titer in serum was high and was reaching a plateau were selected for splenocyte fusion. The mice were immunized with a booster dose of $1\times10^7$ cells by intraperitoneal injection (IP) 3 days prior to splenocyte fusion.

2. Splenocyte Fusion

Spleen lymphocytes and myeloma cells, Sp2/0 cells (ATCC® CRL-8287™), were fused by following a PEG-mediated fusion procedure to obtain hybridoma cells. The hybridoma cells were resuspended in complete medium (IMDM medium containing 20% FBS, 1×HAT and 1×OPI) at a density of $0.5\text{-}1\times10^6$/mL and seeded in a 96-well plate at 100 μL/well. The plate was incubated at 37° C. with 5% $CO_2$ for 3-4 days, supplemented with HAT complete medium at 100 μL/well, and incubated for another 3-4 days to form clones. The supernatant was removed and HT complete medium (IMDM medium containing 20% FBS, 1× HT and 1×OPI) was added at 200 μL/well. The plate was incubated at 37° C. with 5% $CO_2$ for 3 days, followed by an ELISA assay.

3. Screening of Hybridoma Cells

The culture supernatants were assayed using a combined ELISA method according to the density the hybridoma cells were growing at. Cells that had good binding capacity to huClaudin18.2-HEK293 cells but were not bound to HEK293 were selected, expanded and frozen in time. Subcloning was performed two to three times to obtain single-cell clones.

A cell binding assay was performed for each cell subcloning. Hybridoma clones were obtained by the above screening process, and antibodies were further prepared using a serum-free cell culture method. The antibodies were purified for use in the test examples.

Example 1-3: Humanization of Murine Antibodies

Monoclonal hybridoma cell strains mAb1901 and mAb1902 with high in vitro activity were selected. The monoclonal antibody sequences therein were cloned, followed by humanization, recombinant expression and activity evaluation.

The cloning of a sequence from hybridoma is as follows. Hybridoma cells at logarithmic growth phase were harvested, and the RNA was extracted using Trizol (Invitrogen, 15596-018) (following the procedures in the kit instructions) and reverse transcribed (PrimeScript™ Reverse Transcriptase, Takara, cat #2680A). The cDNA obtained by reverse transcription was amplified by PCR using mouse Ig-Primer Set (Novagen, TB326 Rev.B 0503) and then sent for sequencing by a sequencing company. The amino acid sequences corresponding to the obtained DNA sequences are set forth in SEQ ID NOs: 3-6:

```
Murine heavy chain variable region of mAb1901
                                        (SEQ ID NO: 3)
EVQLMESGGGLVKPGGSLKLSCAASGFTFSDYGIHWVRQAPEMGLEWIAY
ISRGSSTIYYADTVKGRFTMSRDNAKNTLFLQMTSLRSEDTAMYYCARGG
YDTRNAMDYWGQGTSVTVSS.
```

-continued

[Murine light chain variable region of mAb1901 (SEQ ID NO: 4)

DIVMTQSPSSLSVSAGEKVTMSCKSSQSLLNSGNQKNYLAWYQQKPGQPP

KLLIYGASTRASGVPDRFTGSGSGTDFTLTISSVQAEDLAIYHCQNDLYY

PLTFGAGTKLELK.

Murine heavy chain variable region of mAb1902 (SEQ ID NO: 5)

EVQLQESGAELVKPGASVKLSCKASGYIFTSYWMHWVKQRPGQGLEWIGM

IHPNSGSTNYNEKFKGKATLTLDKSSSTAYMQLSSLPSEDSAVYYCARLK

TGNSFDYWGQGTTLTVSS.

Murine light chain variable region of mAb1902 (SEQ ID NO: 6)

DIVLTQSPSSLTVTAGEKVTMSCKSSQSLLNSGNQKNYLTWYQQKPGQPP

KLLIYWASTRESGVPDRFTGSGSGTDFTLTISSVQAEDLAIYYCQNAYTY

PFTFGSGTKLEIK.

The above murine heavy chain and light chain variable regions were linked to the heavy chain constant region of human IgG1 antibody and the human k light chain constant region described below, respectively, to form chimeric antibodies ch1901 and ch1902.

The constant regions were selected from the group consisting of the following sequences:

Heavy chain constant region of human IgG1 antibody: (SEQ ID NO: 7)

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

Human κ light chain constant region: (SEQ ID NO: 8)

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

Murine monoclonal antibodies are humanized according to methods disclosed in many publications in the art. Briefly, human constant domains were used in place of parent (murine antibody) constant domains, and human germline antibody sequences were selected, based on the homology of the murine and human antibodies, for CDR grafting. The present disclosure selects candidate molecules with good activity for humanization, and the results are as follows.

1. CDRs of Murine Antibodies

The amino acid residues of the VH/VL CDRs in Table 2 were identified using the Kabat numbering scheme and annotated.

The CDR sequences of the murine antibodies are described in Table 2:

TABLE 2

CDR sequences of murine antibodies

| Antibody | mAb1901 |
|---|---|
| HCDR1 | DYGIH (SEQ ID NO: 9) |
| HCDR2 | YISRGSSTIYYADTVKG (SEQ ID NO: 10) |
| HCDR3 | GGYDTRNAMDY (SEQ ID NO: 11) |
| LCDR1 | KSSQSLLNSGNQKNYLA (SEQ ID NO: 12) |
| LCDR2 | GASTRAS (SEQ ID NO: 13) |
| LCDR3 | QNDLYYPLT (SEQ ID NO: 14) |
| **Antibody** | **mAb1902** |
| HCDR1 | SYWMH (SEQ ID NO: 15 ) |
| HCDR2 | MIHPNSGSTNYNEKFKGR (SEQ ID NO: 16) |
| HCDR3 | LKTGNSFDY (SEQ ID NO: 17) |
| LCDR1 | KSSQSLLNSGNQKNYLT (SEQ ID NO: 18) |
| LCDR2 | WASTRES (SEQ ID NO: 19) |
| LCDR3 | QNAYTYPFT (SEQ ID NO: 20 ) |

2. Selection of Human Germline FR Region Sequences

Based on the typical structure of the murine antibody VH/VL CDR obtained, the heavy chain and light chain variable region sequences were compared with an antibody Germline database to obtain a human germline template with high homology. The human germline light chain framework region was derived from a human k light chain gene.

2.1. Humanization of mAb1901 and Reverse Mutation Design

A suitable human antibody germline was selected for humanization of mAb1901 murine antibody. The CDRs of murine antibody mAb1901 were grafted into the selected humanization template to obtain a humanized variable region (the sequence of the humanized heavy chain variable region was SEQ ID NO: 24, and the sequence of the light chain variable region was SEQ ID NO: 21), followed by recombination with an IgG constant region to form a complete antibody. Meanwhile, reverse mutations were introduced into the FR region in the V region of the humanized antibody. Exemplary reverse mutations and combinations thereof are as follows:

TABLE 3

Humanized antibody of mAb1901 and reverse mutations*

| Light chain variable regions of humanized antibody of mAb1901 | | Heavy chain variable regions of humanized antibody of mAb 1901 | |
|---|---|---|---|
| VL1 | None | VH1 | None |
| VL2 | N22S | VH2 | N82T |
| VL3 | N22S, V85I, Y87H | VH3 | V48I, N82T |
| | | VH4 | I69M, N82T |

*All amino acid positions in the table are numbered according to the Kabat numbering scheme; in N82T of the heavy chain variable region, 82 refers to position 82A according to the Kabat scheme.

TABLE 4

| Light chain and heavy chain variable region sequences of humanized antibody of mAb1901 | |
|---|---|
| Name of variable region (SEQ ID NO:) | Sequence |
| VL1<br>(SEQ ID NO: 21) | DIVMTQSPDSLAVSLGERATINCKSSQSLLNSGNQKNYLAWY<br>QQKPGQPPKLLIYGASTRASGVPDRFSGSGSGTDFTLTISSLQ<br>AEDVAVYYCQNDLYYPLTFGQGTKLEIK |
| VL2<br>(SEQ ID NO: 22) | DIVMTQSPDSLAVSLGERATISCKSSQSLLNSGNQKNYLAWY<br>QQKPGQPPKLLIYGASTRASGVPDRFSGSGSGTDFTLTISSLQ<br>AEDVAVYYCQNDLYYPLTFGQGTKLEIK |
| VL3<br>(SEQ ID NO: 23) | DIVMTQSPDSLAVSLGERATISCKSSQSLLNSGNQKNYLAWY<br>QQKPGQPPKLLIYGASTRASGVPDRFSGSGSGTDFTLTISSLQ<br>AEDVAIYHCQNDLYYPLTFGQGTKLEIK |
| VH1<br>(SEQ ID NO: 24) | EVQLVESGGGLVQPGGSLRLSCAASGFTFSDYGIHWVRQAP<br>GKGLEWVAYISRGSSTIYYADTVKGRFTISRDNAKNSLYLQM<br>NSLRAEDTAVYYCARGGYDTRNAMDYWGQGTTVTVSS |
| VH2<br>(SEQ ID NO: 25) | EVQLVESGGGLVQPGGSLRLSCAASGFTFSDYGIHWVRQAP<br>GKGLEWVAYISRGSSTIYYADTVKGRFTISRDNAKNSLYLQM<br>TSLRAEDTAVYYCARGGYDTRNAMDYWGQGTTVTVSS |
| VH3<br>(SEQ ID NO: 26) | EVQLVESGGGLVQPGGSLRLSCAASGFTFSDYGIHWVRQAP<br>GKGLEWIAYISRGSSTIYYADTVKGRFTISRDNAKNSLYLQM<br>TSLRAEDTAVYYCARGGYDTRNAMDYWGQGTTVTVSS |
| VH4<br>(SEQ ID NO: 27) | EVQLVESGGGLVQPGGSLRLSCAASGFTFSDYGIHWVRQAP<br>GKGLEWVAYISRGSSTIYYADTVKGRFTMSRDNAKNSLYLQ<br>MTSLRAEDTAVYYCARGGYDTRNAMDYWGQGTTVTVSS |

The corresponding heavy chain variable region in the table above could be linked to the human IgG1 heavy chain constant region set forth in SEQ ID NO: 7 to form a heavy chain of a full-length antibody, and the light chain variable region was linked to the human k light chain constant region set forth in SEQ ID NO: 8 to form a light chain of a full-length antibody. In other embodiments, the heavy chain variable region and the light chain variable region may also be linked to other heavy chain constant regions and light chain constant regions, respectively, to form a full-length antibody.

2.2. Humanization of mAb1902 and Reverse Mutation Design

A suitable human antibody germline was selected for humanization of mAb1902 murine antibody. The CDRs of murine antibody mAb1902 were grafted into the selected humanization template to obtain a humanized variable region (the sequence of the humanized heavy chain variable region was SEQ ID NO: 31, and the sequence of the light chain variable region was SEQ ID NO: 28), followed by recombination with an IgG constant region to form a complete antibody. Meanwhile, reverse mutations were introduced into the FR region in the V region of the humanized antibody. Exemplary reverse mutations and combinations thereof are as follows:

TABLE 5

| Humanized antibody of mAb1902 and reverse mutation design therefor* | | | |
|---|---|---|---|
| Light chain variable regions of humanized antibody of mAb1902 | | Heavy chain variable regions of humanized antibody of mAb1902 | |
| VL11 | None | VH11 | None |
| VL12 | M4L | VH12 | I69L, R71L, T73K |
| VL13 | M4L, N22S | VH13 | M48I, R66K, V67A, 169L, R71L, T73K |
| | | VH14 | R38K, A40R, M48I, R66K, V67A, 169L, R71L, T73K |

*All amino acid positions in the table are numbered according to the Kabat numbering scheme.

TABLE 6

| Light chain and heavy chain variable region sequences of humanized antibody of mAb1902 | |
|---|---|
| Name of variable region (SEQ ID NO:) | Sequence |
| VL11<br>(SEQ ID NO: 28) | DIVMTQSPDSLAVSLGERATINCKSSQSLLNSGNQKNYLTWYQQ<br>KPGQPPKLLIYWASTRESGVPDRFSGSGSGTDFTLTISSLQAEDVA<br>VYYCQNAYTYPFTFGQGTKLEIK |
| VL12<br>(SEQ ID NO: 29) | DIVLTQSPDSLAVSLGERATINCKSSQSLLNSGNQKNYLTWYQQK<br>PGQPPKLLIYWASTRESGVPDRFSGSGSGTDFTLTISSLQAEDVAV<br>YYCQNAYTYPFTFGQGTKLEIK |

TABLE 6-continued

Light chain and heavy chain variable region sequences of humanized antibody of mAb1902

| Name of variable region (SEQ ID NO:) | Sequence |
|---|---|
| VL13 (SEQ ID NO: 30) | DIVLTQSPDSLAVSLGERATISCKSSQSLLNSGNQKNYLTWYQQK PGQPPKLLIYWASTRESGVPDRFSGSGSGTDFTLTISSLQAEDVAV YYCQNAYTYPFTFGQGTKLEIK |
| VH11 (SEQ ID NO: 31) | EVQLVQSGAEVKKPGASVKVSCKASGYTFTSYWMHWVRQAPG QRLEWMGMIHPNSGSTNYNEKFKGRVTITRDTSASTAYMELSSL RSEDTAVYYCARLKTGNSFDYWGQGTTVTVSS |
| VH12 (SEQ ID NO: 32) | EVQLVQSGAEVKKPGASVKVSCKASGYTFTSYWMHWVRQAPG QRLEWMGMIHPNSGSTNYNEKFKGRVTLTLDKSASTAYMELSSL RSEDTAVYYCARLKTGNSFDYWGQGTTVTVSS |
| VH13 (SEQ ID NO: 33) | EVQLVQSGAEVKKPGASVKVSCKASGYTFTSYWMHWVRQAPG QRLEWIGMIHPNSGSTNYNEKFKGKATLTLDKSASTAYMELSSL RSEDTAVYYCARLKTGNSFDYWGQGTTVTVSS |
| VH14 (SEQ ID NO: 34) | EVQLVQSGAEVKKPGASVKVSCKASGYTFTSYWMHWVKQRPG QRLEWIGMIHPNSGSTNYNEKFKGKATLTLDKSASTAYMELSSL RSEDTAVYYCARLKTGNSFDYWGQGTTVTVSS |

The corresponding heavy chain variable region in the table above was linked to the human IgG1 heavy chain constant region set forth in SEQ ID NO: 7 to form a heavy chain of a full-length antibody, and the light chain variable region was linked to the human k light chain constant region set forth in SEQ ID NO: 8 to form a light chain of a full-length antibody.

Illustratively, the full-length sequences of the antibodies are as follows: Chimeric antibody ch1901:

Chimeric antibody ch1901:
Heavy chain of ch1901:

(SEQ ID NO: 35)

EVQLMESGGGLVKPGGSLKLSCAASGFTFSDYGIHWVRQAPEMGLEWIA

YISRGSSTIYYADTVKGRFTMSRDNAKNTLFLQMTSLRSEDTAMYYCAR

GGYDTRNAMDYWGQGTSVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK.

Light chain of ch1901:

(SEQ ID NO: 36)

DIVMTQSPSSLSVSAGEKVTMSCKSSQSLLNSGNQKNYLAWYQQKPGQP

PKLLIYGASTRASGVPDRFTGSGSGTDFTLTISSVQAEDLAIYHCQNDL

YYPLTFGAGTKLELKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC.

-continued

Chimeric antibody ch1902:
Heavy chain of ch1902

(SEQ ID NO: 37)

EVQLQESGAELVKPGASVKLSCKASGYIFTSYWMHWVKQRPGQGLEWIG

MIHPNSGSTNYNEKFKGKATLTLDKSSSTAYMQLSSLPSEDSAVYYCAR

LKTGNSFDYWGQGTTLTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK.

Light chain of ch1902

(SEQ ID NO: 38)

DIVLTQSPSSLTVTAGEKVTMSCKSSQSLLNSGNQKNYLTWYQQKPGQP

PKLLIYWASTRESGVPDRFTGSGSGTDFTLTISSVQAEDLAIYYCQNAY

TYPFTFGSGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC.

TABLE 7

Humanized antibodies of mAb1901

| | Heavy chain | | | |
|---|---|---|---|---|
| Light chain | H1 | H2 | H3 | H4 |
| L1 | h1901-1 | h1901-2 | h1901-3 | h1901-4 |
| L2 | h1901-5 | h1901-6 | h1901-7 | h1901-8 |
| L3 | h1901-9 | h1901-10 | h1901-11 | h1901-12 |

The light chain and heavy chain sequences of the full-length antibodies are as follows:

TABLE 8

Light chain and heavy chain sequences of humanized antibodies of mAb1901

| Name of light/ heavy chain (SEQ ID NO:) | Sequence |
|---|---|
| LI (SEQ ID NO: 39) | DIVMTQSPDSLAVSLGERATINCKSSQSLLNSGNQKNYLAWYQQ KPGQPPKLLIYGASTRASGVPDRFSGSGSGTDFTLTISSLQAEDVA VYYCQNDLYYPLTFGQGTKLEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| L2 (SEQ ID NO: 40) | DIVMTQSPDSLAVSLGERATISCKSSQSLLNSGNQKNYLAWYQQK PGQPPKLLIYGASTRASGVPDRFSGSGSGTDFTLTISSLQAEDVAV YYCQNDLYYPLTFGQGTKLEIKRTVAAPSVFIFPPSDEQLKSGTAS VVCLLNNFYPREAKVQWKVDNALQSGNSQESVTEQDSKDSTYS LSSTLTLSKADYEKHKVYACEVTHQGLSSPVTKSFNRGEC |
| L3 (SEQ ID NO: 41) | DIVMTQSPDSLAVSLGERATISCKSSQSLLNSGNQKNYLAWYQQK PGQPPKLLIYGASTRASGVPDRFSGSGSGTDFTLTISSLQAEDVAIY HCQNDLYYPLTFGQGTKLEIKRTVAAPSVFIFPPSDEQLKSGTASV VCLLNNFYPREAKVQWKVDNALQSGNSQESVTEQDSKDSTYSL SSTLTLSKADYEKHKVYACEVTHQGLSSPVTKSFNRGEC |
| H1 (SEQ ID NO: 42) | EVQLVESGGGLVQPGGSLRLSCAASGFTFSDYGIHWVRQAPGKG LEWVAYISRGSSTIYYADTVKGRFTISRDNAKNSLYLQMNSLRAE DTAVYYCARGGYDTRNAMDYWGQGTTVTVSSASTKGPSVFPLA PSSKSTSGGTAALGCLVKDYFPEPVTVSWNSGALTSGVHTFPAVL QSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALPAPIEKTISKAKGQPREPQVYTLP PSRDELTKNQVSLTCLVKGFYPSDIAVEWESNGQPENNYKTTPPV LDSDGSFFLYSKLTVDKSRWQQGNVFSCSVMHEALHNHYTQKSL SLSPGK |
| H2 (SEQ ID NO: 43) | EVQLVESGGGLVQPGGSLRLSCAASGFTFSDYGIHWVRQAPGKG LEWVAYISRGSSTIYYADTVKGRFTISRDNAKNSLYLQMTSLRAE DTAVYYCARGGYDTRNAMDYWGQGTTVTVSSASTKGPSVFPLA PSSKSTSGGTAALGCLVKDYFPEPVTVSWNSGALTSGVHTFPAVL QSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALPAPIEKTISKAKGQPREPQVYTLP PSRDELTKNQVSLTCLVKGFYPSDIAVEWESNGQPENNYKTTPPV LDSDGSFFLYSKLTVDKSRWQQGNVFSCSVMHEALHNHYTQKSL SLSPGK |
| H3 (SEQ ID NO: 44) | EVQLVESGGGLVQPGGSLRLSCAASGFTFSDYGIHWVRQAPGKG LEWIAYISRGSSTIYYADTVKGRFTISRDNAKNSLYLQMTSLRAED TAVYYCARGGYDTRNAMDYWGQGTTVTVSSASTKGPSVFPLAP SSKSTSGGTAALGCLVKDYFPEPVTVSWNSGALTSGVHTFPAVLQ SSGLYSLSSVVTVPSSSLGTQTYICNVNHKPSNTKVDKKVEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVL HQDWLNGKEYKCKVSNKALPAPIEKTISKAKGQPREPQVYTLPP SRDELTKNQVSLTCLVKGFYPSDIAVEWESNGQPENNYKTTPPVL DSDGSFFLYSKLTVDKSRWQQGNVFSCSVMHEALHNHYTQKSLS LSPGK |
| H4 (SEQ ID NO: 45) | EVQLVESGGGLVQPGGSLRLSCAASGFTFSDYGIHWVRQAPGKG LEWVAYISRGSSTIYYADTVKGRFTMSRDNAKNSLYLQMTSLRA EDTAVYYCARGGYDTRNAMDYWGQGTTVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPK SCDKTHTCPPCPAPELLGGPSVFLFPPKPKDTLMISRTPEVTCVVV DVSHEDPEVKFNWYVDGVEVHNAKTKPREEQYNSTYRVVSVLT VLHQDWLNGKEYKCKVSNKALPAPIEKTISKAKGQPREPQVYTL PPSRDELTKNQVSLTCLVKGFYPSDIAVEWESNGQPENNYKTTPP VLDSDGSFFLYSKLTVDKSRWQQGNVFSCSVMHEALHNHYTQK SLSLSPGK |

TABLE 9

| Humanized antibodies of mAb1902 | | | | |
|---|---|---|---|---|
| | Heavy chain | | | |
| Light chain | H11 | H12 | H13 | H14 |
| L11 | h1902-1 | h1902-2 | h1902-3 | h1902-4 |
| L12 | h1902-5 | h1902-6 | h1902-7 | h1902-8 |
| L13 | h1902-9 | h1902-10 | h1902-11 | h1902-12 |

The light chain and heavy chain sequences of the full-length antibodies are as follows:

TABLE 10

| Light chain and heavy chain sequences of humanized antibodies of mAb1902 | |
|---|---|
| Name of light/ heavy chain (SEQ ID NO:) | Sequence |
| L11 (SEQ ID NO: 46) | DIVMTQSPDSLAVSLGERATINCKSSQSLLNSGNQKNYLTWYQQKPG<br>QPPKLLIYWASTRESGVPDRFSGSGSGTDFTLTISSLQAEDVAVYYCQN<br>AYTYPFTFGQGTKLEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC |
| L12 (SEQ ID NO: 47) | DIVLTQSPDSLAVSLGERATINCKSSQSLLNSGNQKNYLTWYQQKPGQ<br>PPKLLIYWASTRESGVPDRFSGSGSGTDFTLTISSLQAEDVAVYYCQNA<br>YTYPFTFGQGTKLEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC |
| L13 (SEQ ID NO: 48) | DIVLTQSPDSLAVSLGERATISCKSSQSLLNSGNQKNYLTWYQQKPGQ<br>PPKLLIYWASTRESGVPDRFSGSGSGTDFTLTISSLQAEDVAVYYCQNA<br>YTYPFTFGQGTKLEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC |
| H11 (SEQ ID NO: 49) | EVQLVQSGAEVKKPGASVKVSCKASGYTFTSYWMHWVRQAPGQRL<br>EWMGMIHPNSGSTNYNEKFKGRVTITRDTSASTAYMELSSLRSEDTAV<br>YYCARLKTGNSFDYWGQGTTVTVSSASTKGPSVFPLAPSSKSTSGGT<br>AALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKAL<br>PAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSC<br>SVMHEALHNHYTQKSLSLSPGK |
| H12 (SEQ ID NO: 50) | EVQLVQSGAEVKKPGASVKVSCKASGYTFTSYWMHWVRQAPGQRL<br>EWMGMIHPNSGSTNYNEKFKGRVTLTLDKSASTAYMELSSLRSEDTA<br>VYYCARLKTGNSFDYWGQGTTVTVSSASTKGPSVFPLAPSSKSTSGG<br>TAALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAPEL<br>LGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNK<br>ALPAPIEKTISKAKGQPREPQVYTLPPSRDELTKNQVSLTCLVKGFYPS<br>DIAVEWESNGQPENNYKTTPPVLDSDGSFFLYSKLTVDKSRWQQGNV<br>FSCSVMHEALHNHYTQKSLSLSPGK |
| H13 (SEQ ID NO: 51) | EVQLVQSGAEVKKPGASVKVSCKASGYTFTSYWMHWVRQAPGQRL<br>EWIGMIHPNSGSTNYNEKFKGKATLTLDKSASTAYMELSSLRSEDTAV<br>YYCARLKTGNSFDYWGQGTTVTVSSASTKGPSVFPLAPSSKSTSGGT<br>AALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKAL<br>PAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSC<br>SVMHEALHNHYTQKSLSLSPGK |
| H14 (SEQ ID NO: 52) | EVQLVQSGAEVKKPGASVKVSCKASGYTFTSYWMHWVKQRPGQRL<br>EWIGMIHPNSGSTNYNEKFKGKATLTLDKSASTAYMELSSLRSEDTAV<br>YYCARLKTGNSFDYWGQGTTVTVSSASTKGPSVFPLAPSSKSTSGGT<br>AALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGV |

TABLE 10-continued

| Light chain and heavy chain sequences of humanized antibodies of mAb1902 | |
|---|---|
| Name of light/ heavy chain (SEQ ID NO:) | Sequence |
| | EVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSC SVMHEALHNHYTQKSLSLSPGK |

A positive control antibody of the present disclosure is IMAB-362 (from WO2016166122):

```
Heavy chain of IMAB-362
                                              (SEQ ID NO: 53)
  1 QVQLQQPGAELVRPGASVKL SCKASGYTFT SYWINWVKQR PGQGLEWIGN

 51 IYPSDSYTNY NQKFKDKATL TVDKSSSTAY MQLSSPTSED SAVYYCTRSW

101 RGNSFDYWGQ GTTLTVSSAS TKGPSVFPLA PSSKSTSGGT AALGCLVKDY

151 FPEPVTVSWN SGALTSGVHT FPAVLQSSGL YSLSSVVTVP SSSLGTQTYI

201 CNVNHKPSNT KVDKRVEPKS CDKTHTCPPC PAPELLGGPS VFLFPPKPKD

251 TLMISRTPEV TCVVVDVSHE DPEVKFNWYV DGVEVHNAKTKPREEQYNST

301 YRVVSVLTVL HQDWLNGKEY KCKVSNKALP APIEKTISKA KGQPREPQVY

351 TLPPSREEMT KNQVSLTCLV KGFYPSDIAV EWESNGQPEN NYKTTPPVLD

401 SDGSFFLYSK LTVDKSRWQQGNVFSCSVMHEALHNHYTQK SLSLSPGK.
```

```
Light chain of IMAB-362
                                              (SEQ ID NO: 54)
  1 DIVMTQSPSS LTVTAGEKVT MSCKSSQSLL NSGNQKNYLT WYQQKPGQPP

 51 KLLIYWASTR ESGVPDRFTG SGSGTDFTLT ISSVQAEDLA VYYCQNDYSY

101 PFTFGSGTKL EIKRTVAAPS VFIFPPSDEQ LKSGTASVVC LLNNFYPREA

151 KVQWKVDNAL QSGNSQESVT EQDSKDSTYS LSSTLTLSKA DYEKHKVYAC

201 EVTHQGLSSP VTKSFNRGEC.
```

The above antibodies were cloned, expressed and purified using conventional gene cloning and recombinant expression methods.

Test Example 1: Biological Evaluation of In Vitro Activity of Anti-Claudin18.2 Antibodies

Test Example 1-1: Cell-Level ELISA Binding Assay

Cell-based ELISA assay was used to detect the binding properties of the Claudin18.2 antibodies. The stably transfected Claudin18.2-expressing NUGC4 cells were cultured in a 96-well cell plate (Corning, 3599). When growing at 90% density, the cells were immobilized with 4% paraformaldehyde for 1 h. The plate was washed 3 times with PBST buffer (pH 7.4 PBS containing 0.05% TWEEN®-20 (polysorbate 20)), and a PBS-diluted 5% skim milk (powdered skim milk from Brightdairy) blocking solution was added at 200 μL/well. The plate was incubated in a 37° C. incubator for 2.5 h or was left to stand at 4° C. overnight (16-18 h) for blocking. After blocking, the blocking solution was removed. The plate was washed 3 times with the PBST buffer, and then a test antibody that was diluted with a sample diluent (pH 7.4 PBS containing 1% skim milk) to different concentrations was added at 50 μL/well. The plate was incubated in a 37° C. incubator for 2 h. After incubation, the plate was washed 5 times with PBST, and an HRP-labeled goat anti-human secondary antibody (Jackson Immuno Research, 109-035-003) that was diluted with the sample diluent was added at 100 μL/well. The plate was incubated at 37° C. for 1 h. The plate was washed 6 times with PBST, and then TMB chromogenic substrate (KPL, 52-00-03) was added at 50 μL/well. The plate was incubated at room temperature for 10-15 min, and the reaction was terminated by adding 1 M $H_2SO_4$ at 50 μL/well. The absorbance at 450 nm was read using an MD Versa Max TM microplate reader, and the binding $EC_{50}$ values of the Claudin18.2 antibodies to Claudin18.2 were calculated (the results are shown in the table below).

TABLE 11

| Binding activity of antibodies | | | |
|---|---|---|---|
| Antibody | IMAB362 | ch1901 | ch1902 |
| Emax | 1.175 | 1.399 | 1.272 |
| $EC_{50}$ (nM) | 0.108 | 0.098 | 0.074 |

TABLE 12-1

| Binding activity of humanized antibodies of mAb1901 | | |
|---|---|---|
| Antibody | Emax | $EC_{50}$ (nM) |
| IMAB362 | 1.115 | 0.086 |
| h1901-2 | 1.039 | 0.076 |
| h1901-3 | 1.1055 | 0.22 |
| h1901-4 | 0.986 | 0.201 |
| h1901-6 | 0.937 | 0.091 |
| h1901-7 | 0.921 | 0.166 |
| h1901-8 | 1.047 | 0.091 |
| h1901-11 | 1.44 | 0.076 |
| h1901-12 | 1.22 | 0.116 |

TABLE 12-2

| Binding activity of humanized antibodies of mAb1902 | | |
|---|---|---|
| Antibody | Emax | $EC_{50}$ (nM) |
| IMAB362 | 0.88 | 0.187 |
| h1902-1 | 0.87 | 0.113 |
| h1902-2 | 0.88 | 0.107 |
| h1902-3 | 0.84 | 0.175 |
| h1902-4 | 0.82 | 0.087 |
| h1902-5 | 0.9 | 0.098 |
| h1902-6 | 0.78 | 0.141 |
| h1902-7 | 0.75 | 0.121 |
| h1902-8 | 0.89 | 0.132 |
| h1902-9 | 0.75 | 0.137 |
| h1902-10 | 0.89 | 0.133 |

Test Example 1-2: Antibody Cell-Level Binding Assay

The stably transfected Claudin18.2-expressing NUGC4 cells were suspended in FACS buffer (2% fetal bovine serum (Gibco, 10099141) pH 7.4 PBS (Sigma, P4417-100TAB)) to obtain a $1\times10^6$/mL cell suspension, which was then added to a 96-well round-bottom plate (Corning, 3795) at 100 µL/well. After centrifugation and removal of the supernatant, the test Claudin18.2 antibody that was diluted with FACS buffer to different concentrations was added at 50 µL/well. The plate was incubated in the dark in a 4° C. refrigerator for 1 h. The plate was washed 3 times with FACS buffer by centrifugation at 300 g, and goat anti-human IgG coated with Alexa Fluor 488 (H+L) (invitrogen, A-11013) at working concentration was added. The plate was incubated in the dark in a 4° C. refrigerator for 40 min. The plate was washed 3 times with FACS buffer by centrifugation at 300 g and tested on a BD FACS CantoII flow cytometer for geometric mean fluorescence intensity. The binding $EC_{50}$ values of the Claudin18.2 antibodies to the stably transfected Claudin18.2-expressing NUGC4 cells were calculated. The results are shown in FIG. 1.

Test Example 1-3: Antibody Endocytosis Assay

Figure 2:
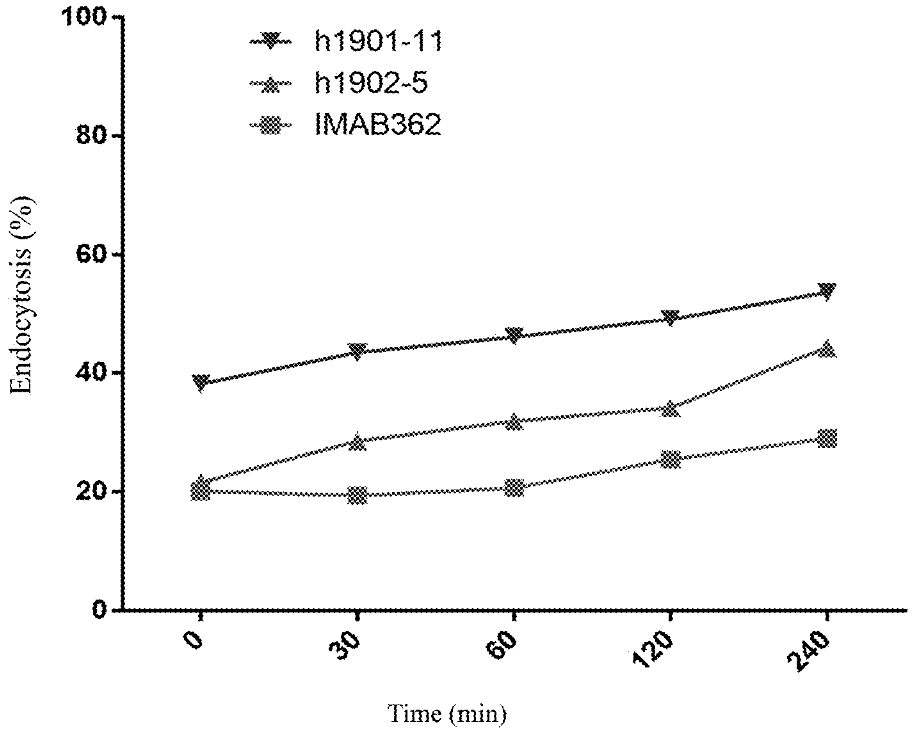
FIG. 2: endocytosis of humanized antibodies by NUGC4 cells.

A test Claudin18.2 antibody pre-labeled with DyLight 488 NHS Ester (thermofisher, 46403) was added to $1\times10^6$/mL stably transfected Claudin18.2-expressing NUGC4 cells at a final concentration of 5 µg/mL. The mixture was incubated in the dark on ice for 1 h and washed 3 times with pre-cooled FACS buffer (pH 7.4 PBS, 2% fetal bovine serum) by centrifugation. After removal of the supernatant, a pre-heated complete medium was added, followed by incubation in a 37° C. cell incubator with 5% $CO_2$. The cells were taken out after 0, 0.5, 1, 2 and 4 h and stored in the dark on ice. After all samples were collected, they were each centrifuged at 300 g at low temperature to remove the supernatant. An elution buffer (pH 1.7 0.05 M glycine, 0.1 M sodium chloride) was added, and then the mixture was incubated at room temperature for 7 min, washed once with FACS buffer by centrifugation at 300 g, and tested on a BD FACS CantoII flow cytometer for geometric mean fluorescence intensity. The efficiency of endocytosis of the Claudin18.2 antibodies by the stably transfected Claudin18.2-expressing NUGC4 cells was calculated. The results (see FIG. 2) show that the humanized antibodies have good endocytosis efficiency.

Test Example 1-4: Antibody Affinity Assay Based on Flow Cytometry

On the day of experiment, HEK293/hClaudin18.2 cells were collected into a U-bottomed 96-well plate at $1\times10^5$ to $2\times10^5$ cells per well. A human Claudin18.2 antibody that was 2× diluted serially (12 concentration points) from an initial concentration of 5 µg/mL was added, and the plate was incubated at 4° C. for 1 h. IMAB362 was used as a positive control, and a negative control with no antibody was also provided. The antibody was removed by centrifugation, and FITC anti-human IgG Fc antibody (200×) was added at 100 µL/well. The plate was incubated in the dark at 4° C. for 30 min and washed twice with PBS+2% FBS before flow cytometry analysis. BD FACS CantoII was started and preheated, and then the BD FACSDiva software was run to start a new experiment. The HEK293/hClaudin18.2 negative control sample was tested, and the FSC and SSC voltages were adjusted to appropriate values and saved. Blank sample B and standard curve 1 were tested according to the instructions for Quantum™ FITC-5 MESF Kit, and the FITC voltage was adjusted to an appropriate value and saved. The samples in the U-bottomed 96-well plate were tested at the saved voltage, and data were recorded. The experimental data were analyzed using Flowjo software to obtain a Geo mean, and an MESF-Geo Mean standard curve was fit according to the instructions for Quantum™ FITC-5 MESF Kit. The molar concentration of the human Claudin18.2 antibody bound to HEK293/hClaudin18.2 cells and the free antibody concentration were calculated according to the concentration fluorescence value of the FITC anti-human IgG Fc antibody, and the Bmax and the dissociation constant KD of the antibody were calculated through Scatchard plots. The results are shown in Table 13.

TABLE 13

| Cell-level affinity of humanized antibodies | | | |
|---|---|---|---|
| Antibody | IMAB362 | h1901-11 | h1902-5 |
| KD (nM) | 10.2 | 6.8 | 1.64 |

Test Example 1-5: Evaluation of ADCC Effect of Antibodies

A variety of NUGC4 cells (with high, moderate and low expression of Claudin18.2) were digested, centrifuged at 1000 rpm, resuspended, and counted. The cells were resuspended at a density of $3\times10^5$ cells/mL in phenol red-free RPMI 1640 (Gibco, 11835-030) supplemented with 10% FBS (New Zealand ultra-low IgG fetal bovine serum, Gibco, 1921005PJ). Cells were added to a 96-well plate (Corning, 3903) at 25 µL/well (7500 cells/well). An antibody was diluted into the phenol red-free medium to obtain a 3× antibody dilution, which was then added to the cell plate at 25 µL/well. The plate was incubated in a 37° C. incubator with 5% $CO_2$ for 0.5 h.

Effector cells (FcrR3A-V158-NFAT-RE-Jurkat cells) were harvested, centrifuged at 1000 rpm, resuspended, and counted. The cells were resuspended at a density of $3\times10^6$ cells/mL in phenol red-free RPMI 1640 supplemented with 10% FBS (New Zealand ultra-low IgG fetal bovine serum), and then were added to the plate at 25 μL/well ($7.5\times10^4$ cells/well). The plate was incubated in a 37° C. incubator with 5% $CO_2$ for 6 h.

Bright-Glo (Promega, E2610) was added to the plate at 75 μL/well, and the chemical luminescence was detected using a microplate reader (PerkinElmer, VITOR3).

Figure 3A:
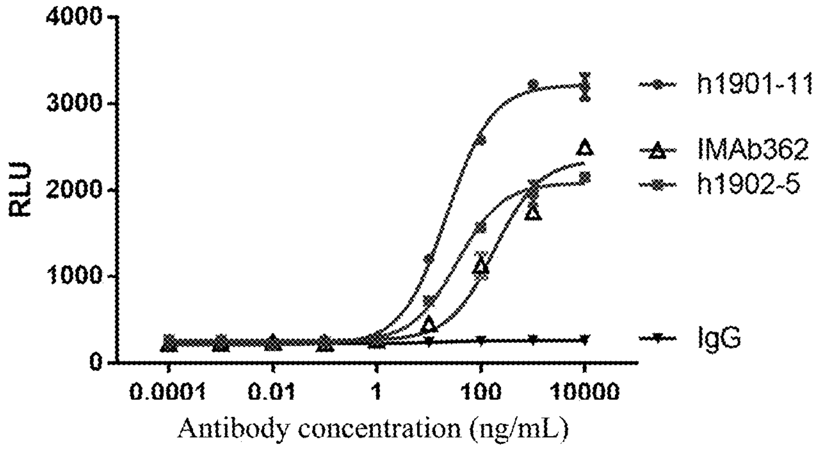
FIGS. 3A-3C: the detection of ADCC effect of antibodies in NUGC4 cells with varying expression levels of Claudin18.2.
Figure 3B:
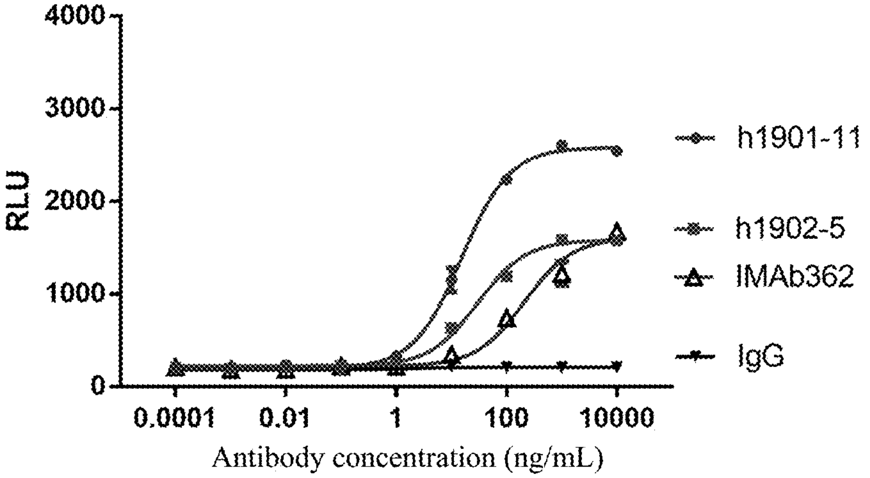
Figure 3C:
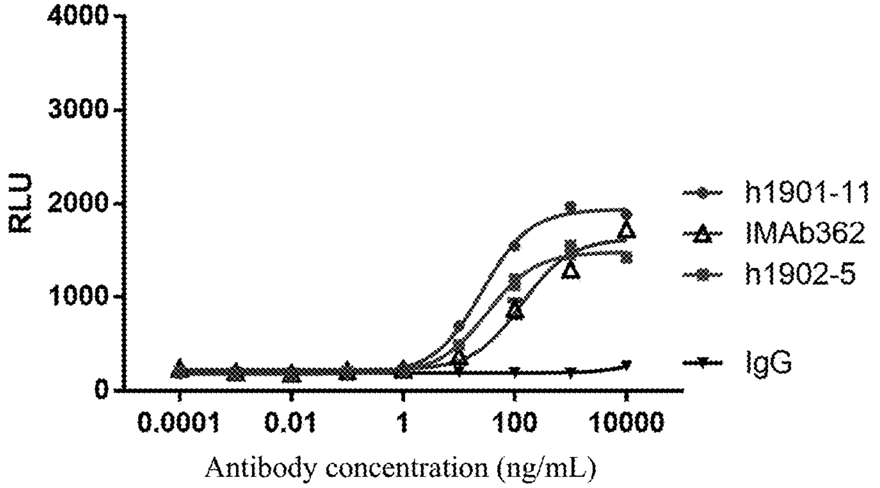
Figure 4A:
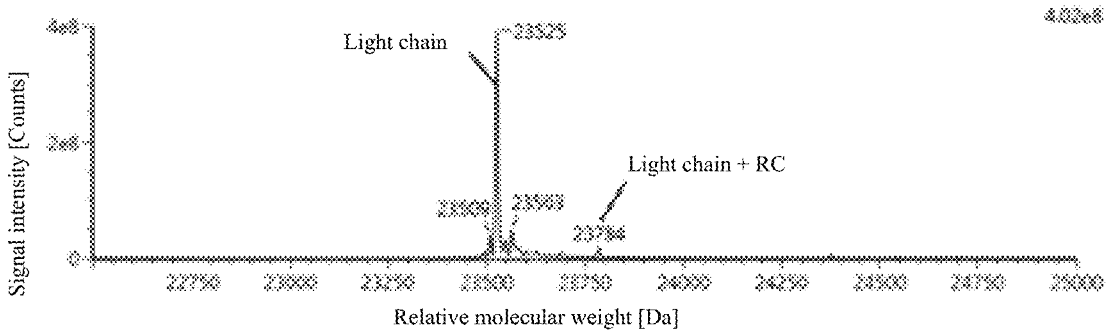
FIGS. 4A-4D.
Figure 4B:
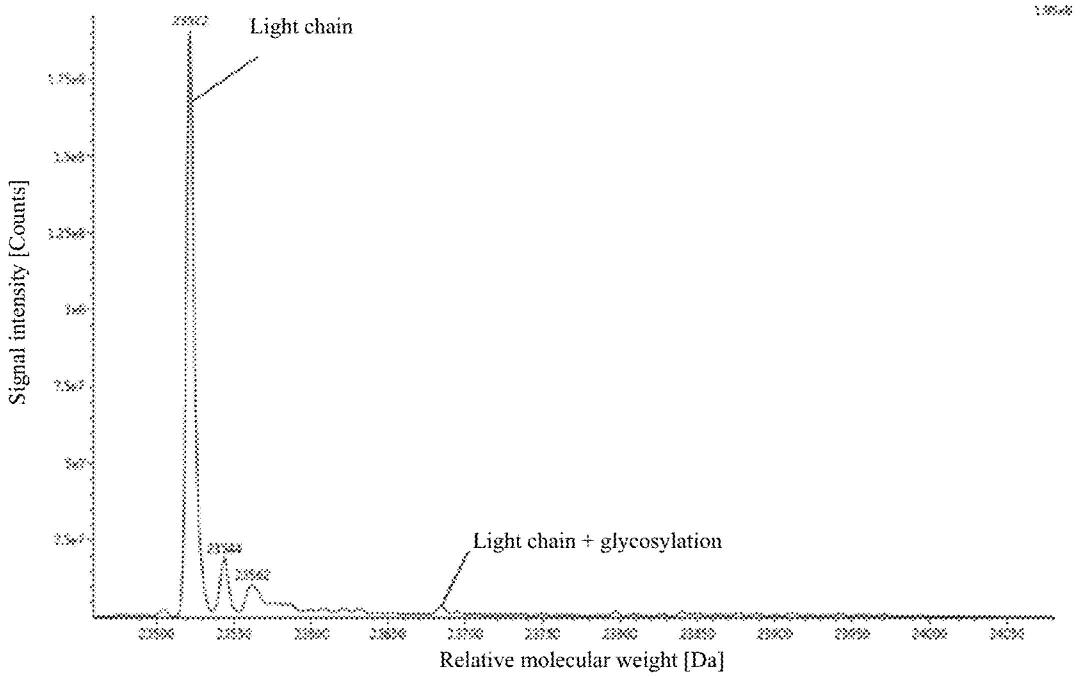
Figure 4C:
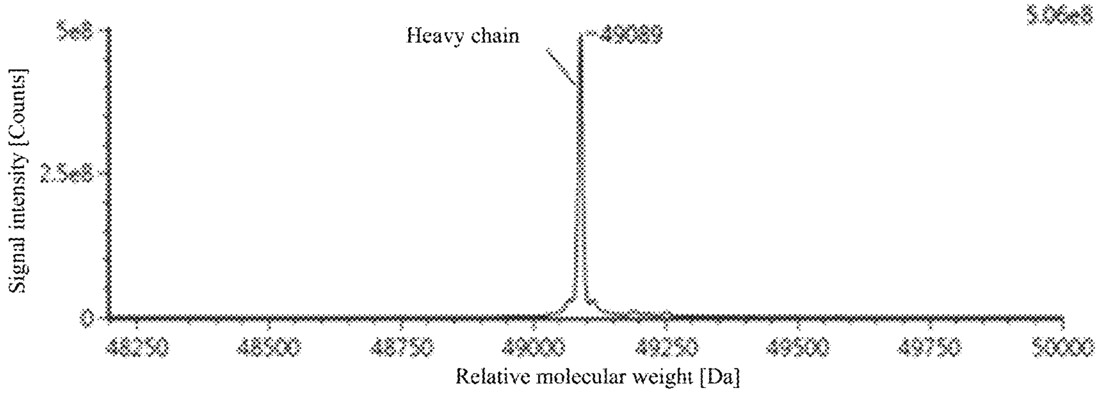
Figure 4D:
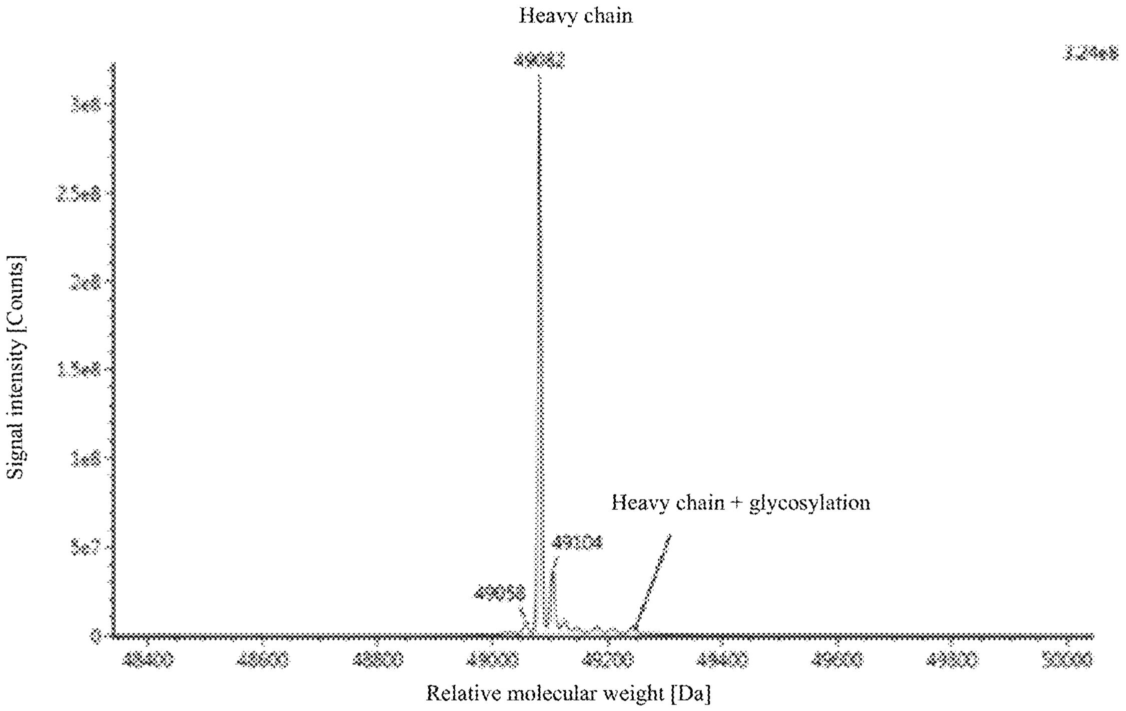
Figure 5A:
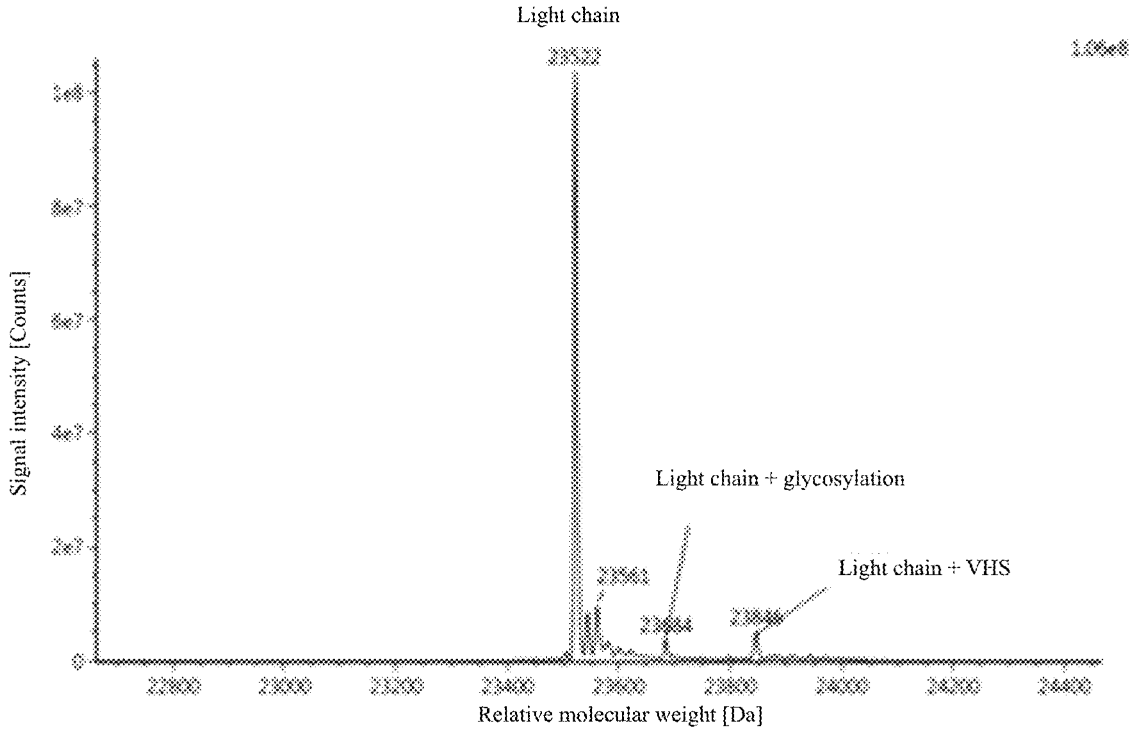
FIGS. 5A-5D.
Figure 5B:
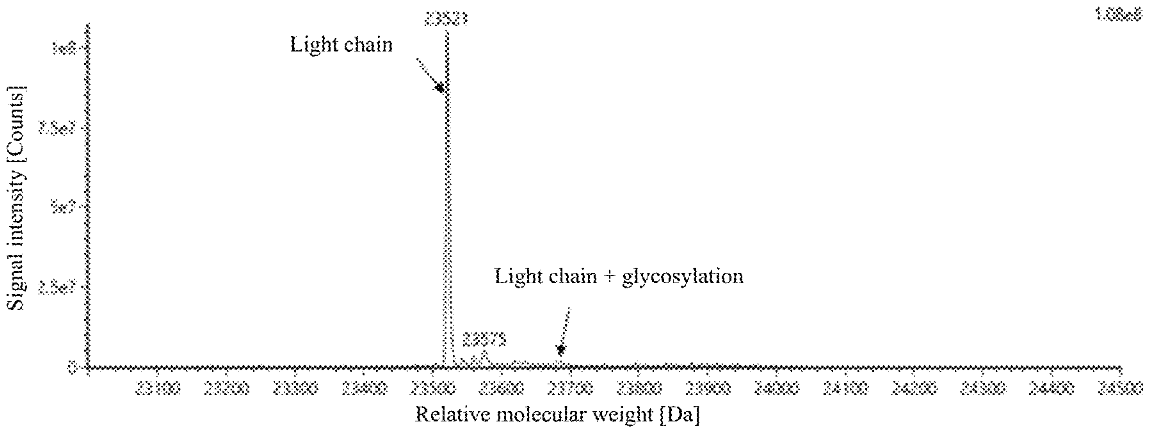
Figure 5C:
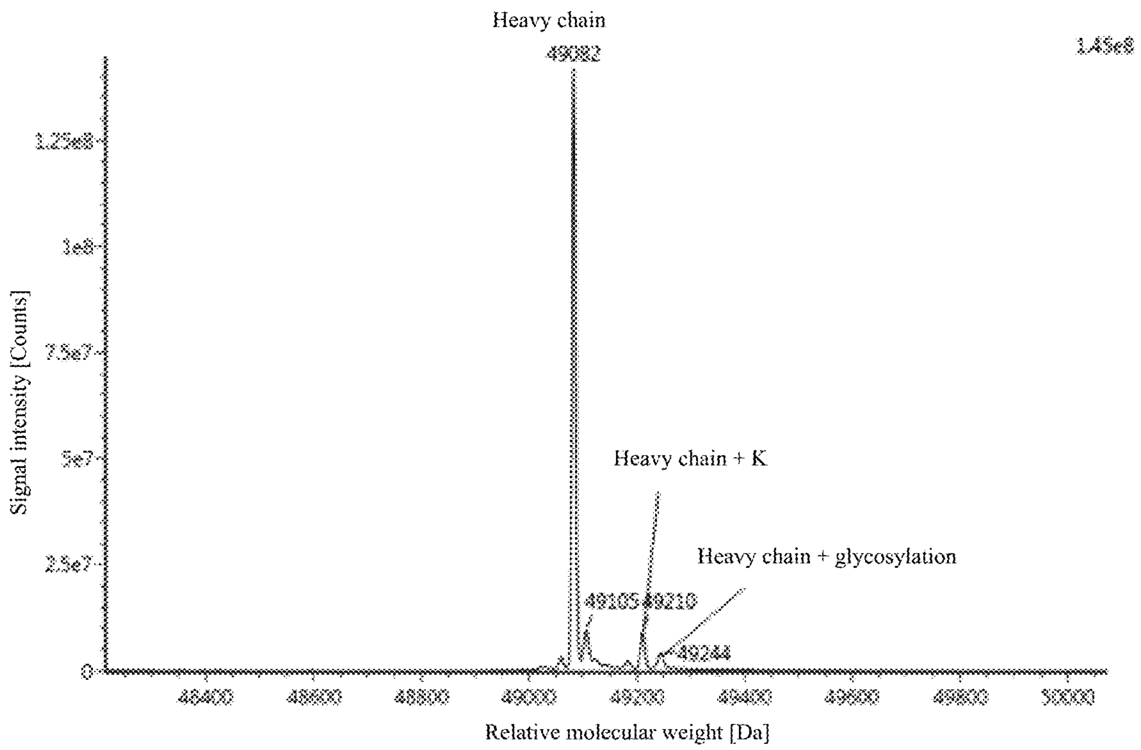
Figure 5D:
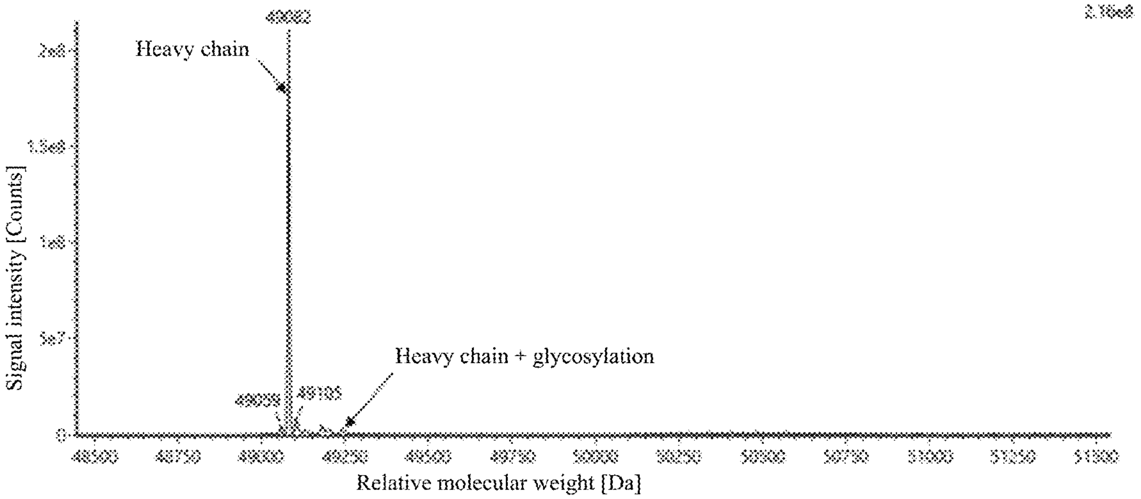
Figure 6A:
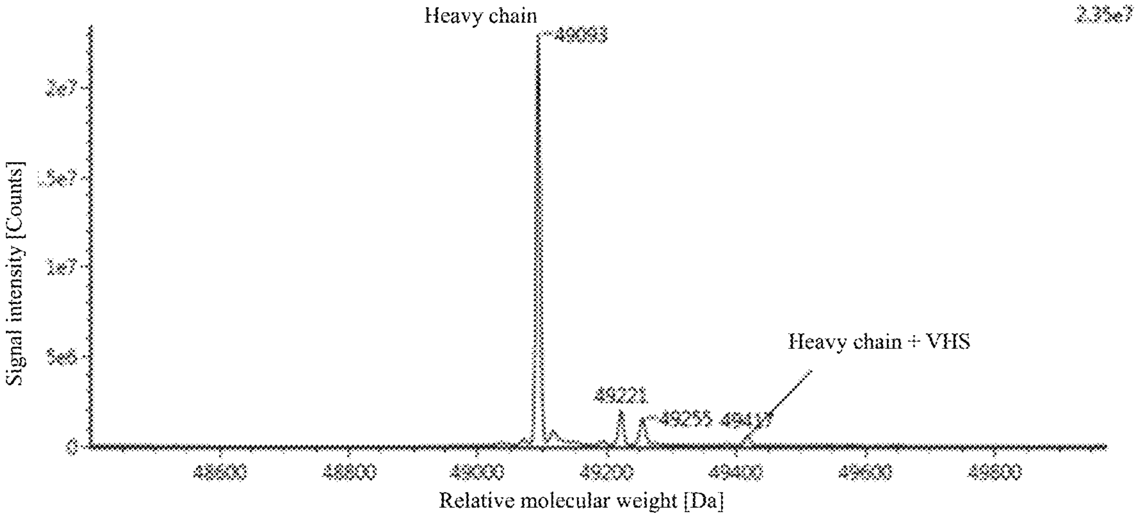
FIGS. 6A-6D.
Figure 6B:
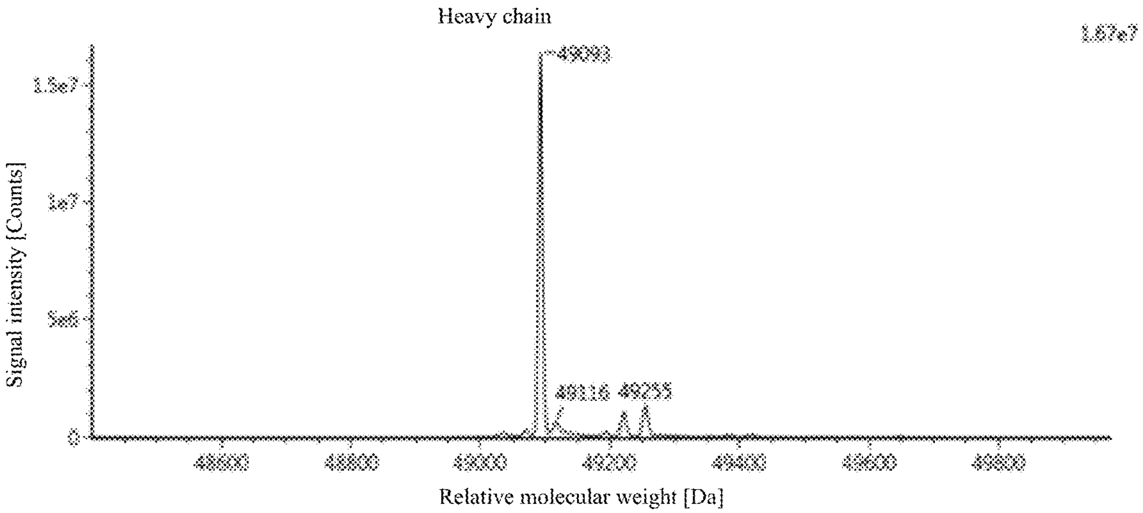
Figure 6C:
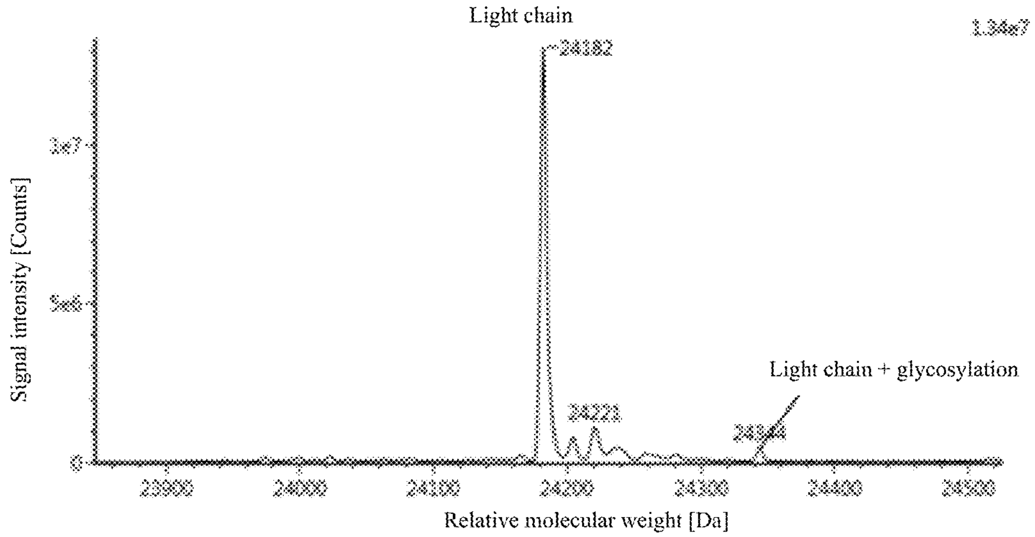
Figure 6D:
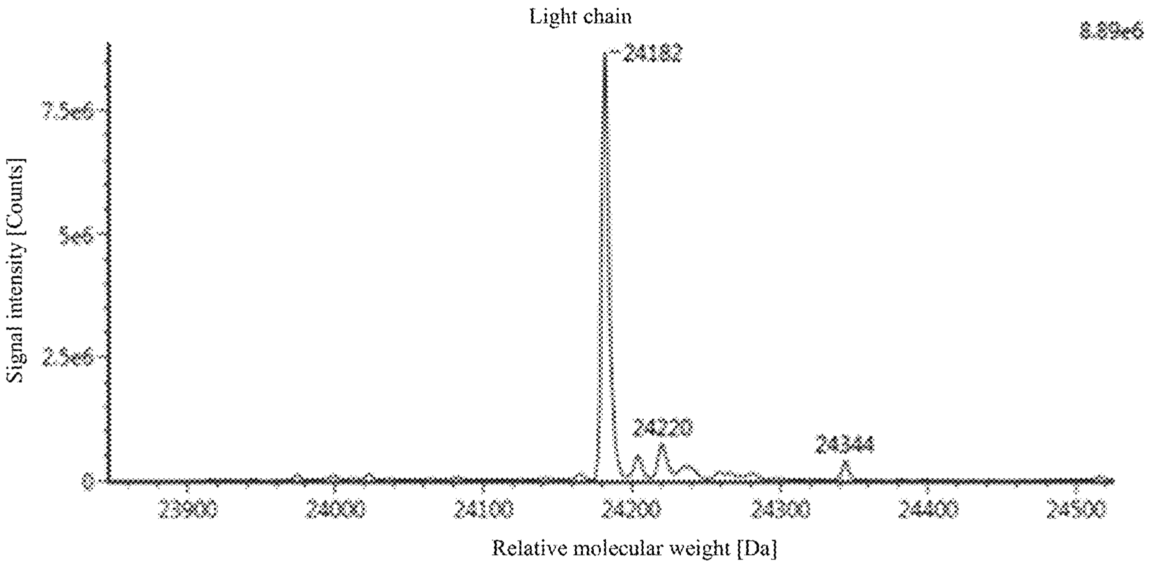
Figure 7A:
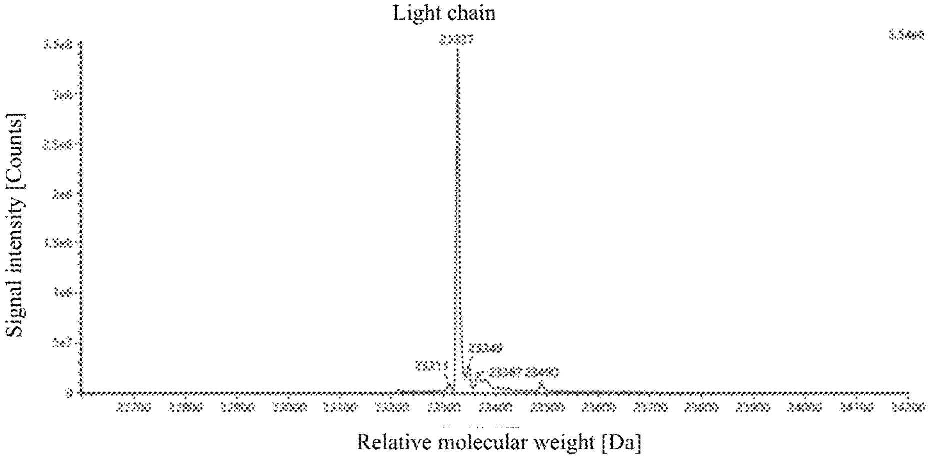
FIGS. 7A-7D.
Figure 7B:
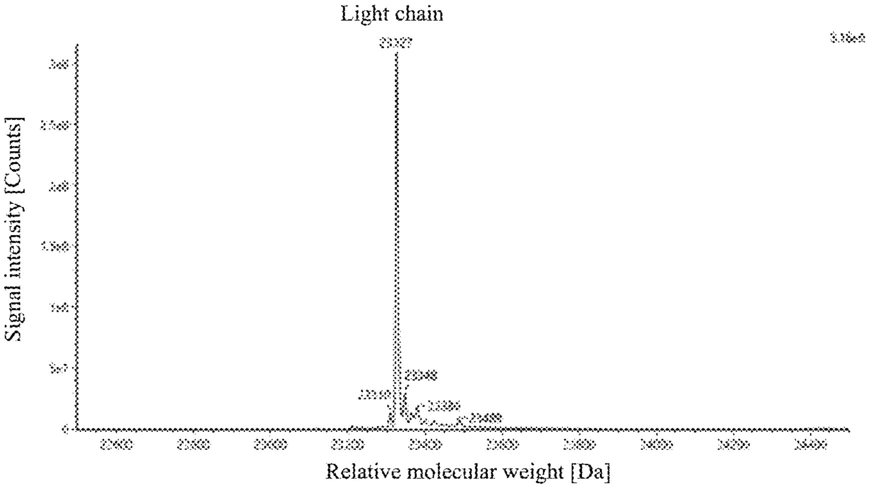
Figure 7C:
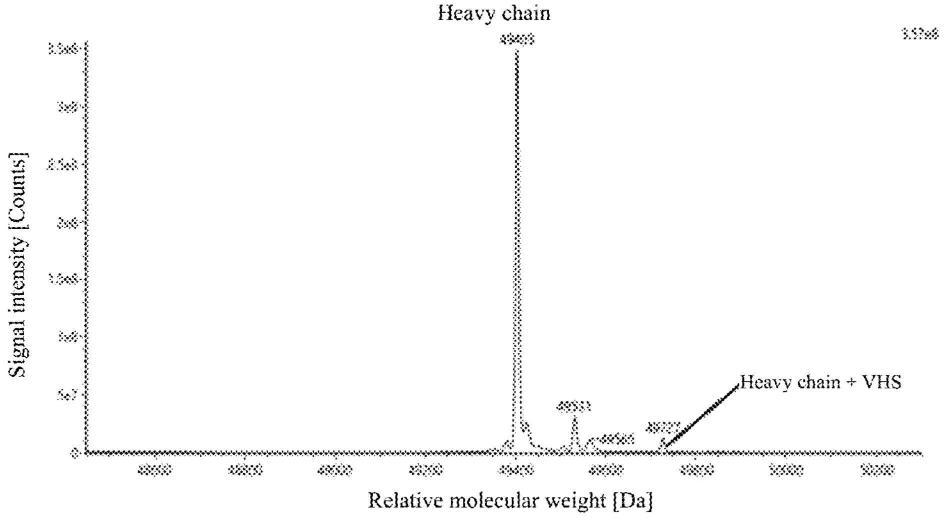
Figure 7D:
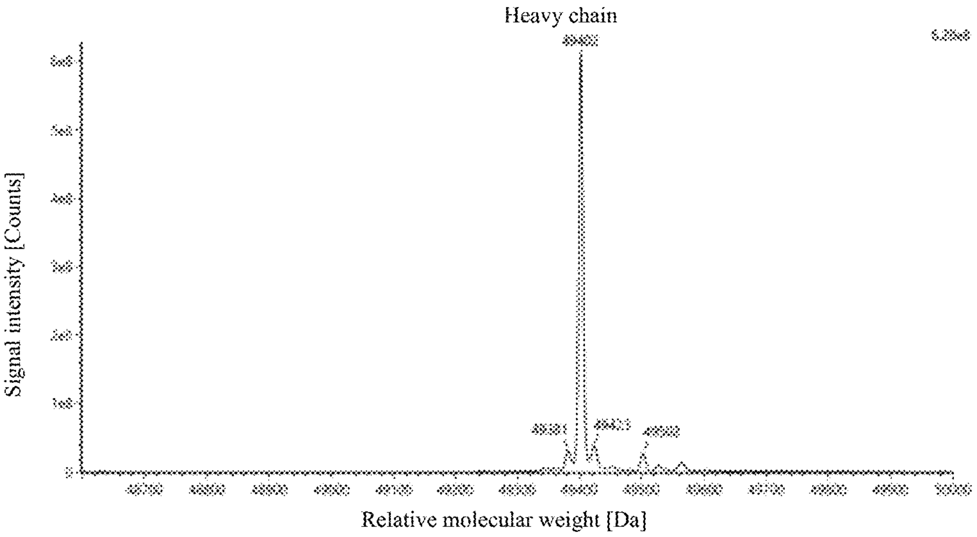

The results (see Table 14 and FIGS. 3A-3C) show that both antibodies h1901-11 and h1902-5 show high ADCC activity in the NUGC4 cells with low, moderate and high expression of Claudin18.2.

TABLE 14

ADCC effect of antibodies in NUGC4 cells with varying expression levels of Claudin 18.2

| Expression level of Claudin18.2 in NUGC4 | | h1901-11 | h1902-5 | IMAB362 |
|---|---|---|---|---|
| Low expression | IC50 (ng/ml) | 22.42 | 35.46 | 183.4 |
| Moderate expression | IC50 (ng/ml) | 15.35 | 30.00 | 210.4 |
| High expression | IC50 (ng/ml) | 26.17 | 32.16 | 132.6 |

Example 2: Design and Application of Signal Peptide

Example 2-1: Design and Expression of Pertuzumab Fused with Different Signal Peptides Antibodies fused with the following signal peptides were designed, and the combinations of signal peptide sequences are as follows:

1.
(SEQ ID NO: 152)
MEWSWVFLFFLSVTTGVHS
and

-continued (SEQ ID NO: 153)
MSVPTQVLGLLLLWLTDARC 2.
(SEQ ID NO: 152)
MEWSWVFLFFLSVTTGVHS
and (SEQ ID NO: 152)
MEWSWVFLFFLSVTTGVHS 3.
(SEQ ID NO: 57)
MEWSWVFLFFLSLTGVHA
and (SEQ ID NO: 105)
MSVPTQVLGLLLLWLTDVRA 4.
(SEQ ID NO: 57)
MEWSWVFLFFLSLTGVHA
and (SEQ ID NO: 57)
MEWSWVFLFFLSLTGVHA 5.
(SEQ ID NO: 105)
MSVPTQVLGLLLLWLTDVRA
and (SEQ ID NO: 57)
MEWSWVFLFFLSLTGVHA The signal peptides in each combination described above were placed at the amino acid N terminuses of the heavy chain and the light chain of the pertuzumab antibody, respectively, and corresponding new heavy chain and light chain sequences were designed. The designed sequences are as follows:

Amino acid sequence of pertuzumab-1 antibody heavy chain containing signal peptide
(SEQ ID NO: 154)
MEWSWVFLFFLSVTTGVHSEVQLVESGGGLVQPGGSLRLSCAASGFTFTDYTMDWVR
QAPGKGLEWVADVNPNSGGSIYNQRFKGRFTLSVDRSKNTLYLQMNSLRAEDTAVYY
CARNLGPSFYFDYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPG
K Amino acid sequence of pertuzumab-1 antibody light chain containing signal peptide
(SEQ ID NO: 155)
MSVPTQVLGLLLLWLTDARCDIQMTQSPSSLSASVGDRVTITCKASQDVSIGVAWYQQ
KPGKAPKLLIYSASYRYTGVPSRFSGSGSGTDFTLTISSLQPEDFATYYCQQYYTYPYTFG
QGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC -continued Amino acid sequence of pertuzumab-2 antibody heavy chain containing signal peptide (SEQ ID NO: 154)

Amino acid sequence of pertuzumab-2 antibody light chain containing signal peptide (SEQ ID NO: 156)

MEWSWVFLFFLSVTTGVHSDIQMTQSPSSLSASVGDRVTITCKASQDVSIGVAWYQQKP

GKAPKLLIYSASYRYTGVPSRFSGSGSGTDFTLTISSLQPEDFATYYCQQYYTYPYTFGQG

TKVEIKRTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGEC

Amino acid sequence of pertuzumab-3 antibody heavy chain containing signal peptide (SEQ ID NO: 157)

MEWSWVFLFFLSLTGVHAEVQLVESGGGLVQPGGSLRLSCAASGFTFTDYTMDWVRQA

PGKGLEWVADVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSLSPGK

Amino acid sequence of pertuzumab-3 antibody light chain containing signal peptide (SEQ ID NO: 158)

MSVPTQVLGLLLLWLTDVRADIQMTQSPSSLSASVGDRVTITCKASQDVSIGVAWYQQ

KPGKAPKLLIYSASYRYTGVPSRFSGSGSGTDFTLTISSLQPEDFATYYCQQYYTYPYTFG

QGTKVEIKRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNRGEC

Amino acid sequence of pertuzumab-4 antibody heavy chain containing signal peptide (SEQ ID NO: 157)

Amino acid sequence of pertuzumab-4 antibody light chain containing signal peptide (SEQ ID NO: 159)

MEWSWVFLFFLSLTGVHADIQMTQSPSSLSASVGDRVTITCKASQDVSIGVAWYQQKP

TKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

Amino acid sequence of pertuzumab-5 antibody heavy chain containing signal peptide (SEQ ID NO: 160)

MSVPTQVLGLLLLWLTDVRAEVQLVESGGGLVQPGGSLRLSCAASGFTFTDYTMDWV

RQAPGKGLEWVADVNPNSGGSIYNQRFKGRFTLSVDRSKNTLYLQMNSLRAEDTAVY

YCARNLGPSFYFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHYTQKSLSLSP

GK

-continued

Amino acid sequence of pertuzumab-5 antibody light chain containing signal peptide (SEQ ID NO: 159)

(Note: the underlined part is signal peptide)

Based on the sequences of the pertuzumab-1 to pertuzumab-4, gene segments of each heavy chain and each light chain were synthesized. The heavy chain genes were cloned into PXC18.4 to form heavy chain plasmids, and light chain genes were cloned into PXC17.4 to form light chain plasmids. The light chain plasmid was cloned into the heavy chain plasmid through the same enzymatic digestion sites in the plasmids, and a full-length antibody plasmid was constructed. The full-length antibody plasmid was directly transfected into CHO cells by electrotransfection, and stably transfected cells containing the plasmid were obtained after screening. The stably transfected cells were cultured, and the supernatant obtained after culturing was purified by a Protein A affinity column to obtain the expression product.

Example 2-2: Design and Expression of h1902-5 Fused with Different Signal Peptides Antibodies fused with the following signal peptides were designed, and the combinations of signal peptide sequences are as follows:

1.

(SEQ ID NO: 152)
MEWSWVFLFFLSVTTGVHS
and (SEQ ID NO: 152)
MEWSWVFLFFLSVTTGVHS

2.

(SEQ ID NO: 57)
MEWSWVFLFFLSLTGVHA
and (SEQ ID NO: 105)
MSVPTQVLGLLLLWLTDVRA

3.

(SEQ ID NO: 105)
MSVPTQVLGLLLLWLTDVRA
and (SEQ ID NO: 57)
MEWSWVFLFFLSLTGVHA
and The signal peptides in each combination described above were placed at the N terminuses of the heavy chain and the light chain of the h1902-5 antibody, respectively, and corresponding new heavy chain and light chain sequences were designed. The designed sequences are as follows:

Amino acid sequence of h1902-5-1 antibody heavy chain containing signal peptide (SEQ ID NO: 161)

MEWSWVFLFFLSVTTGVHSEVQLVQSGAEVKKPGASVKVSCKASGYTFTS

YWMHWVRQAPGQRLEWMGMIHPNSGSTNYNEKFKGRVTITRDTSASTAYM

ELSSLRSEDTAVYYCARLKTGNSFDYWGQGTTVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

-continued

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

Amino acid sequence of h1902-5-1 antibody light chain containing signal peptide (SEQ ID NO: 162)

MEWSWVFLFFLSVTTGVHSDIVLTQSPDSLAVSLGERATINCKSSQSLLN

SGNQKNYLTWYQQKPGQPPKLLIYWASTRESGVPDRFSGSGSGTDFTLTI

SSLQAEDVAVYYCQNAYTYPFTFGQGTKLEIKRTVAAPSVFIFPPSDEQL

KSGTASVVCLLNNFYPREAKVQWKVDNALQSGNSQESVTEQDSKDSTYSL

SSTLTLSKADYEKHKVYACEVTHQGLSSPVTKSFNRGEC

Amino acid sequence of h1902-5-2 antibody heavy chain containing signal peptide (SEQ ID NO: 163)

MEWSWVFLFFLSLTGVHAEVQLVQSGAEVKKPGASVKVSCKASGYTFTSY

WMHWVRQAPGQRLEWMGMIHPNSGSTNYNEKFKGRVTITRDTSASTAYME

LSSLRSEDTAVYYCARLKTGNSFDYWGQGTTVTVSSASTKGPSVFPLAPS

SKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK

Amino acid sequence of h1902-5-2 antibody light chain containing signal peptide (SEQ ID NO: 164)

MSVPTQVLGLLLLWLTDVRADIVLTQSPDSLAVSLGERATINCKSSQSLL

NSGNQKNYLTWYQQKPGQPPKLLIYWASTRESGVPDRFSGSGSGTDFTLT

ISSLQAEDVAVYYCQNAYTYPFTFGQGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC

Amino acid sequence of h1902-5-3 antibody heavy chain containing signal peptide (SEQ ID NO: 165)

MSVPTQVLGLLLLWLTDVRAEVQLVQSGAEVKKPGASVKVSCKASGYTFT

SYWMHWVRQAPGQRLEWMGMIHPNSGSTNYNEKFKGRVTITRDTSASTAY

MELSSLRSEDTAVYYCARLKTGNSFDYWGQGTTVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

-continued

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK

Amino acid sequence of h1902-5-3 antibody light chain containing signal peptide (SEQ ID NO: 166)

MEWSWVFLFFLSLTGVHADIVLTQSPDSLAVSLGERATINCKSSQSLLNS

GNQKNYLTWYQQKPGQPPKLLIYWASTRESGVPDRFSGSGSGTDFTLTIS

SLQAEDVAVYYCQNAYTYPFTFGQGTKLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC (Note: the underlined part is signal peptide)

Based on the sequences of the h1902-5-1 or h1902-5-2 described above, gene segments of each heavy chain and each light chain were synthesized and constructed on an expression vector to obtain a full-length antibody plasmid. The full-length antibody plasmid was directly transfected into CHO cells by electrotransfection, and stably transfected cells containing the plasmid were obtained after screening. The stably transfected cells were cultured, and the supernatant obtained after culturing was purified by a Protein A affinity column to obtain the expression product.

Example 2-3: Design and Expression of FcRn Fused with Different Signal Peptides Amino acid sequences of the heavy chain and the light chain of the anti-FcRn antibody are as follows:

Heavy chain (SEQ ID NO: 167)

EVQLVQSGAEVKKPGESLKISCKGSGYNFNKHYIAWVRQMPGKGLEWMGI

IYPDNSNTIYSPSFQGQVTISADKSISTAYLQWSSLKASDTAMYYCARFG

GPTFAQWYFDYWGQGTLVTVSSASTKGPSVFPLAPCSRSTSESTAALGCL

VKDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKPK

DTLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQV

YTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain (SEQ ID NO: 168)

NFMLTQPHSVSESPGKTVTISCTGSSGSIASNYVQWYQQRPGSSPTTVIY

EDNQRASGVPDRFSGSIDSSSNSASLTISGLKTEDEADYYCQSYDSSSHN

WVFGGGTKLTVLGQPKANPTVTLFPPSSEELQANKATLVCLISDFYPGAV

TVAWKADGSPVKAGVETTKPSKQSNNKYAASSYLSLTPEQWKSHRSYSCQ

VTHEGSTVEKTVAPTECS

Antibodies fused with the following signal peptides were designed, and the combinations of signal peptide sequences are as follows:

1.

(SEQ ID NO: 152)

MEWSWVFLFFLSVTTGVHS and (SEQ ID NO: 152)

MEWSWVFLFFLSVTTGVHS

2.

(SEQ ID NO: 57)

MEWSWVFLFFLSLTGVHA and (SEQ ID NO: 57)

MEWSWVFLFFLSLTGVHA

The designed sequences are as follows:

Amino acid sequence of FcRn-1 antibody heavy chain containingsignal peptide (SEQ ID NO: 169)

MEWSWVFLFFLSVTTGVHSEVQLVQSGAEVKKPGESLKISCKGSGYNFNK

HYIAWVRQMPGKGLEWMGIIYPDNSNTIYSPSFQGQVTISADKSISTAYL

QWSSLKASDTAMYYCARFGGPTFAQWYFDYWGQGTLVTVSSASTKGPSVF

PLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPC

PAPEFLGGPSVFLFPPKPKDTLMISRTPEVTCVVVDVSQEDPEVQFNWYV

DGVEVHNAKTKPREEQFNSTYRVVSVLTVLHQDWLNGKEYKCKVSNKGLP

SSIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVMH

EALHNHYTQKSLSLSLGK

Amino acid sequence of FcRn-1 antibody light chain containing signal peptide (SEQ ID NO: 170)

MEWSWVFLFFLSVTTGVHSNFMLTQPHSVSESPGKTVTISCTGSSGSIAS

NYVQWYQQRPGSSPTTVIYEDNQRASGVPDRFSGSIDSSSNSASLTISGL

KTEDEADYYCQSYDSSSHNWVFGGGTKLTVLGQPKANPTVTLFPPSSEEL

QANKATLVCLISDFYPGAVTVAWKADGSPVKAGVETTKPSKQSNNKYAAS

SYLSLTPEQWKSHRSYSCQVTHEGSTVEKTVAPTECS

Amino acid sequence of FcRn-2 antibody heavy chain containing signal peptide (SEQ ID NO: 171)

MEWSWVFLFFLSLTGVHAEVQLVQSGAEVKKPGESLKISCKGSGYNFNKH

YIAWVRQMPGKGLEWMGIIYPDNSNTIYSPSFQGQVTISADKSISTAYLQ

WSSLKASDTAMYYCARFGGPTFAQWYFDYWGQGTLVTVSSASTKGPSVFP

LAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCP

APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

-continued

SIEKTISKAKGQPREPQVYTLPPSQEEMTKNQVSLTCLVKGFYPSDIAVE

WESNGQPENNYKTTPPVLDSDGSFFLYSRLTVDKSRWQEGNVFSCSVMHE

ALHNHYTQKSLSLSLGK

Amino acid sequence of FcRn-2 antibody light chain containing signal peptide (SEQ ID NO: 172)

MEWSWVFLFFLSLTGVHANFMLTQPHSVSESPGKTVTISCTGSSGSIASN

YVQWYQQRPGSSPTTVIYEDNQRASGVPDRFSGSIDSSSNSASLTISGLK

TEDEADYYCQSYDSSSHNWVFGGGTKLTVLGQPKANPTVTLFPPSSEELQ

ANKATLVCLISDFYPGAVTVAWKADGSPVKAGVETTKPSKQSNNKYAASS

YLSLTPEQWKSHRSYSCQVTHEGSTVEKTVAPTECS

Based on the sequences of the FcRn-1 and FcRn-2 described above, gene segments of each heavy chain and each light chain were synthesized and constructed on an expression vector to obtain a full-length antibody plasmid. The full-length antibody plasmid was directly transfected into CHO cells by electrotransfection, and stably transfected cell pool containing the plasmid was obtained after screening. The stably transfected cell pool was cultured, and the supernatant obtained after culturing was purified by a Protein A affinity column to obtain the expression product.

Test Example 2: Terminal Heterogeneity of Expression Products with Different Signal Peptides

Test Example 2-1: Detection of Molecular Weight after Deglycosylation and Reduction and Amino Acid Sequence of Pertuzumab Fused with Different Signal Peptides N-glycosyl carried by pertuzumab-1, pertuzumab-2, pertuzumab-3 and pertuzumab-4 samples was cut off by PNGase F glycosidase (NEB, P0708), and then the samples were each reduced into light and heavy chains by DTT (Sigma, 43815). Finally, the molecular weight after deglycosylation and reduction of each sample was detected by LC-MS (Waters, ACQUITY UPLC H-Class/XeVo G2-XS QTOF), and data processing and analysis were performed using UNIFI software.

The detection results of pertuzumab-1 and pertuzumab-3 are shown in FIGS. 4A-4D: 4.7% signal peptide amino acid (RC) residue was detected in the light chain of the pertuzumab-1 sample, while the light chain of the pertuzumab-3 sample had no signal peptide amino acid residue. No signal peptide amino acid residue was detected in the heavy chains of both pertuzumab-1 and pertuzumab-3, and only a small amount of glycated modification was present. Pertuzumab-1 was subjected to urea denaturation, DTT was then added for reduction into light and heavy chains, and then Glu C enzyme (Promega, V1651) was added for enzymatic digestion. The molecular weight data of the resulting sample was collected by LC-MS and then analyzed using UNIFI software to obtain the amino acid sequence information of the sample.

The results showed that for pertuzumab-1, abnormal peaks that appeared in the detection of the molecular weight after deglycosylation and reduction were confirmed to be RC amino acid residue through peptide mapping analysis and verification. Specific results are shown in Table 15.

TABLE 15

Peptide mapping assay data of pertuzumab-1 light chain N-terminal signal peptide

| Sample | Terminal extension residue | Intensity | Theoretical molecular weight (Da) | Measured molecular weight (Da) | Retention time (min) |
|---|---|---|---|---|---|
| Pertuzumab-1 | None | 205984816 | 1878.8862 | 1878.8917 | 30.41 |
| | C | 20145608 | 2038.9168 | 2038.9145 | 30.17 |

Note: In this test example, Glu C enzyme is used for enzymatic digestion to cut off the amino acid R in the sequence RC, and the residual amino acid C indicates RC amino acid residue.

The detection results of pertuzumab-2 and pertuzumab-4 are shown in FIGS. 5A-5D: 5.8% signal peptide amino acid (VHS) residue was detected in the light chain of the pertuzumab-2 sample, while the light chain of the pertuzumab-4 sample had no signal peptide amino acid residue. No signal peptide amino acid residue was detected in the heavy chains of both antibodies, and only a small amount of glycated modification was present.

Pertuzumab-2 was subjected to urea denaturation, DTT was then added for reduction into light and heavy chains, and then Glu C enzyme was added for enzymatic digestion. The molecular weight data of the resulting sample was collected by LC-MS and then analyzed using UNIFI software to obtain the amino acid sequence information of the sample.

The results showed that for pertuzumab-2, abnormal peaks that appeared in the detection of the molecular weight after deglycosylation and reduction were confirmed to be VHS amino acid residue through peptide mapping analysis and verification. Specific results are shown in Table 16.

TABLE 16

Peptide mapping assay data of pertuzumab-1 light chain N-terminal signal peptide

| Sample | Terminal extension residue | Intensity | Theoretical molecular weight (Da) | Measured molecular weight (Da) | Retention time (min) |
|---|---|---|---|---|---|
| Pertuzumab-2 | None | 177359008 | 1878.8883 | 1878.8862 | 30.4 |
| | VHS | 15853681 | 2202.0450 | 2202.0455 | 28.4 |

Test Example 2-2: Detection of Molecular Weight after Deglycosylation and Reduction and Amino Acid Sequence of h1902-5 Fused with Different Signal Peptides N-glycosyl carried by h1902-5-1 and h1902-5-2 samples was cut off by PNGase F glycosidase (NEB, P0708), and then the samples were each reduced into light and heavy chains by DTT (Sigma, 43815). Finally, the molecular weight after deglycosylation and reduction of each sample was detected by LC-MS (Waters, ACQUITY UPLC H-Class/XeVo G2-XS QTOF), and data processing and analysis were performed using UNIFI software.

The results are shown in FIGS. 6A-6D. 3.1% signal peptide amino acid (VHS) residue was detected in the heavy chain of the h1902-5-1 sample, while the heavy chain of the h1902-5-2 sample had no signal peptide amino acid residue. No signal peptide amino acid residue was detected in the light chains of both antibodies, and only a small amount of glycated modification was present.

h1902-5-1 was subjected to urea denaturation, DTT was then added for reduction into light and heavy chains, and then Glu C enzyme was added for enzymatic digestion. The molecular weight data of the resulting sample was collected by LC-MS and then analyzed using UNIFI software to obtain the amino acid sequence information of the sample.

The results showed that for h1902-5-1, abnormal peaks that appeared in the detection of the molecular weight after deglycosylation and reduction were confirmed to be VHS amino acid residue through peptide mapping analysis and verification. Specific results are shown in Table 17 below.

TABLE 17

Peptide mapping assay data of h1902-5-1 heavy chain N-terminal signal peptide

| Sample | Terminal extension residue | Intensity | Theoretical molecular weight (Da) | Measured molecular weight (Da) | Retention time (min) |
|---|---|---|---|---|---|
| h1902-5-1 | None | 150012880 | 1286.6952 | 1286.6951 | 25.53 |
| | VHS | 6470631 | 1609.8517 | 1609.8544 | 25.11 |

Test Example 2-3: Detection of Molecular Weight after Deglycosylation and Reduction and Amino Acid Sequence of Anti-FcRn Antibody Fused with Different Signal Peptides N-glycosyl carried by FcRn-1 and FcRn-2 samples was cut off by PNGase F glycosidase (NEB, P0708), and then the samples were each reduced into light and heavy chains by DTT (Sigma, 43815). Finally, the molecular weight after deglycosylation and reduction of each sample was detected by LC-MS (Waters, ACQUITY UPLC H-Class/XeVo G2-XS QTOF), and data processing and analysis were performed using UNIFI software.

The results are shown in FIGS. 7A-7D. 3.4% signal peptide amino acid (VHS) residue was detected in the heavy chain of the FcRn-1 sample, while the heavy chain of the FcRn-2 sample had no signal peptide amino acid residue. No signal peptide amino acid residue was detected in the light chains of both antibodies, and only a small amount of glycated modification was present.

FcRn-1 was subjected to urea denaturation, DTT was then added for reduction into light and heavy chains, and then Glu C enzyme was added for enzymatic digestion. The molecular weight data of the resulting sample was collected by LC-MS and then analyzed using UNIFI software to obtain the amino acid sequence information of the sample.

The results showed that for FcRn-1, abnormal peaks that appeared in the detection of the molecular weight after deglycosylation and reduction were confirmed to be VHS amino acid residue through peptide mapping analysis and verification. Specific results are shown in the table below.

TABLE 18

Peptide mapping assay data of FcRn heavy chain N-terminal signal peptide

| Sample | Terminal extension residue | Intensity | Theoretical molecular weight (Da) | Measured molecular weight (Da) | Retention time (min) |
|---|---|---|---|---|---|
| FcRn-1 | None | 409437184 | 1286.695 | 1286.69506 | 25.69 |
| | VHS | 36230248 | 1609.8521 | 1609.85441 | 25.3 |

Although the foregoing invention has been described in detail by way of drawings and examples for clarity of understanding, the description and examples should not be construed as limiting the scope of the present disclosure. The disclosures of all patents and scientific literature cited herein are clearly incorporated by reference in their entirety.

The invention claimed is:

1. A polypeptide, comprising a signal peptide comprising an amino acid sequence of SEQ ID NO: 5557 or SEQ ID NO: 10556.

2. The polypeptide according to claim 1, wherein the polypeptide further comprises a heterologous polypeptide operably linked to the signal peptide.

3. The polypeptide according to claim 1, wherein the polypeptide comprises an amino acid sequence selected from the group consisting of SEQ ID NO: 157, SEQ ID NO: 158, SEQ ID NO: 159, SEQ ID NO: 160, SEQ ID NO: 163, SEQ ID NO: 164, SEQ ID NO: 165, SEQ ID NO: 166, SEQ ID NO: 171 and SEQ ID NO: 172.

4. A nucleic acid molecule, encoding the polypeptide according to claim 1.

5. A host cell, comprising the nucleic acid molecule according to claim 4.

6. The host cell according to claim 5, wherein the host cell is a CHO cell or a yeast.

* * * * *

SEQUENCE LISTING

```
<160> NUMBER OF SEQ ID NOS: 172

<210> SEQ ID NO 1
<211> LENGTH: 261
<212> TYPE: PRT
<213> ORGANISM: Homo sapiens
<220> FEATURE:
<221> NAME/KEY: PEPTIDE
<222> LOCATION: (1)..(261)
<223> OTHER INFORMATION: Claudin18.2 protein

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
```

```
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 2
<211> LENGTH: 3350
<212> TYPE: DNA
<213> ORGANISM: Homo sapiens
<220> FEATURE:
<221> NAME/KEY: gene
<222> LOCATION: (1)..(3350)
<223> OTHER INFORMATION: Claudin18.2

<400> SEQUENCE: 2

agaattgcgc tgtccacttg tcgtgtggct ctgtgtcgac actgtgcgcc accatggccg     60

tgactgcctg tcagggcttg ggggttcgtgg tttcactgat tgggattgcg ggcatcattg    120

ctgccacctg catggaccag tggagcaccc aagacttgta caacaacccc gtaacagctg    180

ttttcaacta ccaggggctg tggcgctcct gtgtccgaga gagctctggc ttcaccgagt    240

gccggggcta cttcaccctg ctggggctgc cagccatgct gcaggcagtg cgagccctga    300

tgatcgtagg catcgtcctg ggtgccattg gcctcctggt atccatcttt gccctgaaat    360

gcatccgcat tggcagcatg gaggactctg ccaaagccaa catgacactg acctccggga    420

tcatgttcat tgtctcaggt ctttgtgcaa ttgctggagt gtctgtgttt gccaacatgc    480

tggtgactaa cttctggatg tccacagcta acatgtacac cggcatgggt gggatggtgc    540

agactgttca gaccaggtac acatttggtg cggctctgtt cgtgggctgg gtcgctggag    600

gcctcacact aattgggggt gtgatgatgt gcatcgcctg ccggggcctg gcaccagaag    660

aaaccaacta caaagccgtt tcttatcatg cctcaggcca cagtgttgcc tacaagcctg    720

gaggcttcaa ggccagcact ggctttgggt ccaacaccaa aaacaagaag atatacgatg    780

gaggtgcccg cacagaggac gaggtacaat cttatccttc caagcacgac tatgtgtaat    840

gctctaagac ctctcagcac gggcggaaga aactcccgga gagctcaccc aaaaaacaag    900

gagatcccat ctagatttct tcttgctttt gactcacagc tggaagttag aaaagcctcg    960

atttcatctt tggagaggcc aaatggtctt agcctcagtc tctgtctcta aatattccac   1020

cataaaacag ctgagttatt tatgaattag aggctatagc tcacattttc aatcctctat   1080

ttcttttttt aaatataact ttctactctg atgagagaat gtggttttaa tctctctctc   1140

acattttgat gatttagaca gactccccct cttcctccta gtcaataaac ccattgatga   1200

tctatttccc agcttatccc caagaaaact tttgaaagga aagagtagac ccaaagatgt   1260

tattttctgc tgtttgaatt ttgtctcccc acccccaact tggctagtaa taaacactta   1320

ctgaagaaga agcaataaga gaaagatatt tgtaatctct ccagcccatg atctcggttt   1380

tcttacactg tgatcttaaa agttaccaaa ccaaagtcat tttcagtttg aggcaaccaa   1440

acctttctac tgctgttgac atcttcttat tacagcaaca ccattctagg agtttcctga   1500

gctctccact ggagtcctct ttctgtcgcg ggtcagaaat tgtccctaga tgaatgagaa   1560

aattattttt tttaatttaa gtcctaaata tagttaaaat aaataatgtt ttagtaaaat   1620
```

gatacactat ctctgtgaaa tagcctcacc cctacatgtg gatagaagga aatgaaaaaa 1680
taattgcttt gacattgtct atatggtact ttgtaaagtc atgcttaagt acaaattcca 1740
tgaaaagctc actgatccta attctttccc tttgaggtct ctatggctct gattgtacat 1800
gatagtaagt gtaagccatg taaaaagtaa ataatgtctg ggcacagtgg ctcacgcctg 1860
taatcctagc actttgggag gctgaggagg aaggatcact tgagcccaga agttcgagac 1920
tagcctgggc aacatggaga agccctgtct ctacaaaata cagagagaaa aaatcagcca 1980
gtcatggtgg cctacacctg tagtcccagc attccgggag gctgaggtgg gaggatcact 2040
tgagcccagg gaggttgggg ctgcagtgag ccatgatcac accactgcac tccagccagg 2100
tgacatagcg agatcctgtc taaaaaaata aaaaataaat aatggaacac agcaagtcct 2160
aggaagtagg ttaaaactaa ttctttaaaa aaaaaaaaaa gttgagcctg aattaaatgt 2220
aatgtttcca agtgacaggt atccacattt gcatggttac aagccactgc cagttagcag 2280
tagcactttc ctggcactgt ggtcggtttt gttttgtttt gctttgttta gagacggggt 2340
ctcactttcc aggctggcct caaactcctg cactcaagca attcttctac cctggcctcc 2400
caagtagctg gaattacagg tgtgcgccat cacaactagc tggtggtcag ttttgttact 2460
ctgagagctg ttcacttctc tgaattcacc tagagtggtt ggaccatcag atgtttgggc 2520
aaaactgaaa gctctttgca accacacacc ttccctgagc ttacatcact gcccttttga 2580
gcagaaagtc taaattcctt ccaagacagt agaattccat cccagtacca aagccagata 2640
ggccccctag gaaactgagg taagagcagt ctctaaaaac tacccacagc agcattggtg 2700
caggggaact tggccattag gttattattt gagaggaaag tcctcacatc aatagtacat 2760
atgaaagtga cctccaaggg gattggtgaa tactcataag gatcttcagg ctgaacagac 2820
tatgtctggg gaaagaacgg attatgcccc attaaataac aagttgtgtt caagagtcag 2880
agcagtgagc tcagaggccc ttctcactga gacagcaaca tttaaaccaa accagaggaa 2940
gtatttgtgg aactcactgc ctcagtttgg gtaaaggatg agcagacaag tcaactaaag 3000
aaaaaagaaa agcaaggagg agggttgagc aatctagagc atggagtttg ttaagtgctc 3060
tctggatttg agttgaagag catccatttg agttgaaggc cacagggcac aatgagctct 3120
cccttctacc accagaaagt ccctggtcag gtctcaggta gtgcggtgtg gctcagctgg 3180
gtttttaatt agcgcattct ctatccaaca tttaattgtt tgaaagcctc catatagtta 3240
gattgtgctt tgtaattttg ttgttgttgc tctatcttat tgtatatgca ttgagtatta 3300
acctgaatgt tttgttactt aaatattaaa aacactgtta tcctacagtt 3350

<210> SEQ ID NO 3
<211> LENGTH: 120
<212> TYPE: PRT
<213> ORGANISM: Mus musculus
<220> FEATURE:
<221> NAME/KEY: DOMAIN
<222> LOCATION: (1)..(120)
<223> OTHER INFORMATION: Heavy chain variable region of mAb1901 murine antibody

<400> SEQUENCE: 3

Glu Val Gln Leu Met Glu Ser Gly Gly Gly Leu Val Lys Pro Gly Gly
1 5 10 15

Ser Leu Lys Leu Ser Cys Ala Ala Ser Gly Phe Thr Phe Ser Asp Tyr
20 25 30

Gly Ile His Trp Val Arg Gln Ala Pro Glu Met Gly Leu Glu Trp Ile

```
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Tyr Asp Thr Arg Asn Ala Met Asp Tyr Trp Gly Gln
            100                 105                 110

Gly Thr Ser Val Thr Val Ser Ser
        115                 120


<210> SEQ ID NO 4
<211> LENGTH: 113
<212> TYPE: PRT
<213> ORGANISM: Mus musculus
<220> FEATURE:
<221> NAME/KEY: DOMAIN
<222> LOCATION: (1)..(113)
<223> OTHER INFORMATION: Light chain variable region of mAb1901 murine
      antibody

<400> SEQUENCE: 4

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr His Cys Gln Asn
                85                  90                  95

Asp Leu Tyr Tyr Pro Leu Thr Phe Gly Ala Gly Thr Lys Leu Glu Leu
            100                 105                 110

Lys


<210> SEQ ID NO 5
<211> LENGTH: 118
<212> TYPE: PRT
<213> ORGANISM: Mus musculus
<220> FEATURE:
<221> NAME/KEY: DOMAIN
<222> LOCATION: (1)..(118)
<223> OTHER INFORMATION: Heavy chain variable region of mAb1902 murine
      antibody

<400> SEQUENCE: 5

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ser Ser Thr Ala Tyr
```

```
65                  70                  75                  80

Met Gln Leu Ser Ser Leu Pro Ser Glu Asp Ser Ala Val Tyr Tyr Cys
                85                  90                  95

Ala Arg Leu Lys Thr Gly Asn Ser Phe Asp Tyr Trp Gly Gln Gly Thr
            100                 105                 110

Thr Leu Thr Val Ser Ser
        115


<210> SEQ ID NO 6
<211> LENGTH: 113
<212> TYPE: PRT
<213> ORGANISM: Mus musculus
<220> FEATURE:
<221> NAME/KEY: DOMAIN
<222> LOCATION: (1)..(113)
<223> OTHER INFORMATION: Light chain variable region of mAb1902 murine
      antibody

<400> SEQUENCE: 6

Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ala Tyr Thr Tyr Pro Phe Thr Phe Gly Ser Gly Thr Lys Leu Glu Ile
            100                 105                 110

Lys


<210> SEQ ID NO 7
<211> LENGTH: 330
<212> TYPE: PRT
<213> ORGANISM: Homo sapiens
<220> FEATURE:
<221> NAME/KEY: DOMAIN
<222> LOCATION: (1)..(330)
<223> OTHER INFORMATION: Heavy chain constant region of human IgG1
      antibody

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 8
<211> LENGTH: 107
<212> TYPE: PRT
<213> ORGANISM: Homo sapiens
<220> FEATURE:
<221> NAME/KEY: DOMAIN
<222> LOCATION: (1)..(107)
<223> OTHER INFORMATION: Human-derived antibody light chain constant
      region

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 9
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(5)
<223> OTHER INFORMATION: mAb1901 HCDR1

<400> SEQUENCE: 9

Asp Tyr Gly Ile His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(17)
<223> OTHER INFORMATION: mAb1901 HCDR2

<400> SEQUENCE: 10

Tyr Ile Ser Arg Gly Ser Ser Thr Ile Tyr Tyr Ala Asp Thr Val Lys
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(11)
<223> OTHER INFORMATION: mAb1901 HCDR3

<400> SEQUENCE: 11

Gly Gly Tyr Asp Thr Arg Asn Ala Met Asp Tyr
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(17)
<223> OTHER INFORMATION: mAb1901 LCDR1

<400> SEQUENCE: 12

Lys Ser Ser Gln Ser Leu Leu Asn Ser Gly Asn Gln Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthetic Sequence
<220> FEATURE:

<221> NAME/KEY: DOMAIN
<222> LOCATION: (1)..(7)
<223> OTHER INFORMATION: mAb1901 LCDR2

<400> SEQUENCE: 13

Gly Ala Ser Thr Arg Ala Ser
1 5

<210> SEQ ID NO 14
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(9)
<223> OTHER INFORMATION: mAb1901 LCDR3

<400> SEQUENCE: 14

Gln Asn Asp Leu Tyr Tyr Pro Leu Thr
1 5

<210> SEQ ID NO 15
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(5)
<223> OTHER INFORMATION: mAb1902 HCDR1

<400> SEQUENCE: 15

Ser Tyr Trp Met His
1 5

<210> SEQ ID NO 16
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(18)
<223> OTHER INFORMATION: mAb1902 HCDR2

<400> SEQUENCE: 16

Met Ile His Pro Asn Ser Gly Ser Thr Asn Tyr Asn Glu Lys Phe Lys
1 5 10 15

Gly Arg

<210> SEQ ID NO 17
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(9)
<223> OTHER INFORMATION: mAb1902 HCDR3

<400> SEQUENCE: 17

Leu Lys Thr Gly Asn Ser Phe Asp Tyr
1 5

<210> SEQ ID NO 18
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(17)
<223> OTHER INFORMATION: mAb1902 LCDR1

<400> SEQUENCE: 18

Lys Ser Ser Gln Ser Leu Leu Asn Ser Gly Asn Gln Lys Asn Tyr Leu
1 5 10 15

Thr

<210> SEQ ID NO 19
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(7)
<223> OTHER INFORMATION: mAb1902 LCDR2

<400> SEQUENCE: 19

Trp Ala Ser Thr Arg Glu Ser
1 5

<210> SEQ ID NO 20
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(9)
<223> OTHER INFORMATION: mAb1902 LCDR3

<400> SEQUENCE: 20

Gln Asn Ala Tyr Thr Tyr Pro Phe Thr
1 5

<210> SEQ ID NO 21
<211> LENGTH: 113
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(113)
<223> OTHER INFORMATION: VL1

<400> SEQUENCE: 21

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Ala Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asp Leu Tyr Tyr Pro Leu Thr Phe Gly Gln Gly Thr Lys Leu Glu Ile
100 105 110

Lys

<210> SEQ ID NO 22
<211> LENGTH: 113
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(113)
<223> OTHER INFORMATION: VL2

<400> SEQUENCE: 22

Asp Ile Val Met Thr Gln Ser Pro Asp Ser Leu Ala Val Ser Leu Gly
1 5 10 15

Glu Arg Ala Thr Ile Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Ala Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asp Leu Tyr Tyr Pro Leu Thr Phe Gly Gln Gly Thr Lys Leu Glu Ile
100 105 110

Lys

<210> SEQ ID NO 23
<211> LENGTH: 113
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(113)
<223> OTHER INFORMATION: VL3

<400> SEQUENCE: 23

Asp Ile Val Met Thr Gln Ser Pro Asp Ser Leu Ala Val Ser Leu Gly
1 5 10 15

Glu Arg Ala Thr Ile Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Ala Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Ile Tyr His Cys Gln Asn
85 90 95

```
Asp Leu Tyr Tyr Pro Leu Thr Phe Gly Gln Gly Thr Lys Leu Glu Ile
            100                 105                 110

Lys


<210> SEQ ID NO 24
<211> LENGTH: 120
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(120)
<223> OTHER INFORMATION: VH1

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120


<210> SEQ ID NO 25
<211> LENGTH: 120
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(120)
<223> OTHER INFORMATION: VH2

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110
```

```
Gly Thr Thr Val Thr Val Ser Ser
        115                 120


<210> SEQ ID NO 26
<211> LENGTH: 120
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(120)
<223> OTHER INFORMATION: VH3

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120


<210> SEQ ID NO 27
<211> LENGTH: 120
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(120)
<223> OTHER INFORMATION: VH4

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120
```

<210> SEQ ID NO 28
<211> LENGTH: 113
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(113)
<223> OTHER INFORMATION: VL11

<400> SEQUENCE: 28

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys
```

<210> SEQ ID NO 29
<211> LENGTH: 113
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(113)
<223> OTHER INFORMATION: VL12

<400> SEQUENCE: 29

```
Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys
```

<210> SEQ ID NO 30
<211> LENGTH: 113
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(113)
<223> OTHER INFORMATION: VL13

<400> SEQUENCE: 30

Asp Ile Val Leu Thr Gln Ser Pro Asp Ser Leu Ala Val Ser Leu Gly
1 5 10 15

Glu Arg Ala Thr Ile Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Ala Tyr Thr Tyr Pro Phe Thr Phe Gly Gln Gly Thr Lys Leu Glu Ile
100 105 110

Lys

<210> SEQ ID NO 31
<211> LENGTH: 118
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(118)
<223> OTHER INFORMATION: VH11

<400> SEQUENCE: 31

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Val Arg Gln Ala Pro Gly Gln Arg Leu Glu Trp Met
35 40 45

Gly Met Ile His Pro Asn Ser Gly Ser Thr Asn Tyr Asn Glu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Leu Lys Thr Gly Asn Ser Phe Asp Tyr Trp Gly Gln Gly Thr
100 105 110

Thr Val Thr Val Ser Ser
115

<210> SEQ ID NO 32
<211> LENGTH: 118
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN

<222> LOCATION: (1)..(118)
<223> OTHER INFORMATION: VH12

<400> SEQUENCE: 32

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Val Arg Gln Ala Pro Gly Gln Arg Leu Glu Trp Met
35 40 45

Gly Met Ile His Pro Asn Ser Gly Ser Thr Asn Tyr Asn Glu Lys Phe
50 55 60

Lys Gly Arg Val Thr Leu Thr Leu Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Leu Lys Thr Gly Asn Ser Phe Asp Tyr Trp Gly Gln Gly Thr
100 105 110

Thr Val Thr Val Ser Ser
115

<210> SEQ ID NO 33
<211> LENGTH: 118
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(118)
<223> OTHER INFORMATION: VH13

<400> SEQUENCE: 33

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Val Arg Gln Ala Pro Gly Gln Arg Leu Glu Trp Ile
35 40 45

Gly Met Ile His Pro Asn Ser Gly Ser Thr Asn Tyr Asn Glu Lys Phe
50 55 60

Lys Gly Lys Ala Thr Leu Thr Leu Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Leu Lys Thr Gly Asn Ser Phe Asp Tyr Trp Gly Gln Gly Thr
100 105 110

Thr Val Thr Val Ser Ser
115

<210> SEQ ID NO 34
<211> LENGTH: 118
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (1)..(118)
<223> OTHER INFORMATION: VH14

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser
        115

<210> SEQ ID NO 35
<211> LENGTH: 450
<212> TYPE: PRT
<213> ORGANISM: Artificial Sequence
<220> FEATURE:
<223> OTHER INFORMATION: Synthetic Sequence
<220> FEATURE:
<221> NAME/KEY: 1CHAIN
<222> LOCATION: (1)..(450)
<223> OTHER INFORMATION: ch1901 heavy chain

<400> SEQUENCE: 35

Glu Val Gln Leu Met Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Ile His Trp Val Arg Gln Ala Pro Glu Met Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Tyr Asp Thr Arg Asn Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 36
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: ch1901 light chain

<400> SEQUENCE: 36

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr His Cys Gln Asn
                85                  90                  95
```

```
Asp Leu Tyr Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 37
<211> LENGTH: 448
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(448)
<223> OTHER INFORMATION: ch1902 heavy chain

<400> SEQUENCE: 37

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ser Ser Thr Ala Tyr
65                  70                  75                  80

Met Gln Leu Ser Ser Leu Pro Ser Glu Asp Ser Ala Val Tyr Tyr Cys
                85                  90                  95

Ala Arg Leu Lys Thr Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

```
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 38
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: ch1902 light chain

<400> SEQUENCE: 38

Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ala Tyr Thr Tyr Pro Phe Thr Phe Gly Ser Gly Thr Lys Leu Glu Ile
            100                 105                 110
```

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 39
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: L1

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 40
```

```
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: L2

<400> SEQUENCE: 40

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 41
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: L3

<400> SEQUENCE: 41

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr His Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 42
<211> LENGTH: 450
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(450)
<223> OTHER INFORMATION: H1

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 43
<211> LENGTH: 450
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(450)
<223> OTHER INFORMATION: H2

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60
```

```
Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 44
<211> LENGTH: 450
<212> TYPE: PRT

```
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(450)
<223> OTHER INFORMATION: H3

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 45
<211> LENGTH: 450
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(450)
<223> OTHER INFORMATION: H4

<400> SEQUENCE: 45

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Gly Ile His Trp Val Arg Gln Ala Pro Gly Lys Gly Leu Glu Trp Val
35 40 45

Ala Tyr Ile Ser Arg Gly Ser Ser Thr Ile Tyr Tyr Ala Asp Thr Val
50 55 60

Lys Gly Arg Phe Thr Met Ser Arg Asp Asn Ala Lys Asn Ser Leu Tyr
65 70 75 80

Leu Gln Met Thr Ser Leu Arg Ala Glu Asp Thr Ala Val Tyr Tyr Cys
85 90 95

Ala Arg Gly Gly Tyr Asp Thr Arg Asn Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 46
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: L11

<400> SEQUENCE: 46

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Ala Tyr Thr Tyr Pro Phe Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn

```
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 47
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: L12

<400> SEQUENCE: 47

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 48
<211> LENGTH: 220
<212> TYPE: PRT
<213> ORGANISM: Artificial Sequence
<220> FEATURE:
```

<223> OTHER INFORMATION: Synthetic Sequence
<220> FEATURE:
<221> NAME/KEY: CHAIN
<222> LOCATION: (1)..(220)
<223> OTHER INFORMATION: L13

<400> SEQUENCE: 48

Asp Ile Val Leu Thr Gln Ser Pro Asp Ser Leu Ala Val Ser Leu Gly
1 5 10 15

Glu Arg Ala Thr Ile Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Ala Tyr Thr Tyr Pro Phe Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 49
<211> LENGTH: 448
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(448)
<223> OTHER INFORMATION: H11

<400> SEQUENCE: 49

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Val Arg Gln Ala Pro Gly Gln Arg Leu Glu Trp Met
35 40 45

Gly Met Ile His Pro Asn Ser Gly Ser Thr Asn Tyr Asn Glu Lys Phe
50 55 60

Lys Gly Arg Val Thr Ile Thr Arg Asp Thr Ser Ala Ser Thr Ala Tyr
65 70 75 80

```
Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 50
<211> LENGTH: 448
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(448)

<223> OTHER INFORMATION: H12

<400> SEQUENCE: 50

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Val Arg Gln Ala Pro Gly Gln Arg Leu Glu Trp Met
35 40 45

Gly Met Ile His Pro Asn Ser Gly Ser Thr Asn Tyr Asn Glu Lys Phe
50 55 60

Lys Gly Arg Val Thr Leu Thr Leu Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Leu Lys Thr Gly Asn Ser Phe Asp Tyr Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 51
<211> LENGTH: 448
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(448)
<223> OTHER INFORMATION: H13

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 52
<211> LENGTH: 448
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(448)
<223> OTHER INFORMATION: H14

<400> SEQUENCE: 52

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Val Lys Gln Arg Pro Gly Gln Arg Leu Glu Trp Ile
35 40 45

Gly Met Ile His Pro Asn Ser Gly Ser Thr Asn Tyr Asn Glu Lys Phe
50 55 60

Lys Gly Lys Ala Thr Leu Thr Leu Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Leu Lys Thr Gly Asn Ser Phe Asp Tyr Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser

```
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 53
<211> LENGTH: 448
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(448)
<223> OTHER INFORMATION: IMAB-362 heavy chain

<400> SEQUENCE: 53

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95
```

```
Thr Arg Ser Trp Arg Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 54
<211> LENGTH: 220
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(220)
<223> OTHER INFORMATION: IMAB-362 light chain

<400> SEQUENCE: 54

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 55
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide
<220> FEATURE:
<221> NAME/KEY: UNSURE
<222> LOCATION: (16)..(16)
<223> OTHER INFORMATION: Xaa is Val, Ala, Ser, Thr, Gly, Cys, Leu or Ile
<220> FEATURE:
<221> NAME/KEY: UNSURE
<222> LOCATION: (18)..(18)
<223> OTHER INFORMATION: Xaa is Ala, Gly, Ser, Cys, Thr or Gln

<400> SEQUENCE: 55

Met Glu Trp Ser Trp Val Phe Leu Phe Phe Leu Ser Leu Thr Gly Xaa
1               5                   10                  15

His Xaa


<210> SEQ ID NO 56
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
```

<222> LOCATION: (1)..(20)
<223> OTHER INFORMATION: Signal peptide
<220> FEATURE:
<221> NAME/KEY: UNSURE
<222> LOCATION: (18)..(18)
<223> OTHER INFORMATION: Xaa is Val, Ala, Ser, Thr, Gly, Cys, Leu or Ile
<220> FEATURE:
<221> NAME/KEY: UNSURE
<222> LOCATION: (20)..(20)
<223> OTHER INFORMATION: Xaa is Ala, Gly, Ser, Cys, Thr or Gln
<220> FEATURE:
<221> NAME/KEY: UNSURE
<222> LOCATION: (20)..(20)
<223> OTHER INFORMATION: When Xaa(18) is Ala, Xaa(20) is not Cys

<400> SEQUENCE: 56

```
Met Ser Val Pro Thr Gln Val Leu Gly Leu Leu Leu Leu Trp Leu Thr
1               5                   10                  15

Asp Xaa Arg Xaa
            20
```

<210> SEQ ID NO 57
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 57

```
Met Glu Trp Ser Trp Val Phe Leu Phe Phe Leu Ser Leu Thr Gly Val
1               5                   10                  15

His Ala
```

<210> SEQ ID NO 58
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 58

```
Met Glu Trp Ser Trp Val Phe Leu Phe Phe Leu Ser Leu Thr Gly Val
1               5                   10                  15

His Gly
```

<210> SEQ ID NO 59
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 59

```
Met Glu Trp Ser Trp Val Phe Leu Phe Phe Leu Ser Leu Thr Gly Val
1               5                   10                  15

His Ser
```

<210> SEQ ID NO 60
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 60

Met Glu Trp Ser Trp Val Phe Leu Phe Phe Leu Ser Leu Thr Gly Val
1 5 10 15

His Cys

<210> SEQ ID NO 61
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 61

Met Glu Trp Ser Trp Val Phe Leu Phe Phe Leu Ser Leu Thr Gly Val
1 5 10 15

His Thr

<210> SEQ ID NO 62
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 62

Met Glu Trp Ser Trp Val Phe Leu Phe Phe Leu Ser Leu Thr Gly Val
1 5 10 15

His Gln

<210> SEQ ID NO 63
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 63

Met Glu Trp Ser Trp Val Phe Leu Phe Phe Leu Ser Leu Thr Gly Ala
1 5 10 15

His Ala

<210> SEQ ID NO 64

<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 64

Met Glu Trp Ser Trp Val Phe Leu Phe Phe Leu Ser Leu Thr Gly Ala
1 5 10 15

His Gly

<210> SEQ ID NO 65
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 65

Met Glu Trp Ser Trp Val Phe Leu Phe Phe Leu Ser Leu Thr Gly Ala
1 5 10 15

His Ser

<210> SEQ ID NO 66
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 66

Met Glu Trp Ser Trp Val Phe Leu Phe Phe Leu Ser Leu Thr Gly Ala
1 5 10 15

His Cys

<210> SEQ ID NO 67
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 67

Met Glu Trp Ser Trp Val Phe Leu Phe Phe Leu Ser Leu Thr Gly Ala
1 5 10 15

His Thr

<210> SEQ ID NO 68
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 68

Met Glu Trp Ser Trp Val Phe Leu Phe Phe Leu Ser Leu Thr Gly Ala
1 5 10 15

His Gln

<210> SEQ ID NO 69
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 69

Met Glu Trp Ser Trp Val Phe Leu Phe Phe Leu Ser Leu Thr Gly Ser
1 5 10 15

His Ala

<210> SEQ ID NO 70
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 70

Met Glu Trp Ser Trp Val Phe Leu Phe Phe Leu Ser Leu Thr Gly Ser
1 5 10 15

His Gly

<210> SEQ ID NO 71
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 71

Met Glu Trp Ser Trp Val Phe Leu Phe Phe Leu Ser Leu Thr Gly Ser
1 5 10 15

His Ser

<210> SEQ ID NO 72
<211> LENGTH: 18
<212> TYPE: PRT
<213> ORGANISM: Artificial Sequence
<220> FEATURE:
<223> OTHER INFORMATION: Synthetic Sequence
<220> FEATURE:

<221> NAME/KEY: PEPTIDE
<222> LOCATION: (1)..(18)
<223> OTHER INFORMATION: Signal peptide

<400> SEQUENCE: 72

Met Glu Trp Ser Trp Val Phe Leu Phe Phe Leu Ser Leu Thr Gly Ser
1 5 10 15

His Cys

<210> SEQ ID NO 73
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 73

Met Glu Trp Ser Trp Val Phe Leu Phe Phe Leu Ser Leu Thr Gly Ser
1 5 10 15

His Thr

<210> SEQ ID NO 74
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 74

Met Glu Trp Ser Trp Val Phe Leu Phe Phe Leu Ser Leu Thr Gly Ser
1 5 10 15

His Gln

<210> SEQ ID NO 75
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 75

Met Glu Trp Ser Trp Val Phe Leu Phe Phe Leu Ser Leu Thr Gly Thr
1 5 10 15

His Ala

<210> SEQ ID NO 76
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 76

Met Glu Trp Ser Trp Val Phe Leu Phe Phe Leu Ser Leu Thr Gly Thr
1 5 10 15

His Gly

<210> SEQ ID NO 77
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 77

Met Glu Trp Ser Trp Val Phe Leu Phe Phe Leu Ser Leu Thr Gly Thr
1 5 10 15

His Ser

<210> SEQ ID NO 78
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 78

Met Glu Trp Ser Trp Val Phe Leu Phe Phe Leu Ser Leu Thr Gly Thr
1 5 10 15

His Cys

<210> SEQ ID NO 79
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 79

Met Glu Trp Ser Trp Val Phe Leu Phe Phe Leu Ser Leu Thr Gly Thr
1 5 10 15

His Thr

<210> SEQ ID NO 80
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 80

Met Glu Trp Ser Trp Val Phe Leu Phe Phe Leu Ser Leu Thr Gly Thr
1               5                   10                  15

His Gln

<210> SEQ ID NO 81
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 81

Met Glu Trp Ser Trp Val Phe Leu Phe Phe Leu Ser Leu Thr Gly Gly
1               5                   10                  15

His Ala

<210> SEQ ID NO 82
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 82

Met Glu Trp Ser Trp Val Phe Leu Phe Phe Leu Ser Leu Thr Gly Gly
1               5                   10                  15

His Gly

<210> SEQ ID NO 83
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 83

Met Glu Trp Ser Trp Val Phe Leu Phe Phe Leu Ser Leu Thr Gly Gly
1               5                   10                  15

His Ser

<210> SEQ ID NO 84
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 84

Met Glu Trp Ser Trp Val Phe Leu Phe Phe Leu Ser Leu Thr Gly Gly
1               5                   10                  15

His Cys

<210> SEQ ID NO 85
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 85

Met Glu Trp Ser Trp Val Phe Leu Phe Phe Leu Ser Leu Thr Gly Gly
1 5 10 15

His Thr

<210> SEQ ID NO 86
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 86

Met Glu Trp Ser Trp Val Phe Leu Phe Phe Leu Ser Leu Thr Gly Gly
1 5 10 15

His Gln

<210> SEQ ID NO 87
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 87

Met Glu Trp Ser Trp Val Phe Leu Phe Phe Leu Ser Leu Thr Gly Cys
1 5 10 15

His Ala

<210> SEQ ID NO 88
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 88

Met Glu Trp Ser Trp Val Phe Leu Phe Phe Leu Ser Leu Thr Gly Cys
1 5 10 15

His Gly

<210> SEQ ID NO 89
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 89

```
Met Glu Trp Ser Trp Val Phe Leu Phe Phe Leu Ser Leu Thr Gly Cys
1               5                   10                  15

His Ser
```

<210> SEQ ID NO 90
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 90

```
Met Glu Trp Ser Trp Val Phe Leu Phe Phe Leu Ser Leu Thr Gly Cys
1               5                   10                  15

His Cys
```

<210> SEQ ID NO 91
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 91

```
Met Glu Trp Ser Trp Val Phe Leu Phe Phe Leu Ser Leu Thr Gly Cys
1               5                   10                  15

His Thr
```

<210> SEQ ID NO 92
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 92

```
Met Glu Trp Ser Trp Val Phe Leu Phe Phe Leu Ser Leu Thr Gly Cys
1               5                   10                  15

His Gln
```

<210> SEQ ID NO 93
<211> LENGTH: 18
<212> TYPE: PRT

<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 93

Met Glu Trp Ser Trp Val Phe Leu Phe Phe Leu Ser Leu Thr Gly Leu
1 5 10 15

His Ala

<210> SEQ ID NO 94
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 94

Met Glu Trp Ser Trp Val Phe Leu Phe Phe Leu Ser Leu Thr Gly Leu
1 5 10 15

His Gly

<210> SEQ ID NO 95
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 95

Met Glu Trp Ser Trp Val Phe Leu Phe Phe Leu Ser Leu Thr Gly Leu
1 5 10 15

His Ser

<210> SEQ ID NO 96
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 96

Met Glu Trp Ser Trp Val Phe Leu Phe Phe Leu Ser Leu Thr Gly Leu
1 5 10 15

His Cys

<210> SEQ ID NO 97
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 97

Met Glu Trp Ser Trp Val Phe Leu Phe Phe Leu Ser Leu Thr Gly Leu
1 5 10 15

His Thr

<210> SEQ ID NO 98
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 98

Met Glu Trp Ser Trp Val Phe Leu Phe Phe Leu Ser Leu Thr Gly Leu
1 5 10 15

His Gln

<210> SEQ ID NO 99
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 99

Met Glu Trp Ser Trp Val Phe Leu Phe Phe Leu Ser Leu Thr Gly Ile
1 5 10 15

His Ala

<210> SEQ ID NO 100
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 100

Met Glu Trp Ser Trp Val Phe Leu Phe Phe Leu Ser Leu Thr Gly Ile
1 5 10 15

His Gly

<210> SEQ ID NO 101
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)

<223> OTHER INFORMATION: Signal peptide

<400> SEQUENCE: 101

Met Glu Trp Ser Trp Val Phe Leu Phe Phe Leu Ser Leu Thr Gly Ile
1 5 10 15

His Ser

<210> SEQ ID NO 102
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 102

Met Glu Trp Ser Trp Val Phe Leu Phe Phe Leu Ser Leu Thr Gly Ile
1 5 10 15

His Cys

<210> SEQ ID NO 103
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 103

Met Glu Trp Ser Trp Val Phe Leu Phe Phe Leu Ser Leu Thr Gly Ile
1 5 10 15

His Thr

<210> SEQ ID NO 104
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(18)
<223> OTHER INFORMATION: Signal peptide

<400> SEQUENCE: 104

Met Glu Trp Ser Trp Val Phe Leu Phe Phe Leu Ser Leu Thr Gly Ile
1 5 10 15

His Gln

<210> SEQ ID NO 105
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 105

```
Met Ser Val Pro Thr Gln Val Leu Gly Leu Leu Leu Leu Trp Leu Thr
1               5                   10                  15

Asp Val Arg Ala
            20


<210> SEQ ID NO 106
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 106

Met Ser Val Pro Thr Gln Val Leu Gly Leu Leu Leu Leu Trp Leu Thr
1               5                   10                  15

Asp Val Arg Gly
            20


<210> SEQ ID NO 107
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 107

Met Ser Val Pro Thr Gln Val Leu Gly Leu Leu Leu Leu Trp Leu Thr
1               5                   10                  15

Asp Val Arg Ser
            20


<210> SEQ ID NO 108
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 108

Met Ser Val Pro Thr Gln Val Leu Gly Leu Leu Leu Leu Trp Leu Thr
1               5                   10                  15

Asp Val Arg Cys
            20


<210> SEQ ID NO 109
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide
```

<400> SEQUENCE: 109

Met Ser Val Pro Thr Gln Val Leu Gly Leu Leu Leu Leu Trp Leu Thr
1 5 10 15

Asp Val Arg Thr
20

<210> SEQ ID NO 110
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 110

Met Ser Val Pro Thr Gln Val Leu Gly Leu Leu Leu Leu Trp Leu Thr
1 5 10 15

Asp Val Arg Gln
20

<210> SEQ ID NO 111
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 111

Met Ser Val Pro Thr Gln Val Leu Gly Leu Leu Leu Leu Trp Leu Thr
1 5 10 15

Asp Ala Arg Ala
20

<210> SEQ ID NO 112
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 112

Met Ser Val Pro Thr Gln Val Leu Gly Leu Leu Leu Leu Trp Leu Thr
1 5 10 15

Asp Ala Arg Gly
20

<210> SEQ ID NO 113
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 113

Met Ser Val Pro Thr Gln Val Leu Gly Leu Leu Leu Leu Trp Leu Thr
1 5 10 15

Asp Ala Arg Ser
20

<210> SEQ ID NO 114
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 114

Met Ser Val Pro Thr Gln Val Leu Gly Leu Leu Leu Leu Trp Leu Thr
1 5 10 15

Asp Ala Arg Thr
20

<210> SEQ ID NO 115
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 115

Met Ser Val Pro Thr Gln Val Leu Gly Leu Leu Leu Leu Trp Leu Thr
1 5 10 15

Asp Ala Arg Gln
20

<210> SEQ ID NO 116
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 116

Met Ser Val Pro Thr Gln Val Leu Gly Leu Leu Leu Leu Trp Leu Thr
1 5 10 15

Asp Ser Arg Ala
20

<210> SEQ ID NO 117
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)

<223> OTHER INFORMATION: Signal peptide

<400> SEQUENCE: 117

Met Ser Val Pro Thr Gln Val Leu Gly Leu Leu Leu Leu Trp Leu Thr
1 5 10 15

Asp Ser Arg Gly
20

<210> SEQ ID NO 118
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 118

Met Ser Val Pro Thr Gln Val Leu Gly Leu Leu Leu Leu Trp Leu Thr
1 5 10 15

Asp Ser Arg Ser
20

<210> SEQ ID NO 119
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 119

Met Ser Val Pro Thr Gln Val Leu Gly Leu Leu Leu Leu Trp Leu Thr
1 5 10 15

Asp Ser Arg Cys
20

<210> SEQ ID NO 120
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 120

Met Ser Val Pro Thr Gln Val Leu Gly Leu Leu Leu Leu Trp Leu Thr
1 5 10 15

Asp Ser Arg Thr
20

<210> SEQ ID NO 121
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 121

Met Ser Val Pro Thr Gln Val Leu Gly Leu Leu Leu Leu Trp Leu Thr
1 5 10 15

Asp Ser Arg Gln
20

<210> SEQ ID NO 122
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 122

Met Ser Val Pro Thr Gln Val Leu Gly Leu Leu Leu Leu Trp Leu Thr
1 5 10 15

Asp Thr Arg Ala
20

<210> SEQ ID NO 123
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 123

Met Ser Val Pro Thr Gln Val Leu Gly Leu Leu Leu Leu Trp Leu Thr
1 5 10 15

Asp Thr Arg Gly
20

<210> SEQ ID NO 124
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 124

Met Ser Val Pro Thr Gln Val Leu Gly Leu Leu Leu Leu Trp Leu Thr
1 5 10 15

Asp Thr Arg Ser
20

<210> SEQ ID NO 125
<211> LENGTH: 20
<212> TYPE: PRT
<213> ORGANISM: Artificial Sequence
<220> FEATURE:
<223> OTHER INFORMATION: Synthetic Sequence
<220> FEATURE:

<221> NAME/KEY: PEPTIDE
<222> LOCATION: (1)..(20)
<223> OTHER INFORMATION: Signal peptide

<400> SEQUENCE: 125

Met Ser Val Pro Thr Gln Val Leu Gly Leu Leu Leu Leu Trp Leu Thr
1               5                   10                  15

Asp Thr Arg Cys
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 126

Met Ser Val Pro Thr Gln Val Leu Gly Leu Leu Leu Leu Trp Leu Thr
1               5                   10                  15

Asp Thr Arg Thr
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 127

Met Ser Val Pro Thr Gln Val Leu Gly Leu Leu Leu Leu Trp Leu Thr
1               5                   10                  15

Asp Thr Arg Gln
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 128

Met Ser Val Pro Thr Gln Val Leu Gly Leu Leu Leu Leu Trp Leu Thr
1               5                   10                  15

Asp Gly Arg Ala
            20

<210> SEQ ID NO 129
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 129

Met Ser Val Pro Thr Gln Val Leu Gly Leu Leu Leu Leu Trp Leu Thr
1 5 10 15

Asp Gly Arg Gly
20

<210> SEQ ID NO 130
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 130

Met Ser Val Pro Thr Gln Val Leu Gly Leu Leu Leu Leu Trp Leu Thr
1 5 10 15

Asp Gly Arg Ser
20

<210> SEQ ID NO 131
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 131

Met Ser Val Pro Thr Gln Val Leu Gly Leu Leu Leu Leu Trp Leu Thr
1 5 10 15

Asp Gly Arg Cys
20

<210> SEQ ID NO 132
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 132

Met Ser Val Pro Thr Gln Val Leu Gly Leu Leu Leu Leu Trp Leu Thr
1 5 10 15

Asp Gly Arg Thr
20

<210> SEQ ID NO 133
<211> LENGTH: 20
<212> TYPE: PRT
<213> ORGANISM: Artificial Sequence
<220> FEATURE:

<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 133

Met Ser Val Pro Thr Gln Val Leu Gly Leu Leu Leu Leu Trp Leu Thr
1               5                   10                  15

Asp Gly Arg Gln
            20

<210> SEQ ID NO 134
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 134

Met Ser Val Pro Thr Gln Val Leu Gly Leu Leu Leu Leu Trp Leu Thr
1               5                   10                  15

Asp Cys Arg Ala
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 135

Met Ser Val Pro Thr Gln Val Leu Gly Leu Leu Leu Leu Trp Leu Thr
1               5                   10                  15

Asp Cys Arg Gly
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 136

Met Ser Val Pro Thr Gln Val Leu Gly Leu Leu Leu Leu Trp Leu Thr
1               5                   10                  15

Asp Cys Arg Ser
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 137

Met Ser Val Pro Thr Gln Val Leu Gly Leu Leu Leu Leu Trp Leu Thr
1 5 10 15

Asp Cys Arg Cys
20

<210> SEQ ID NO 138
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 138

Met Ser Val Pro Thr Gln Val Leu Gly Leu Leu Leu Leu Trp Leu Thr
1 5 10 15

Asp Cys Arg Thr
20

<210> SEQ ID NO 139
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 139

Met Ser Val Pro Thr Gln Val Leu Gly Leu Leu Leu Leu Trp Leu Thr
1 5 10 15

Asp Cys Arg Gln
20

<210> SEQ ID NO 140
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 140

Met Ser Val Pro Thr Gln Val Leu Gly Leu Leu Leu Leu Trp Leu Thr
1 5 10 15

Asp Leu Arg Ala
20

<210> SEQ ID NO 141
<211> LENGTH: 20
<212> TYPE: PRT

```
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 141

Met Ser Val Pro Thr Gln Val Leu Gly Leu Leu Leu Leu Trp Leu Thr
1               5                   10                  15

Asp Leu Arg Gly
            20


<210> SEQ ID NO 142
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 142

Met Ser Val Pro Thr Gln Val Leu Gly Leu Leu Leu Leu Trp Leu Thr
1               5                   10                  15

Asp Leu Arg Ser
            20


<210> SEQ ID NO 143
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 143

Met Ser Val Pro Thr Gln Val Leu Gly Leu Leu Leu Leu Trp Leu Thr
1               5                   10                  15

Asp Leu Arg Cys
            20


<210> SEQ ID NO 144
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 144

Met Ser Val Pro Thr Gln Val Leu Gly Leu Leu Leu Leu Trp Leu Thr
1               5                   10                  15

Asp Leu Arg Thr
            20


<210> SEQ ID NO 145
<211> LENGTH: 20
```

<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 145

```
Met Ser Val Pro Thr Gln Val Leu Gly Leu Leu Leu Leu Trp Leu Thr
1               5                   10                  15

Asp Leu Arg Gln
            20
```

<210> SEQ ID NO 146
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 146

```
Met Ser Val Pro Thr Gln Val Leu Gly Leu Leu Leu Leu Trp Leu Thr
1               5                   10                  15

Asp Ile Arg Ala
            20
```

<210> SEQ ID NO 147
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 147

```
Met Ser Val Pro Thr Gln Val Leu Gly Leu Leu Leu Leu Trp Leu Thr
1               5                   10                  15

Asp Ile Arg Gly
            20
```

<210> SEQ ID NO 148
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 148

```
Met Ser Val Pro Thr Gln Val Leu Gly Leu Leu Leu Leu Trp Leu Thr
1               5                   10                  15

Asp Ile Arg Ser
            20
```

<210> SEQ ID NO 149

<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 149

Met Ser Val Pro Thr Gln Val Leu Gly Leu Leu Leu Leu Trp Leu Thr
1 5 10 15

Asp Ile Arg Cys
20

<210> SEQ ID NO 150
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 150

Met Ser Val Pro Thr Gln Val Leu Gly Leu Leu Leu Leu Trp Leu Thr
1 5 10 15

Asp Ile Arg Thr
20

<210> SEQ ID NO 151
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 151

Met Ser Val Pro Thr Gln Val Leu Gly Leu Leu Leu Leu Trp Leu Thr
1 5 10 15

Asp Ile Arg Gln
20

<210> SEQ ID NO 152
<211> LENGTH: 19
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(19)
<223> OTHER INFORMATION: Signal peptide

<400> SEQUENCE: 152

Met Glu Trp Ser Trp Val Phe Leu Phe Phe Leu Ser Val Thr Thr Gly
1 5 10 15

Val His Ser

<210> SEQ ID NO 153

```
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: PEPTIDE
<222> LOCATION: (1)..(20)
<223> OTHER INFORMATION: Signal peptide

<400> SEQUENCE: 153

Met Ser Val Pro Thr Gln Val Leu Gly Leu Leu Leu Leu Trp Leu Thr
1               5                   10                  15

Asp Ala Arg Cys
            20


<210> SEQ ID NO 154
<211> LENGTH: 468
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(468)
<223> OTHER INFORMATION: Pertuzumab-1 antibody heavy chain containing
      signal peptide

<400> SEQUENCE: 154

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
```

```
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 155
<211> LENGTH: 234
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(234)
<223> OTHER INFORMATION: Pertuzumab-1 antibody light chain containing
      signal peptide

<400> SEQUENCE: 155

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Ile Gly Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Tyr
            100                 105                 110
```

```
Ile Tyr Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 156
<211> LENGTH: 233
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(233)
<223> OTHER INFORMATION: Pertuzumab-2 antibody heavy chain containing
      signal peptide

<400> SEQUENCE: 156

Met Glu Trp Ser Trp Val Phe Leu Phe Phe Leu Ser Val Thr Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Asp Val
        35                  40                  45

Ser Ile Gly Val Ala Trp Tyr Gln Gln Lys Pro Gly Lys Ala Pro Lys
    50                  55                  60

Leu Leu Ile Tyr Ser Ala Ser Tyr Arg Tyr Thr Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Tyr Ile
            100                 105                 110

Tyr Pro Tyr Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205
```

```
Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 157
<211> LENGTH: 467
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(467)
<223> OTHER INFORMATION: Pertuzumab-3 antibody heavy chain containing
      signal peptide

<400> SEQUENCE: 157

Met Glu Trp Ser Trp Val Phe Leu Phe Phe Leu Ser Leu Thr Gly Val
1               5                   10                  15

His Ala Glu Val Gln Leu Val Glu Ser Gly Gly Gly Leu Val Gln Pro
            20                  25                  30

Gly Gly Ser Leu Arg Leu Ser Cys Ala Ala Ser Gly Phe Thr Phe Thr
        35                  40                  45

Asp Tyr Thr Met Asp Trp Val Arg Gln Ala Pro Gly Lys Gly Leu Glu
    50                  55                  60

Trp Val Ala Asp Val Asn Pro Asn Ser Gly Gly Ser Ile Tyr Asn Gln
65                  70                  75                  80

Arg Phe Lys Gly Arg Phe Thr Leu Ser Val Asp Arg Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asn Leu Gly Pro Ser Phe Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
```

```
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 158
<211> LENGTH: 234
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(234)
<223> OTHER INFORMATION: Pertuzumab-3 antibody light chain containing
      signal peptide

<400> SEQUENCE: 158

Met Ser Val Pro Thr Gln Val Leu Gly Leu Leu Leu Leu Trp Leu Thr
1               5                   10                  15

Asp Val Arg Ala Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Ile Gly Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Tyr
            100                 105                 110

Ile Tyr Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 159
<211> LENGTH: 232
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(232)
<223> OTHER INFORMATION: Pertuzumab-4 antibody light chain containing signal peptide

<400> SEQUENCE: 159

```
Met Glu Trp Ser Trp Val Phe Leu Phe Phe Leu Ser Leu Thr Gly Val
1               5                   10                  15

His Ala Asp Ile Gln Met Thr Gln Ser Pro Ser Ser Leu Ser Ala Ser
            20                  25                  30

Val Gly Asp Arg Val Thr Ile Thr Cys Lys Ala Ser Gln Asp Val Ser
        35                  40                  45

Ile Gly Val Ala Trp Tyr Gln Gln Lys Pro Gly Lys Ala Pro Lys Leu
    50                  55                  60

Leu Ile Tyr Ser Ala Ser Tyr Arg Tyr Thr Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys Gln Gln Tyr Tyr Ile Tyr
            100                 105                 110

Pro Tyr Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 160
<211> LENGTH: 469
<212> TYPE: PRT
<213> ORGANISM: Artificial Sequence
<220> FEATURE:

```
<223> OTHER INFORMATION: Synthetic Sequence
<220> FEATURE:
<221> NAME/KEY: CHAIN
<222> LOCATION: (1)..(469)
<223> OTHER INFORMATION: Pertuzumab-5 antibody heavy chain containing
      signal peptide

<400> SEQUENCE: 160

Met Ser Val Pro Thr Gln Val Leu Gly Leu Leu Leu Leu Trp Leu Thr
1               5                   10                  15

Asp Val Arg Ala Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Thr Asp Tyr Thr Met Asp Trp Val Arg Gln Ala Pro Gly Lys Gly
    50                  55                  60

Leu Glu Trp Val Ala Asp Val Asn Pro Asn Ser Gly Gly Ser Ile Tyr
65                  70                  75                  80

Asn Gln Arg Phe Lys Gly Arg Phe Thr Leu Ser Val Asp Arg Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asn Leu Gly Pro Ser Phe Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
```

370 375 380

Val Ser Leu Thr Cys Leu Val Lys Gly Phe Tyr Pro Ser Asp Ile Ala
385 390 395 400

Val Glu Trp Glu Ser Asn Gly Gln Pro Glu Asn Asn Tyr Lys Thr Thr
405 410 415

Pro Pro Val Leu Asp Ser Asp Gly Ser Phe Phe Leu Tyr Ser Lys Leu
420 425 430

Thr Val Asp Lys Ser Arg Trp Gln Gln Gly Asn Val Phe Ser Cys Ser
435 440 445

Val Met His Glu Ala Leu His Asn His Tyr Thr Gln Lys Ser Leu Ser
450 455 460

Leu Ser Pro Gly Lys
465

<210> SEQ ID NO 161
<211> LENGTH: 467
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(467)
<223> OTHER INFORMATION: h1902-5-1 antibody heavy chain containing signal peptide

<400> SEQUENCE: 161

Met Glu Trp Ser Trp Val Phe Leu Phe Phe Leu Ser Val Thr Thr Gly
1 5 10 15

Val His Ser Glu Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Ser Tyr Trp Met His Trp Val Arg Gln Ala Pro Gly Gln Arg Leu
50 55 60

Glu Trp Met Gly Met Ile His Pro Asn Ser Gly Ser Thr Asn Tyr Asn
65 70 75 80

Glu Lys Phe Lys Gly Arg Val Thr Ile Thr Arg Asp Thr Ser Ala Ser
85 90 95

Thr Ala Tyr Met Glu Leu Ser Ser Leu Arg Ser Glu Asp Thr Ala Val
100 105 110

Tyr Tyr Cys Ala Arg Leu Lys Thr Gly Asn Ser Phe Asp Tyr Trp Gly
115 120 125

Gln Gly Thr Thr Val Thr Val Ser Ser Ala Ser Thr Lys Gly Pro Ser
130 135 140

Val Phe Pro Leu Ala Pro Ser Ser Lys Ser Thr Ser Gly Gly Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Ser Leu Gly Thr Gln Thr Tyr Ile Cys Asn Val Asn His
210 215 220

Lys Pro Ser Asn Thr Lys Val Asp Lys Lys Val Glu Pro Lys Ser Cys
225 230 235 240

Asp Lys Thr His Thr Cys Pro Pro Cys Pro Ala Pro Glu Leu Leu Gly
245 250 255

Gly Pro Ser Val Phe Leu Phe Pro Pro Lys Pro Lys Asp Thr Leu Met
260 265 270

Ile Ser Arg Thr Pro Glu Val Thr Cys Val Val Val Asp Val Ser His
275 280 285

Glu Asp Pro Glu Val Lys Phe Asn Trp Tyr Val Asp Gly Val Glu Val
290 295 300

His Asn Ala Lys Thr Lys Pro Arg Glu Glu Gln Tyr Asn Ser Thr Tyr
305 310 315 320

Arg Val Val Ser Val Leu Thr Val Leu His Gln Asp Trp Leu Asn Gly
325 330 335

Lys Glu Tyr Lys Cys Lys Val Ser Asn Lys Ala Leu Pro Ala Pro Ile
340 345 350

Glu Lys Thr Ile Ser Lys Ala Lys Gly Gln Pro Arg Glu Pro Gln Val
355 360 365

Tyr Thr Leu Pro Pro Ser Arg Asp Glu Leu Thr Lys Asn Gln Val Ser
370 375 380

Leu Thr Cys Leu Val Lys Gly Phe Tyr Pro Ser Asp Ile Ala Val Glu
385 390 395 400

Trp Glu Ser Asn Gly Gln Pro Glu Asn Asn Tyr Lys Thr Thr Pro Pro
405 410 415

Val Leu Asp Ser Asp Gly Ser Phe Phe Leu Tyr Ser Lys Leu Thr Val
420 425 430

Asp Lys Ser Arg Trp Gln Gln Gly Asn Val Phe Ser Cys Ser Val Met
435 440 445

His Glu Ala Leu His Asn His Tyr Thr Gln Lys Ser Leu Ser Leu Ser
450 455 460

Pro Gly Lys
465

<210> SEQ ID NO 162
<211> LENGTH: 239
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(239)
<223> OTHER INFORMATION: h1902-5-1 antibody light chain containing signal peptide

<400> SEQUENCE: 162

Met Glu Trp Ser Trp Val Phe Leu Phe Phe Leu Ser Val Thr Thr Gly
1 5 10 15

Val His Ser Asp Ile Val Leu Thr Gln Ser Pro Asp Ser Leu Ala Val
20 25 30

Ser Leu Gly Glu Arg Ala Thr Ile Asn Cys Lys Ser Ser Gln Ser Leu
35 40 45

Leu Asn Ser Gly Asn Gln Lys Asn Tyr Leu Thr Trp Tyr Gln Gln Lys
50 55 60

Pro Gly Gln Pro Pro Lys Leu Leu Ile Tyr Trp Ala Ser Thr Arg Glu
65 70 75 80

Ser Gly Val Pro Asp Arg Phe Ser Gly Ser Gly Ser Gly Thr Asp Phe
85 90 95

Thr Leu Thr Ile Ser Ser Leu Gln Ala Glu Asp Val Ala Val Tyr Tyr
100 105 110

Cys Gln Asn Ala Tyr Thr Tyr Pro Phe Thr Phe Gly Gln Gly Thr Lys
115 120 125

Leu Glu Ile Lys Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn Phe Tyr Pro Arg Glu Ala Lys Val Gln Trp Lys Val Asp
165 170 175

Asn Ala Leu Gln Ser Gly Asn Ser Gln Glu Ser Val Thr Glu Gln Asp
180 185 190

Ser Lys Asp Ser Thr Tyr Ser Leu Ser Ser Thr Leu Thr Leu Ser Lys
195 200 205

Ala Asp Tyr Glu Lys His Lys Val Tyr Ala Cys Glu Val Thr His Gln
210 215 220

Gly Leu Ser Ser Pro Val Thr Lys Ser Phe Asn Arg Gly Glu Cys
225 230 235

<210> SEQ ID NO 163
<211> LENGTH: 466
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(466)
<223> OTHER INFORMATION: h1902-5-2 antibody heavy chain containing signal peptide

<400> SEQUENCE: 163

Met Glu Trp Ser Trp Val Phe Leu Phe Phe Leu Ser Leu Thr Gly Val
1 5 10 15

His Ala Glu Val Gln Leu Val Gln Ser Gly Ala Glu Val Lys Lys Pro
20 25 30

Gly Ala Ser Val Lys Val Ser Cys Lys Ala Ser Gly Tyr Thr Phe Thr
35 40 45

Ser Tyr Trp Met His Trp Val Arg Gln Ala Pro Gly Gln Arg Leu Glu
50 55 60

Trp Met Gly Met Ile His Pro Asn Ser Gly Ser Thr Asn Tyr Asn Glu
65 70 75 80

Lys Phe Lys Gly Arg Val Thr Ile Thr Arg Asp Thr Ser Ala Ser Thr
85 90 95

Ala Tyr Met Glu Leu Ser Ser Leu Arg Ser Glu Asp Thr Ala Val Tyr
100 105 110

Tyr Cys Ala Arg Leu Lys Thr Gly Asn Ser Phe Asp Tyr Trp Gly Gln
115 120 125

Gly Thr Thr Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys Asp Tyr Phe Pro Glu Pro Val Thr Val Ser
165 170 175

Trp Asn Ser Gly Ala Leu Thr Ser Gly Val His Thr Phe Pro Ala Val
180 185 190

Leu Gln Ser Ser Gly Leu Tyr Ser Leu Ser Ser Val Val Thr Val Pro

```
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 164
<211> LENGTH: 240
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(240)
<223> OTHER INFORMATION: h1902-5-2 antibody light chain containing
      signal peptide

<400> SEQUENCE: 164

Met Ser Val Pro Thr Gln Val Leu Gly Leu Leu Leu Leu Trp Leu Thr
1               5                   10                  15

Asp Val Arg Ala Asp Ile Val Leu Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Asn Ser Gly Asn Gln Lys Asn Tyr Leu Thr Trp Tyr Gln Gln
    50                  55                  60
```

```
Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Asn Ala Tyr Thr Tyr Pro Phe Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 165
<211> LENGTH: 468
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(468)
<223> OTHER INFORMATION: h1902-5-3 antibody heavy chain containing
      signal peptide

<400> SEQUENCE: 165

Met Ser Val Pro Thr Gln Val Leu Gly Leu Leu Leu Leu Trp Leu Thr
1               5                   10                  15

Asp Val Arg Ala Glu Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Ser Tyr Trp Met His Trp Val Arg Gln Ala Pro Gly Gln Arg
    50                  55                  60

Leu Glu Trp Met Gly Met Ile His Pro Asn Ser Gly Ser Thr Asn Tyr
65                  70                  75                  80

Asn Glu Lys Phe Lys Gly Arg Val Thr Ile Thr Arg Asp Thr Ser Ala
                85                  90                  95

Ser Thr Ala Tyr Met Glu Leu Ser Ser Leu Arg Ser Glu Asp Thr Ala
            100                 105                 110

Val Tyr Tyr Cys Ala Arg Leu Lys Thr Gly Asn Ser Phe Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160
```

```
Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 166
<211> LENGTH: 238
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(238)
<223> OTHER INFORMATION: h1902-5-3 antibody light chain containing
      signal peptide

<400> SEQUENCE: 166

Met Glu Trp Ser Trp Val Phe Leu Phe Phe Leu Ser Leu Thr Gly Val
1               5                   10                  15

His Ala Asp Ile Val Leu Thr Gln Ser Pro Asp Ser Leu Ala Val Ser
```

```
            20                  25                  30

Leu Gly Glu Arg Ala Thr Ile Asn Cys Lys Ser Ser Gln Ser Leu Leu
        35                  40                  45

Asn Ser Gly Asn Gln Lys Asn Tyr Leu Thr Trp Tyr Gln Gln Lys Pro
    50                  55                  60

Gly Gln Pro Pro Lys Leu Leu Ile Tyr Trp Ala Ser Thr Arg Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Asn Ala Tyr Thr Tyr Pro Phe Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 167
<211> LENGTH: 449
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(449)
<223> OTHER INFORMATION: Heavy chain of anti-FcRn antibody

<400> SEQUENCE: 167

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Asn Lys His
            20                  25                  30

Tyr Ile Ala Trp Val Arg Gln Met Pro Gly Lys Gly Leu Glu Trp Met
        35                  40                  45

Gly Ile Ile Tyr Pro Asp Asn Ser Asn Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Gly Gly Pro Thr Phe Ala Gln Trp Tyr Phe Asp Tyr Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 168
<211> LENGTH: 218
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(218)
<223> OTHER INFORMATION: Light chain of anti-FcRn antibody

<400> SEQUENCE: 168

Asn Phe Met Leu Thr Gln Pro His Ser Val Ser Glu Ser Pro Gly Lys
1               5                   10                  15
```

Thr Val Thr Ile Ser Cys Thr Gly Ser Ser Gly Ser Ile Ala Ser Asn
20 25 30

Tyr Val Gln Trp Tyr Gln Gln Arg Pro Gly Ser Ser Pro Thr Thr Val
35 40 45

Ile Tyr Glu Asp Asn Gln Arg Ala Ser Gly Val Pro Asp Arg Phe Ser
50 55 60

Gly Ser Ile Asp Ser Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Ser
85 90 95

Ser Ser His Asn Trp Val Phe Gly Gly Gly Thr Lys Leu Thr Val Leu
100 105 110

Gly Gln Pro Lys Ala Asn Pro Thr Val Thr Leu Phe Pro Pro Ser Ser
115 120 125

Glu Glu Leu Gln Ala Asn Lys Ala Thr Leu Val Cys Leu Ile Ser Asp
130 135 140

Phe Tyr Pro Gly Ala Val Thr Val Ala Trp Lys Ala Asp Gly Ser Pro
145 150 155 160

Val Lys Ala Gly Val Glu Thr Thr Lys Pro Ser Lys Gln Ser Asn Asn
165 170 175

Lys Tyr Ala Ala Ser Ser Tyr Leu Ser Leu Thr Pro Glu Gln Trp Lys
180 185 190

Ser His Arg Ser Tyr Ser Cys Gln Val Thr His Glu Gly Ser Thr Val
195 200 205

Glu Lys Thr Val Ala Pro Thr Glu Cys Ser
210 215

<210> SEQ ID NO 169
<211> LENGTH: 468
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(468)
<223> OTHER INFORMATION: Amino acid sequence of FcRn-1 antibody heavy chain containing signal peptide

<400> SEQUENCE: 169

Met Glu Trp Ser Trp Val Phe Leu Phe Phe Leu Ser Val Thr Thr Gly
1 5 10 15

Val His Ser Glu Val Gln Leu Val Gln Ser Gly Ala Glu Val Lys Lys
20 25 30

Pro Gly Glu Ser Leu Lys Ile Ser Cys Lys Gly Ser Gly Tyr Asn Phe
35 40 45

Asn Lys His Tyr Ile Ala Trp Val Arg Gln Met Pro Gly Lys Gly Leu
50 55 60

Glu Trp Met Gly Ile Ile Tyr Pro Asp Asn Ser Asn Thr Ile Tyr Ser
65 70 75 80

Pro Ser Phe Gln Gly Gln Val Thr Ile Ser Ala Asp Lys Ser Ile Ser
85 90 95

Thr Ala Tyr Leu Gln Trp Ser Ser Leu Lys Ala Ser Asp Thr Ala Met
100 105 110

Tyr Tyr Cys Ala Arg Phe Gly Gly Pro Thr Phe Ala Gln Trp Tyr Phe
115 120 125

Asp Tyr Trp Gly Gln Gly Thr Leu Val Thr Val Ser Ser Ala Ser Thr

```
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465
```

<210> SEQ ID NO 170
<211> LENGTH: 237
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(237)
<223> OTHER INFORMATION: Amino acid sequence of FcRn-1 antibody light chain containing signal peptide

<400> SEQUENCE: 170

Met Glu Trp Ser Trp Val Phe Leu Phe Phe Leu Ser Val Thr Thr Gly
1 5 10 15

Val His Ser Asn Phe Met Leu Thr Gln Pro His Ser Val Ser Glu Ser
20 25 30

Pro Gly Lys Thr Val Thr Ile Ser Cys Thr Gly Ser Ser Gly Ser Ile
35 40 45

Ala Ser Asn Tyr Val Gln Trp Tyr Gln Gln Arg Pro Gly Ser Ser Pro
50 55 60

Thr Thr Val Ile Tyr Glu Asp Asn Gln Arg Ala Ser Gly Val Pro Asp
65 70 75 80

Arg Phe Ser Gly Ser Ile Asp Ser Ser Ser Asn Ser Ala Ser Leu Thr
85 90 95

Ile Ser Gly Leu Lys Thr Glu Asp Glu Ala Asp Tyr Tyr Cys Gln Ser
100 105 110

Tyr Asp Ser Ser Ser His Asn Trp Val Phe Gly Gly Gly Thr Lys Leu
115 120 125

Thr Val Leu Gly Gln Pro Lys Ala Asn Pro Thr Val Thr Leu Phe Pro
130 135 140

Pro Ser Ser Glu Glu Leu Gln Ala Asn Lys Ala Thr Leu Val Cys Leu
145 150 155 160

Ile Ser Asp Phe Tyr Pro Gly Ala Val Thr Val Ala Trp Lys Ala Asp
165 170 175

Gly Ser Pro Val Lys Ala Gly Val Glu Thr Thr Lys Pro Ser Lys Gln
180 185 190

Ser Asn Asn Lys Tyr Ala Ala Ser Ser Tyr Leu Ser Leu Thr Pro Glu
195 200 205

Gln Trp Lys Ser His Arg Ser Tyr Ser Cys Gln Val Thr His Glu Gly
210 215 220

Ser Thr Val Glu Lys Thr Val Ala Pro Thr Glu Cys Ser
225 230 235

<210> SEQ ID NO 171
<211> LENGTH: 467
<212> TYPE: PRT
<213> ORGANISM: Artificial Sequence
<220> FEATURE:
<223> OTHER INFORMATION: Synthetic Sequence
<220> FEATURE:
<221> NAME/KEY: CHAIN
<222> LOCATION: (1)..(467)
<223> OTHER INFORMATION: Amino acid sequence of FcRn-2 antibody heavy chain containing signal peptide

<400> SEQUENCE: 171

Met Glu Trp Ser Trp Val Phe Leu Phe Phe Leu Ser Leu Thr Gly Val
1 5 10 15

His Ala Glu Val Gln Leu Val Gln Ser Gly Ala Glu Val Lys Lys Pro
20 25 30

Gly Glu Ser Leu Lys Ile Ser Cys Lys Gly Ser Gly Tyr Asn Phe Asn
35 40 45

Lys His Tyr Ile Ala Trp Val Arg Gln Met Pro Gly Lys Gly Leu Glu
50 55 60

Trp Met Gly Ile Ile Tyr Pro Asp Asn Ser Asn Thr Ile Tyr Ser Pro
65 70 75 80

Ser Phe Gln Gly Gln Val Thr Ile Ser Ala Asp Lys Ser Ile Ser Thr
85 90 95

```
Ala Tyr Leu Gln Trp Ser Ser Leu Lys Ala Ser Asp Thr Ala Met Tyr
            100                 105                 110

Tyr Cys Ala Arg Phe Gly Gly Pro Thr Phe Ala Gln Trp Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465
```

<210> SEQ ID NO 172
<211> LENGTH: 236
<212> TYPE: PRT
<213> ORGANISM: Artificial Sequence
<220> FEATURE:
<223> OTHER INFORMATION: Synthetic Sequence

```
<220> FEATURE:
<221> NAME/KEY: CHAIN
<222> LOCATION: (1)..(236)
<223> OTHER INFORMATION: Amino acid sequence of FcRn-2 antibody light
      chain containing signal peptide

<400> SEQUENCE: 172

Met Glu Trp Ser Trp Val Phe Leu Phe Phe Leu Ser Leu Thr Gly Val
1               5                   10                  15

His Ala Asn Phe Met Leu Thr Gln Pro His Ser Val Ser Glu Ser Pro
            20                  25                  30

Gly Lys Thr Val Thr Ile Ser Cys Thr Gly Ser Ser Gly Ser Ile Ala
        35                  40                  45

Ser Asn Tyr Val Gln Trp Tyr Gln Gln Arg Pro Gly Ser Ser Pro Thr
    50                  55                  60

Thr Val Ile Tyr Glu Asp Asn Gln Arg Ala Ser Gly Val Pro Asp Arg
65                  70                  75                  80

Phe Ser Gly Ser Ile Asp Ser Ser Ser Asn Ser Ala Ser Leu Thr Ile
                85                  90                  95

Ser Gly Leu Lys Thr Glu Asp Glu Ala Asp Tyr Tyr Cys Gln Ser Tyr
            100                 105                 110

Asp Ser Ser Ser His Asn Trp Val Phe Gly Gly Gly Thr Lys Leu Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235
```